US010306745B2

(12) United States Patent
Aoki et al.

(10) Patent No.: US 10,306,745 B2
(45) Date of Patent: May 28, 2019

(54) ACCELERATOR AND PARTICLE BEAM IRRADIATION SYSTEM

(71) Applicant: Hitachi, Ltd., Tokyo (JP)

(72) Inventors: Takamichi Aoki, Tokyo (JP); Fuutarou Ebina, Tokyo (JP); Hideaki Nishiuchi, Tokyo (JP); Shigemitsu Hara, Tokyo (JP); Masumi Umezawa, Tokyo (JP); Takayoshi Seki, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 16 days.

(21) Appl. No.: 15/531,806

(22) PCT Filed: Dec. 8, 2014

(86) PCT No.: PCT/JP2014/082464
§ 371 (c)(1),
(2) Date: May 31, 2017

(87) PCT Pub. No.: WO2016/092622
PCT Pub. Date: Jun. 16, 2016

(65) Prior Publication Data
US 2017/0318657 A1 Nov. 2, 2017

(51) Int. Cl.
*A61N 5/10* (2006.01)
*H05H 7/00* (2006.01)
(Continued)

(52) U.S. Cl.
CPC ............ *H05H 7/001* (2013.01); *A61N 5/10* (2013.01); *A61N 5/1077* (2013.01); *H05H 7/02* (2013.01);
(Continued)

(58) Field of Classification Search
None
See application file for complete search history.

(56) References Cited

U.S. PATENT DOCUMENTS 5,818,058 A * 10/1998 Nakanishi ............... A61N 5/10
250/492.3
6,316,776 B1 * 11/2001 Hiramoto ............. A61N 5/1042
250/492.3
(Continued)

FOREIGN PATENT DOCUMENTS

JP 60-3900 A 1/1985
JP 02-270300 A 11/1990
(Continued)

OTHER PUBLICATIONS

Japanese Office Action received in corresponding Japanese Application No. 2016-563314 dated Jun. 26, 2018.
(Continued)

*Primary Examiner* — Dion Ferguson
*Assistant Examiner* — Srinivas Sathiraju
(74) *Attorney, Agent, or Firm* — Mattingly & Malur, PC

(57) ABSTRACT

An accelerator 4 includes a circular vacuum container including circular return yokes 5A, 5B. An injection electrode 18 is disposed closer to an inlet of a beam extraction path 20 in the return yoke 5B than a central axis C of the vacuum container. Magnetic poles 7A to 7F are radially disposed from the injection electrode 18 at the periphery of the injection electrode 18 in the return yoke 5B. Recessions 29A to 29F are disposed alternately with the magnetic poles 7A to 7F in the circumferential direction of the return yoke 5B. In the vacuum container, a concentric trajectory region, in which multiple beam turning trajectories centered around the injection electrode 18 are present, is formed, and an eccentric trajectory region, in which multiple beam turning trajectories eccentric from the injection electrode 18 are present, is formed around the region.

18 Claims, 40 Drawing Sheets

(51) Int. Cl.
*H05H 7/02* (2006.01)
*H05H 7/04* (2006.01)
*H05H 13/04* (2006.01)
*H05H 7/08* (2006.01)
*H05H 13/00* (2006.01)

(52) U.S. Cl.
CPC ............... *H05H 7/04* (2013.01); *H05H 7/08* (2013.01); *H05H 13/005* (2013.01); *H05H 13/04* (2013.01); *A61N 2005/1087* (2013.01); *H05H 2007/002* (2013.01); *H05H 2007/004* (2013.01); *H05H 2007/008* (2013.01); *H05H 2007/025* (2013.01); *H05H 2007/045* (2013.01); *H05H 2007/048* (2013.01); *H05H 2007/082* (2013.01); *H05H 2007/087* (2013.01)

(56) References Cited

U.S. PATENT DOCUMENTS

| | | | | |
|---|---|---|---|---|
| 6,433,494 B1 * | 8/2002 | Kulish | ............ | H05H 1/54 250/251 |
| 7,317,192 B2 * | 1/2008 | Ma | ............ | G21K 1/08 250/298 |
| 7,656,258 B1 * | 2/2010 | Antaya | ............ | H01F 6/00 313/62 |
| 7,982,416 B2 * | 7/2011 | Tanaka | ............ | H05H 7/04 315/503 |
| 8,111,125 B2 * | 2/2012 | Antaya | ............ | H05H 7/04 335/297 |
| 8,440,987 B2 * | 5/2013 | Stephani | ............ | H01J 3/14 250/492.1 |
| 8,558,485 B2 * | 10/2013 | Antaya | ............ | H05H 13/005 315/500 |
| 8,564,225 B1 * | 10/2013 | Hailey | ............ | H05H 9/042 315/500 |
| 8,581,525 B2 * | 11/2013 | Antaya | ............ | H05H 13/005 315/500 |
| 8,836,249 B2 * | 9/2014 | Bertozzi | ............ | H05H 13/08 315/500 |
| 8,963,108 B2 * | 2/2015 | Matteo | ............ | A61N 5/1081 250/492.3 |
| 8,981,250 B2 * | 3/2015 | Foret | ............ | A23B 4/015 110/246 |
| 9,031,200 B2 * | 5/2015 | Ho | ............ | H05H 7/12 315/5 |
| 9,894,747 B2 * | 2/2018 | Parnaste | ............ | H05H 13/005 |
| 2006/0027766 A1 * | 2/2006 | Matsuda | ............ | A61N 5/10 250/496.1 |
| 2006/0163495 A1 * | 7/2006 | Hiramoto | ............ | A61N 5/1049 250/492.3 |
| 2008/0292497 A1 * | 11/2008 | Vangeneugden | ............ | A61L 2/10 422/29 |
| 2010/0060209 A1 * | 3/2010 | Balakin | ............ | H05H 7/10 315/505 |
| 2010/0219757 A1 * | 9/2010 | Benzerrouk | ............ | H01J 37/32009 315/111.51 |
| 2011/0101246 A1 * | 5/2011 | Yajima | ............ | A61N 5/10 250/492.3 |
| 2011/0170757 A1 * | 7/2011 | Pan | ............ | A61B 6/032 382/131 |
| 2011/0188638 A1 * | 8/2011 | Treas | ............ | H05H 7/02 378/137 |
| 2011/0216886 A1 * | 9/2011 | Ho | ............ | H05H 7/12 378/137 |
| 2011/0284437 A1 * | 11/2011 | Johnson | ............ | C02F 1/4608 210/150 |
| 2012/0020844 A1 * | 1/2012 | Foret | ............ | A23B 4/015 422/184.1 |
| 2012/0215090 A1 * | 8/2012 | Pan | ............ | A61B 6/032 600/407 |
| 2012/0229053 A1 * | 9/2012 | Yu | ............ | H05H 7/22 315/505 |
| 2012/0250370 A1 * | 10/2012 | Taniguchi | ............ | H02M 3/33561 363/34 |
| 2013/0009571 A1 * | 1/2013 | Antaya | ............ | H05H 13/005 315/502 |
| 2013/0063052 A1 * | 3/2013 | Ho | ............ | H05H 7/12 315/505 |

FOREIGN PATENT DOCUMENTS

| | | |
|---|---|---|
| JP | 10-118204 A | 5/1998 |
| JP | 3472657 B2 | 12/2003 |
| JP | 2004-358237 A | 12/2004 |
| JP | 2006-239403 A | 9/2006 |
| JP | 2010-287419 A | 12/2010 |
| JP | 2010287419 A * | 12/2010 |
| JP | 2011-092424 A | 5/2011 |
| JP | 2014-160613 A | 9/2014 |

OTHER PUBLICATIONS

International Search Report of PCT/JP2014/082464 dated Feb. 17, 2015.

* cited by examiner

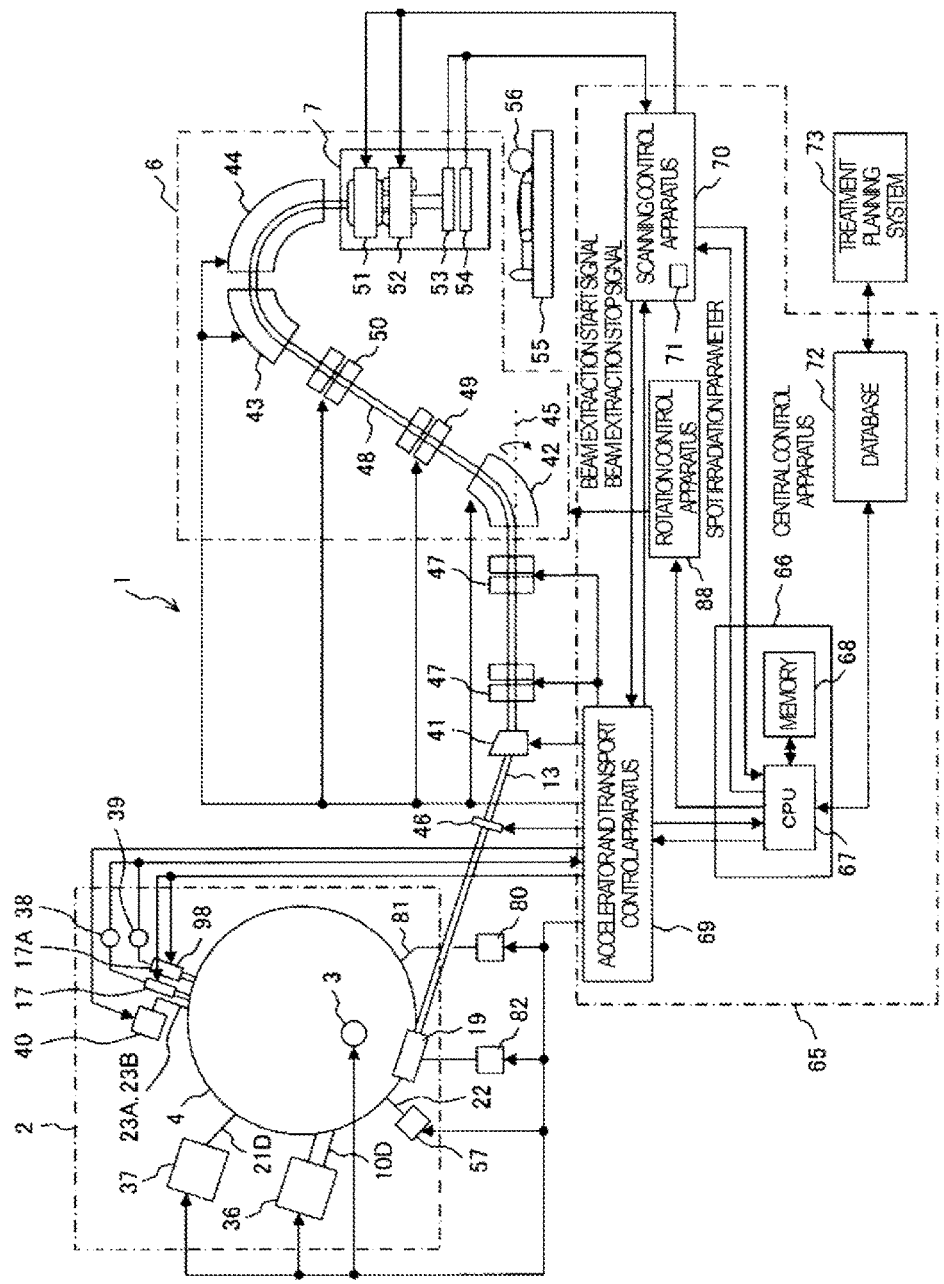
[Fig. 1]

[Fig. 2]
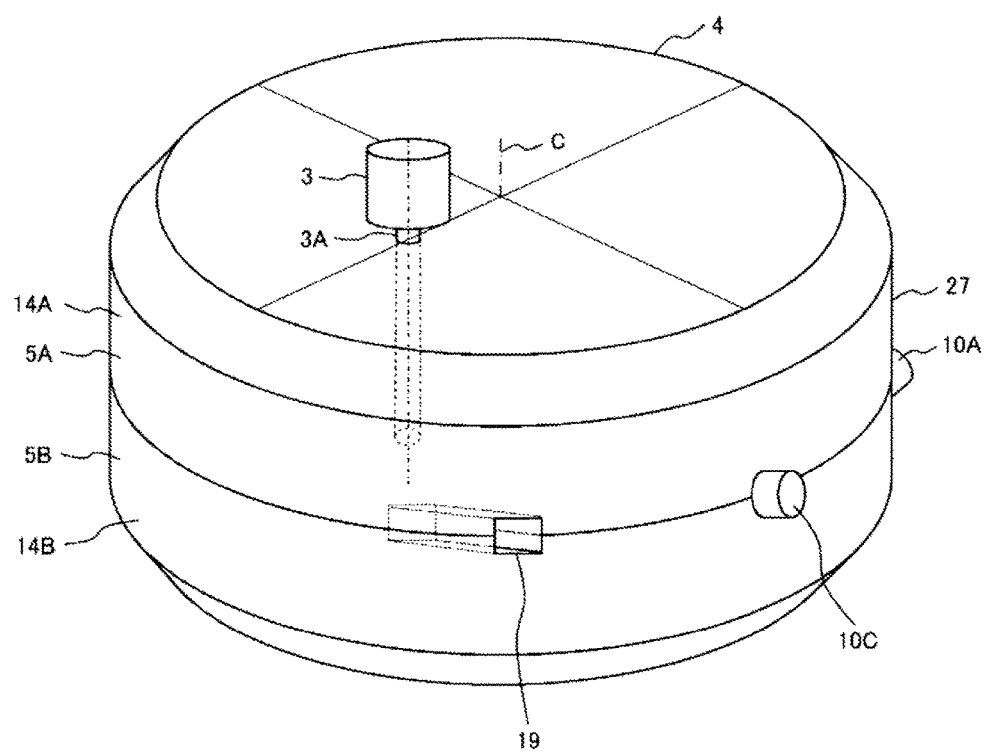

[Fig. 3]
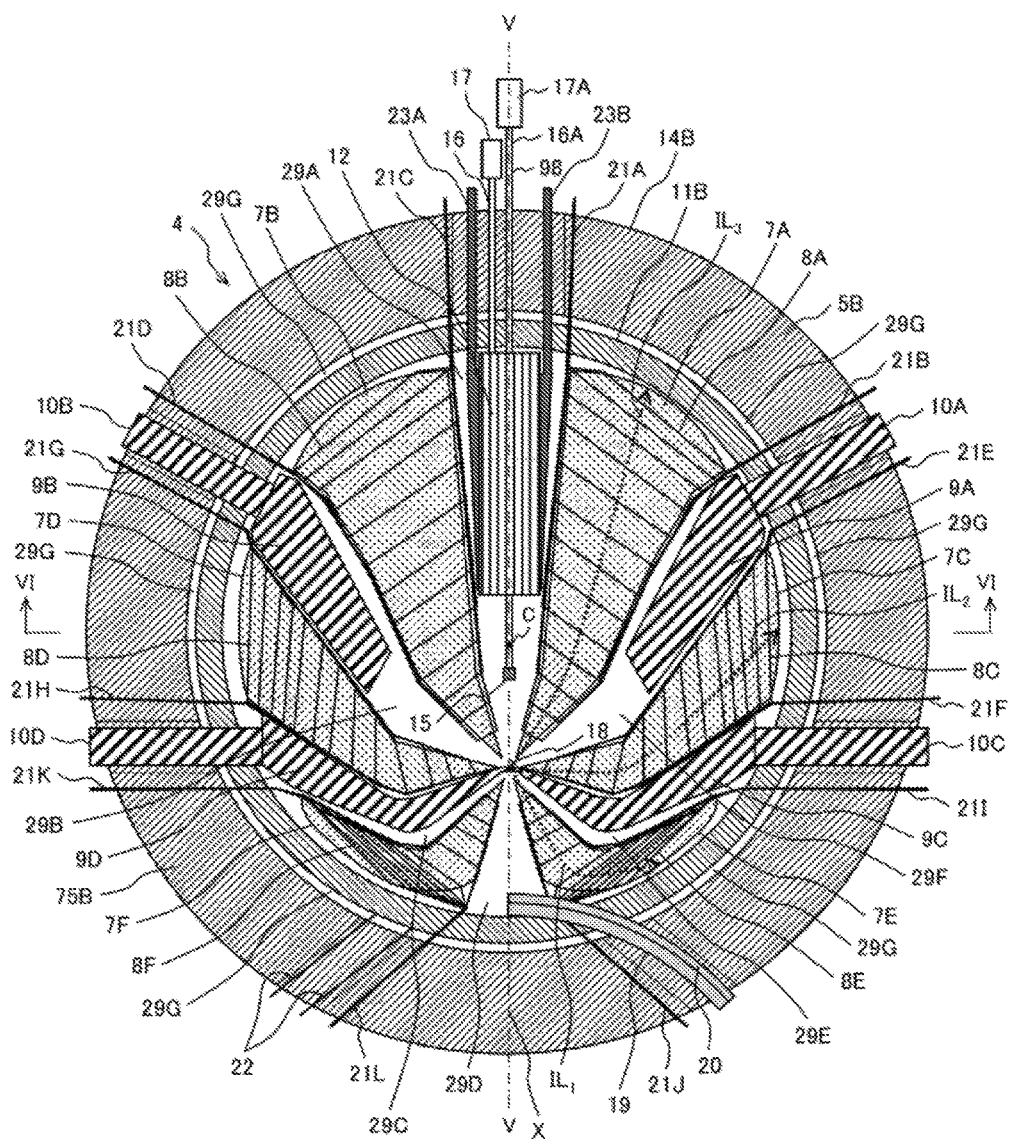

[Fig. 4]
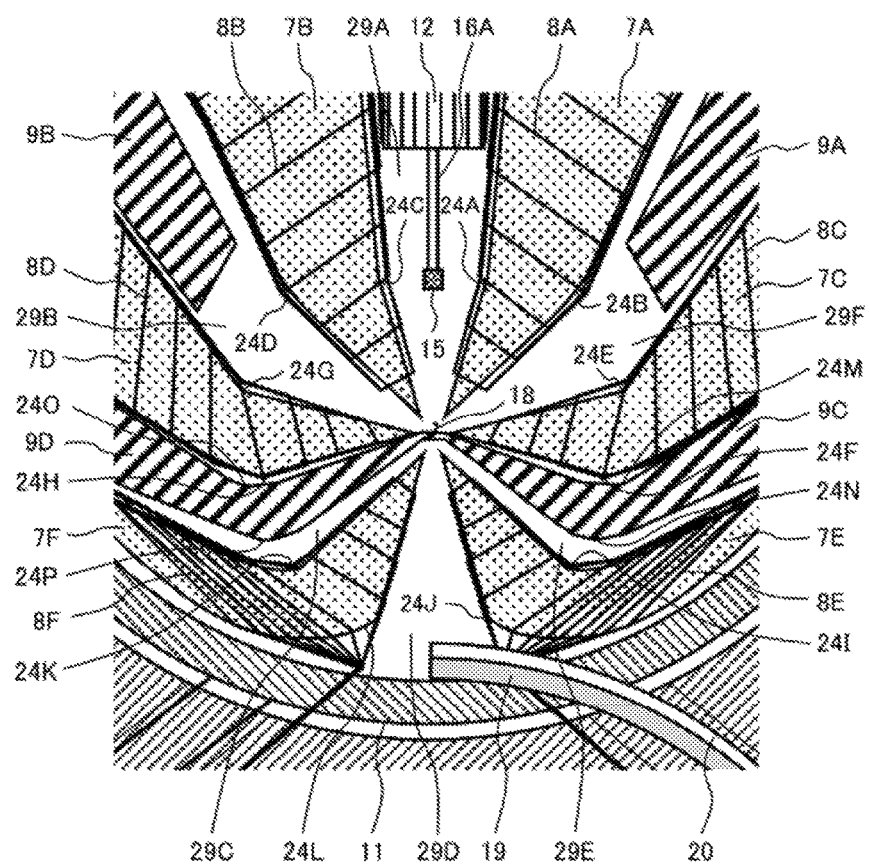

[Fig. 5]
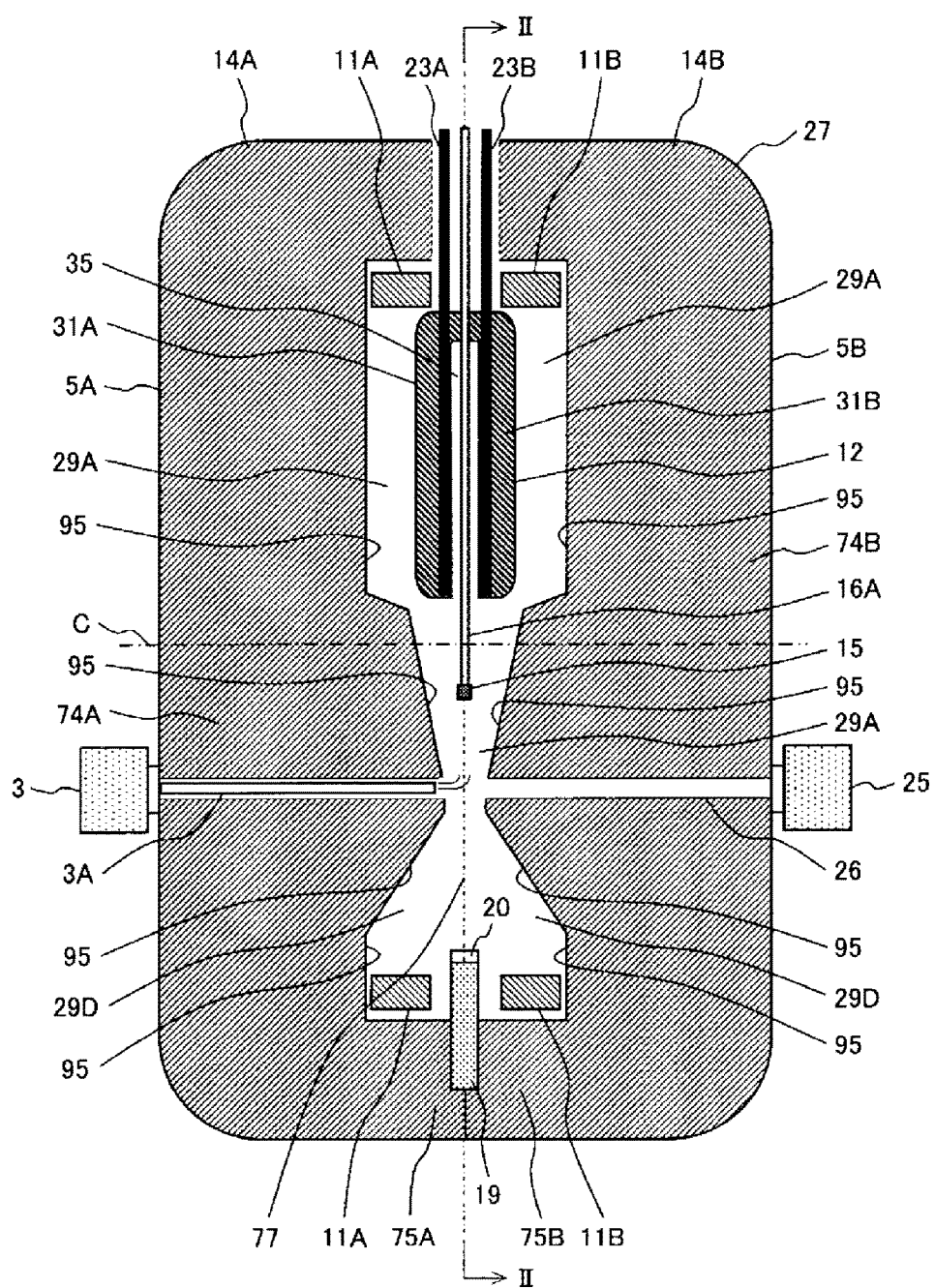

[Fig. 6]
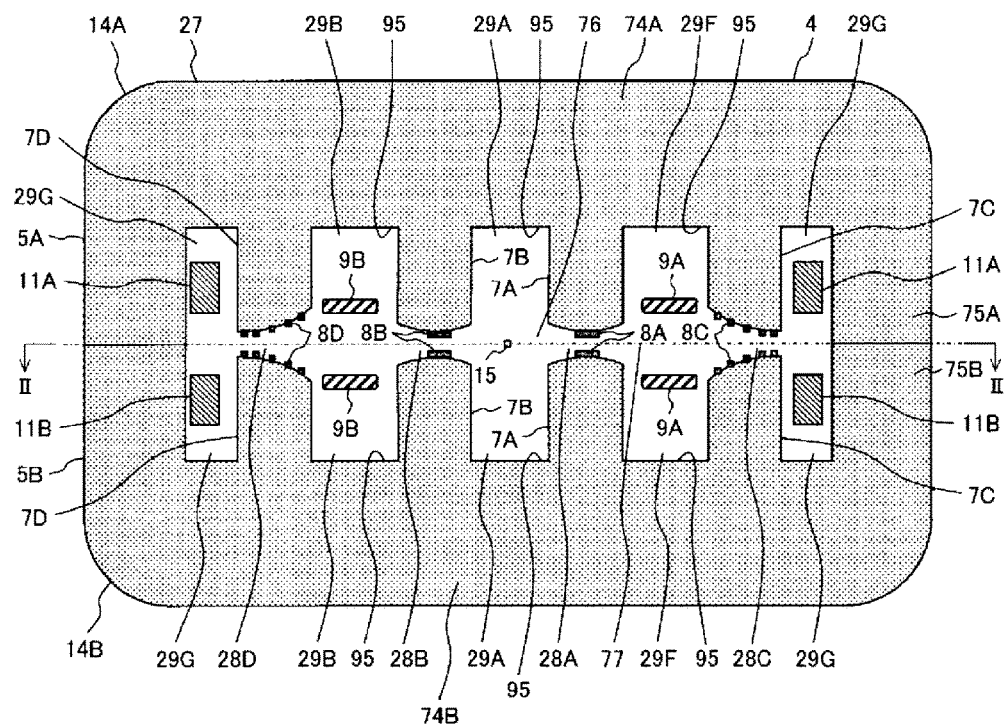
[Fig. 7]
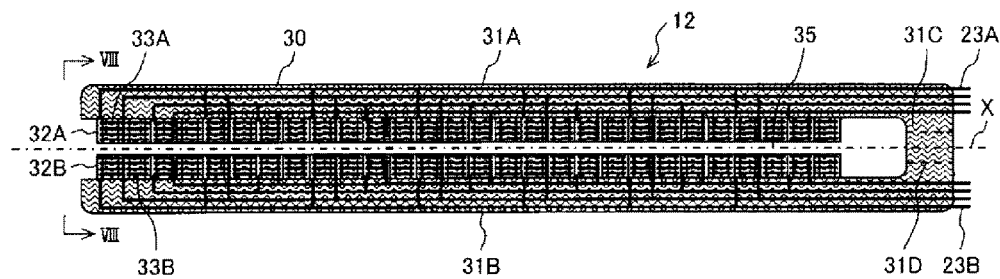

[Fig. 8]
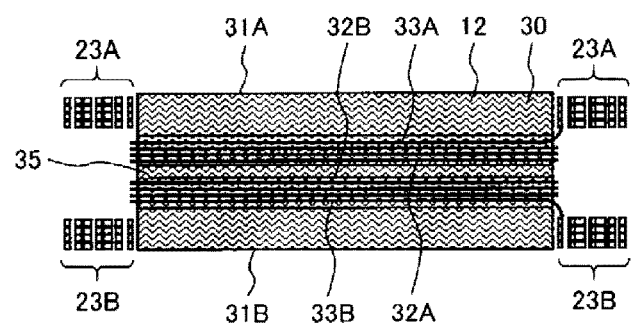

[Fig. 9]

[Fig. 10]
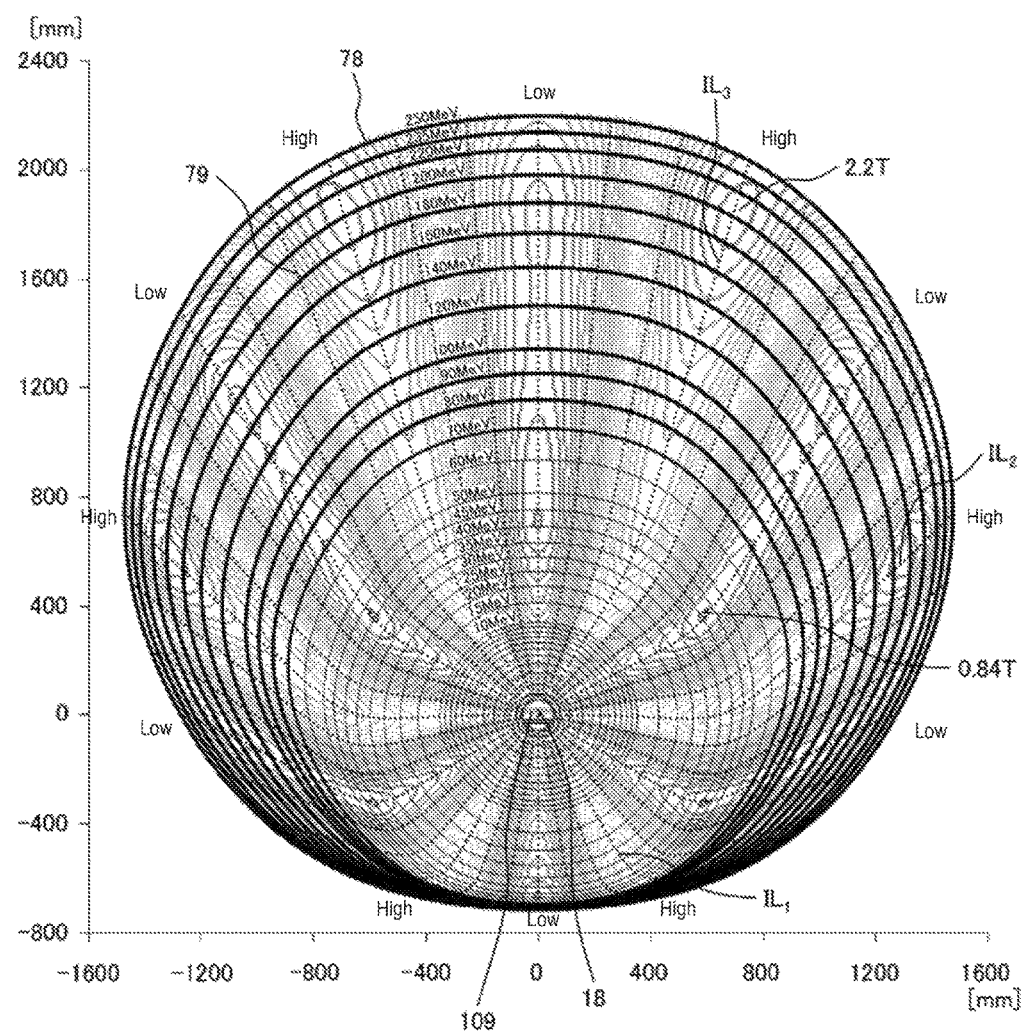

[Fig. 11]
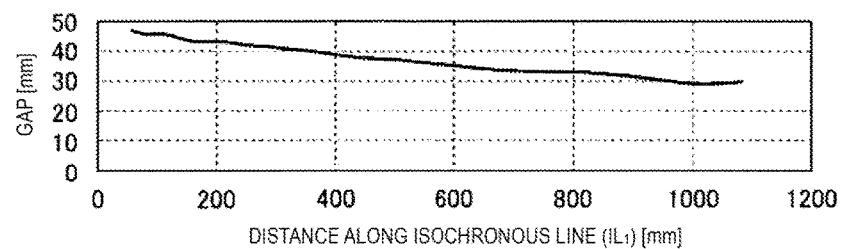
[Fig. 12]
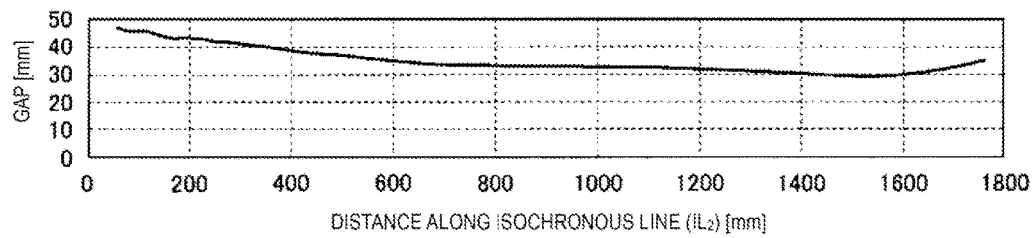
[Fig. 13]
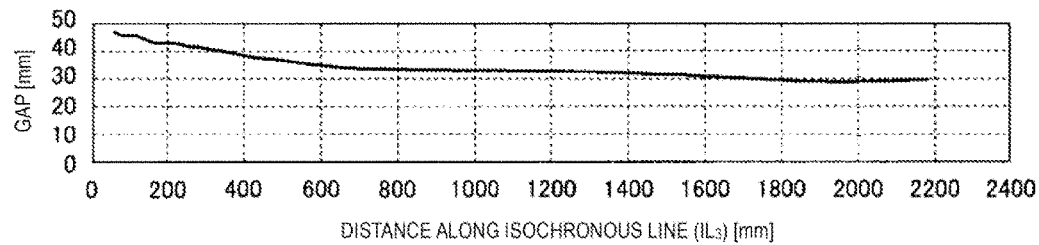

[Fig. 14]
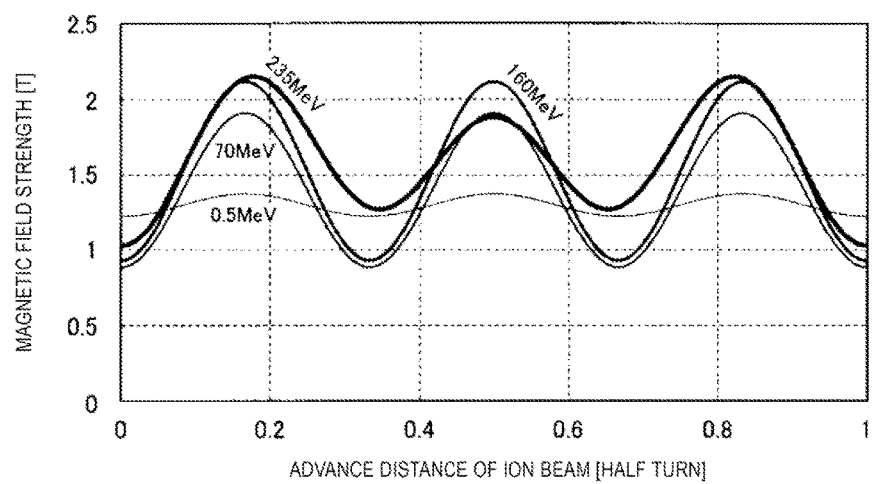
[Fig. 15]
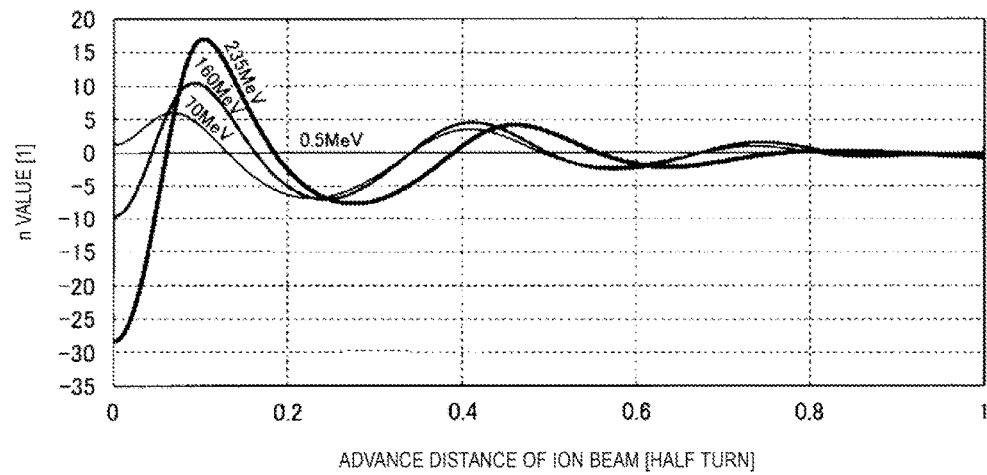

[Fig. 16]
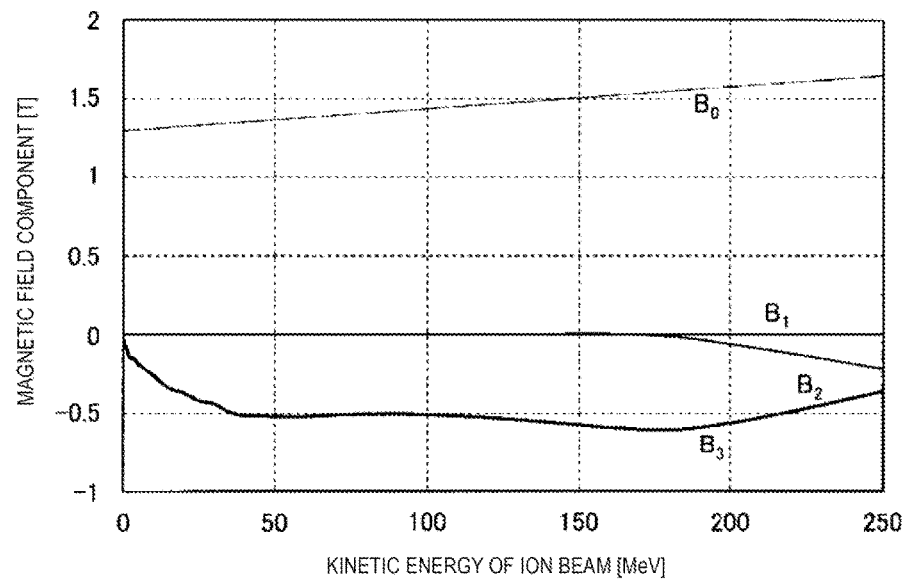
[Fig. 17]
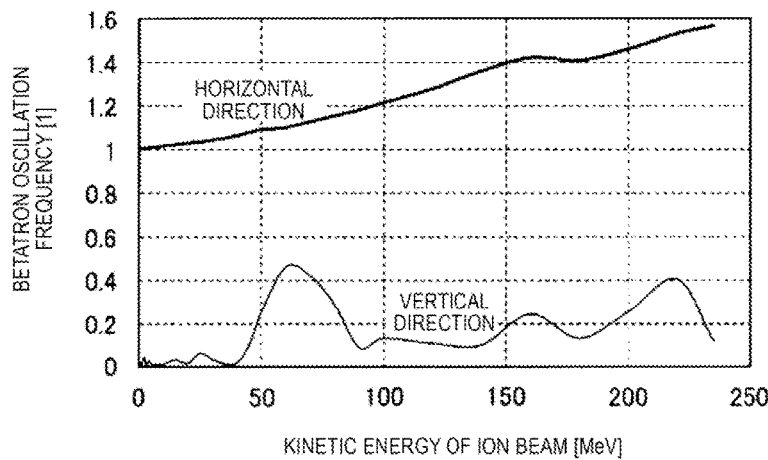

[Fig. 18]
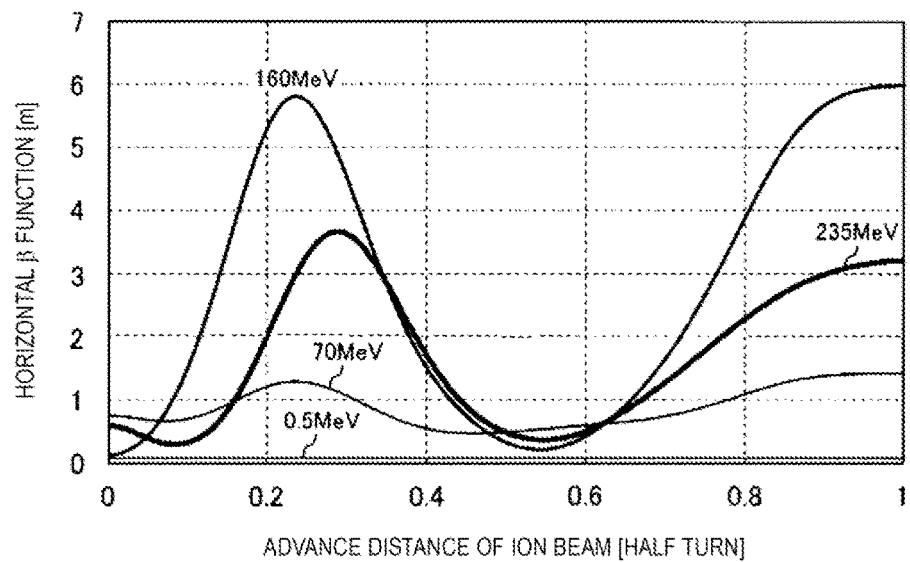
[Fig. 19]
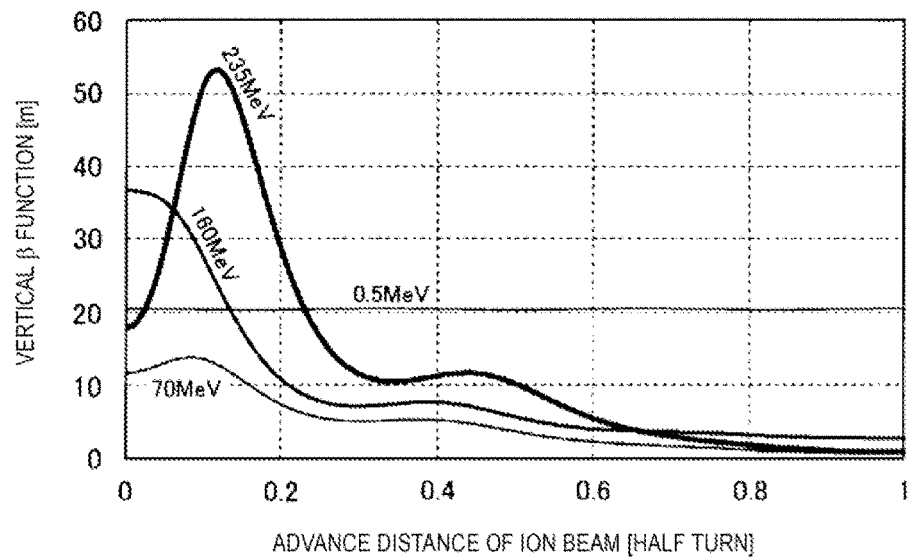

[Fig. 20]
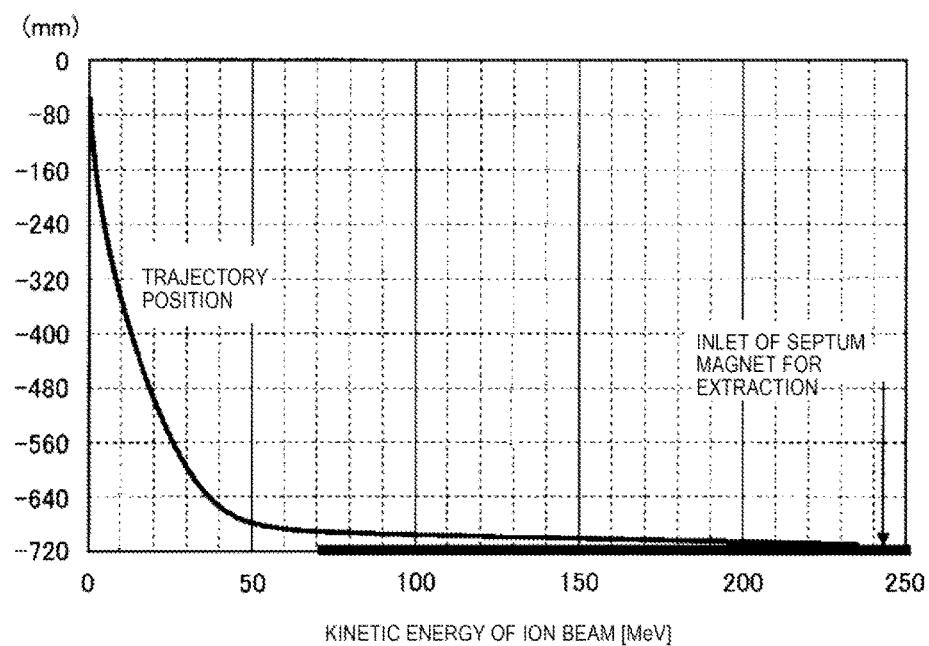
[Fig. 21]
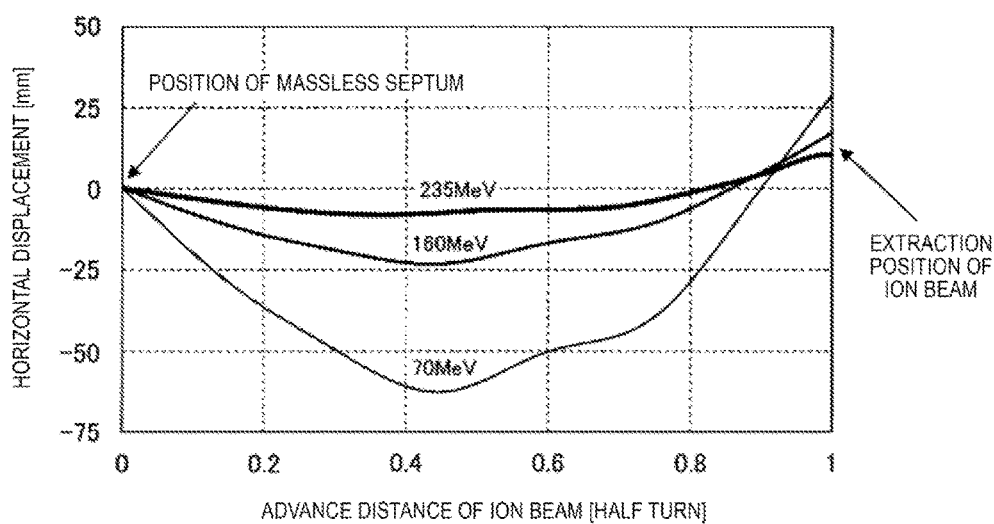

[Fig. 22]
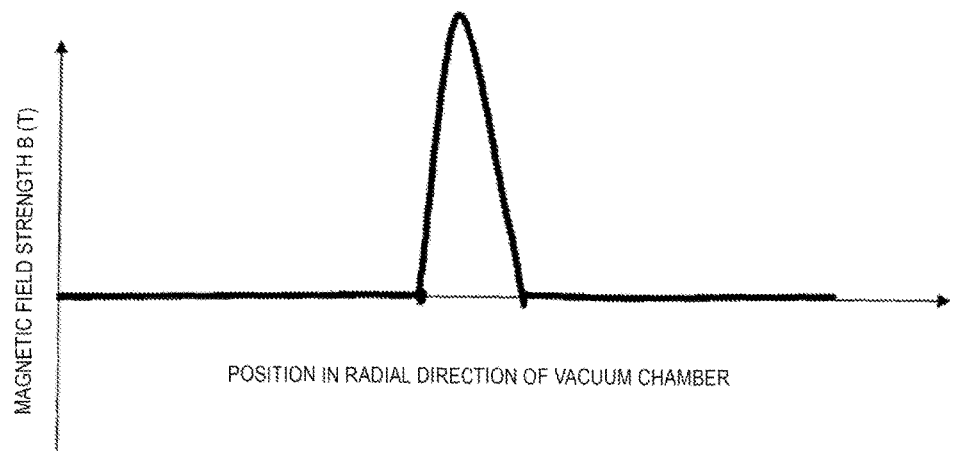

[Fig. 23]
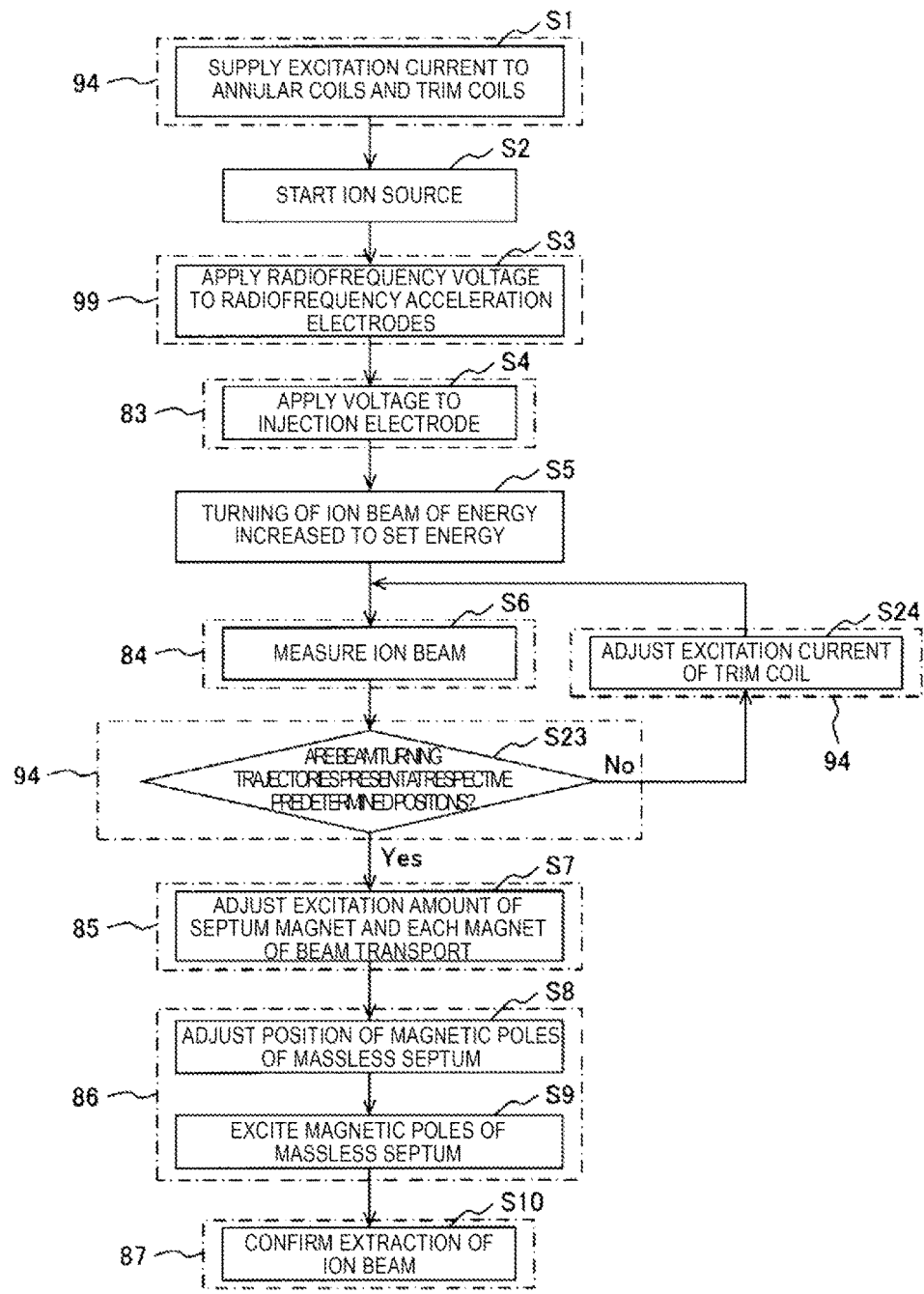

[Fig. 24]
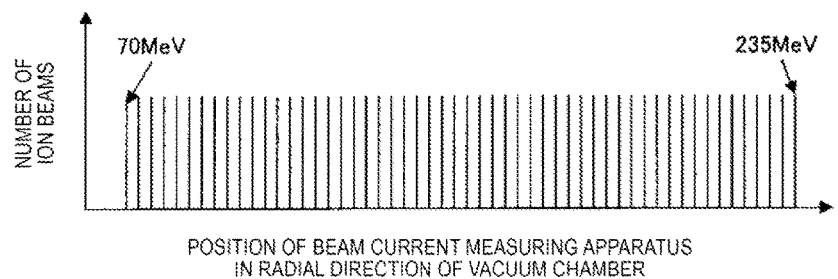

[Fig. 25]
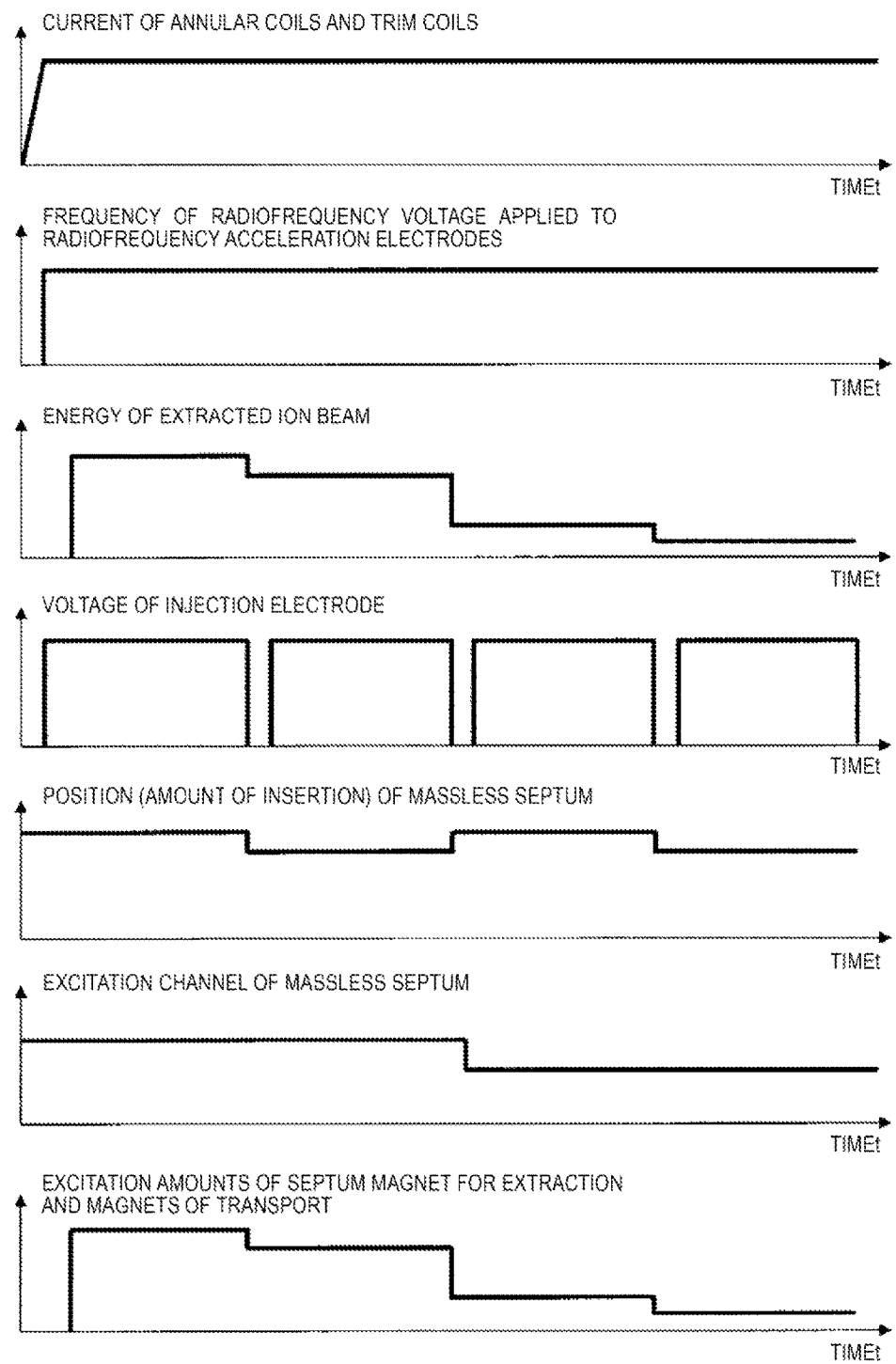

[Fig. 26]
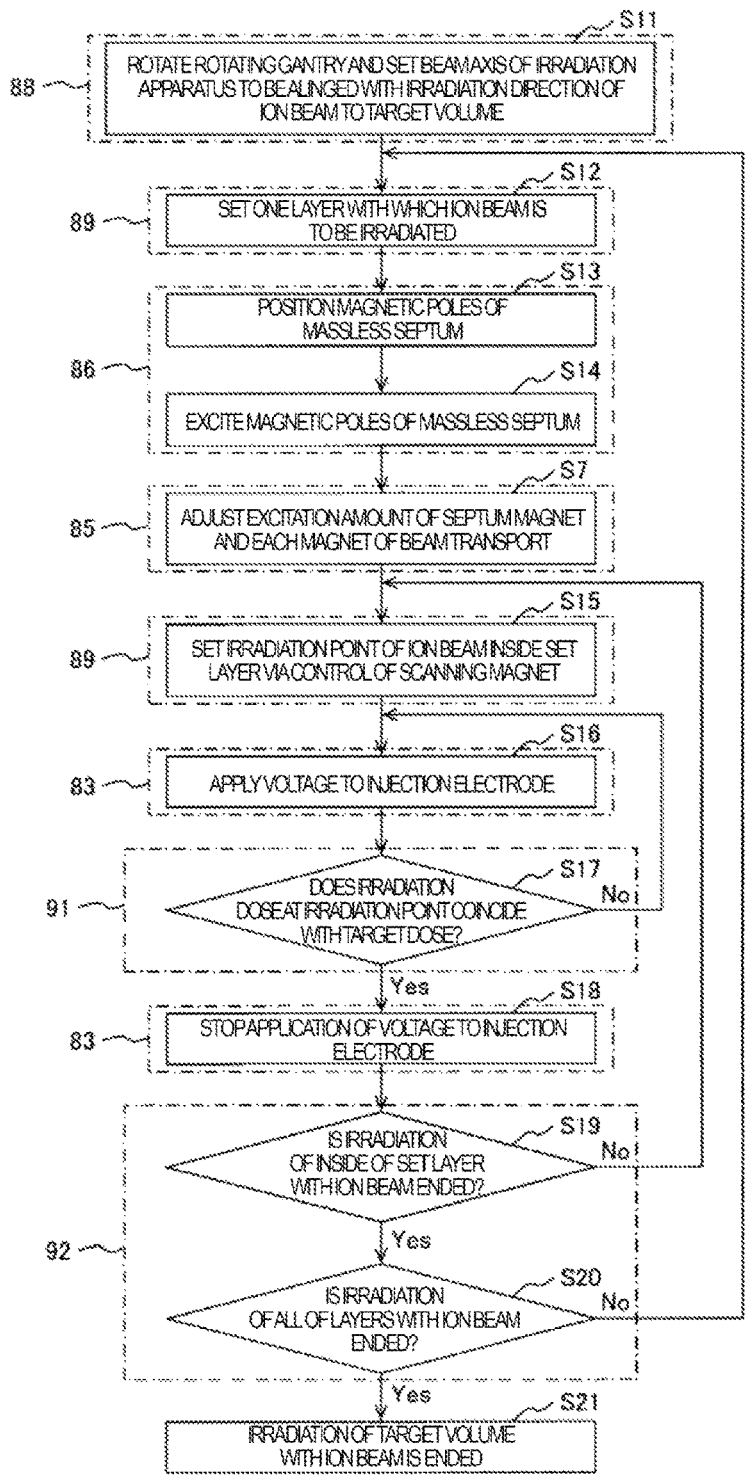

[Fig. 27]
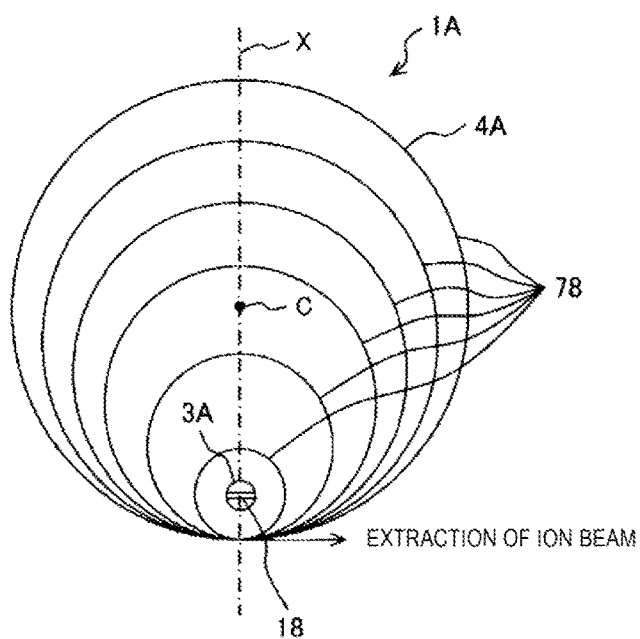

[Fig. 28]
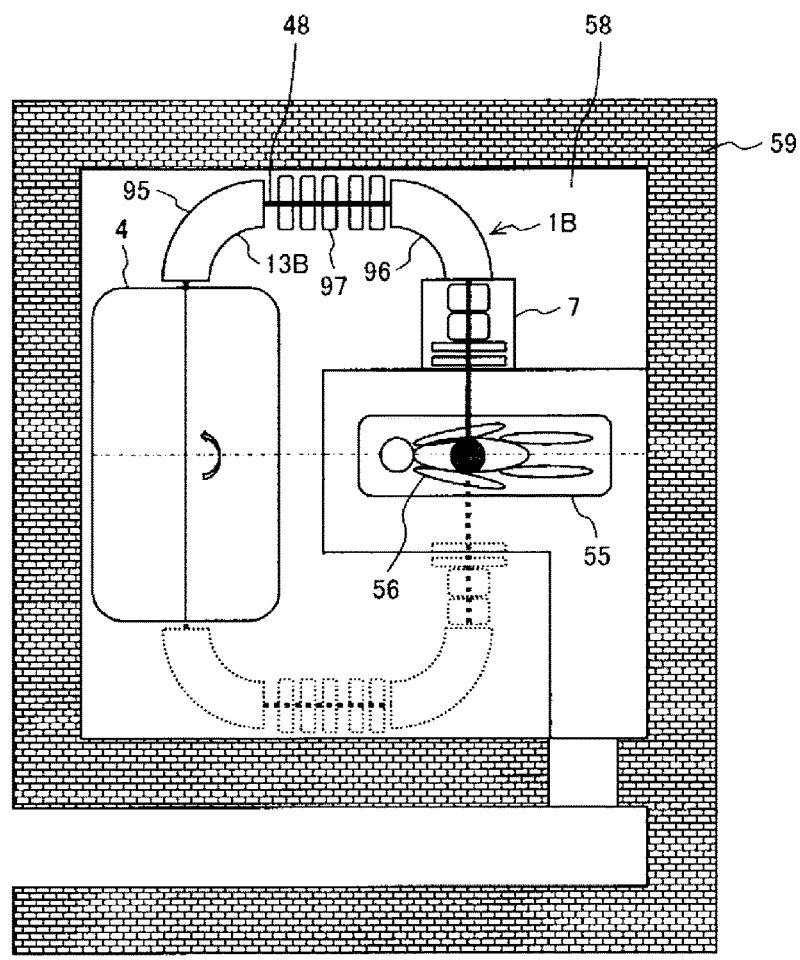

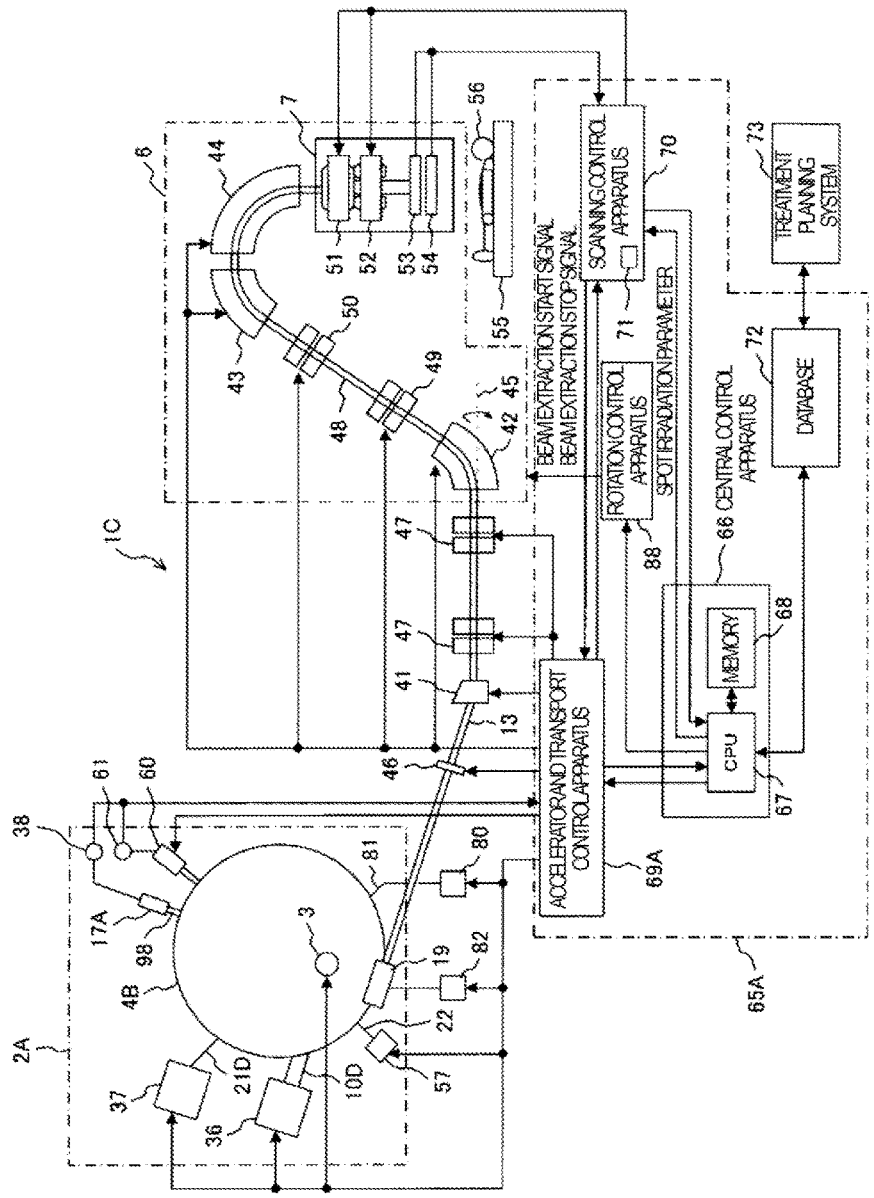
[Fig. 29]

[Fig. 30]
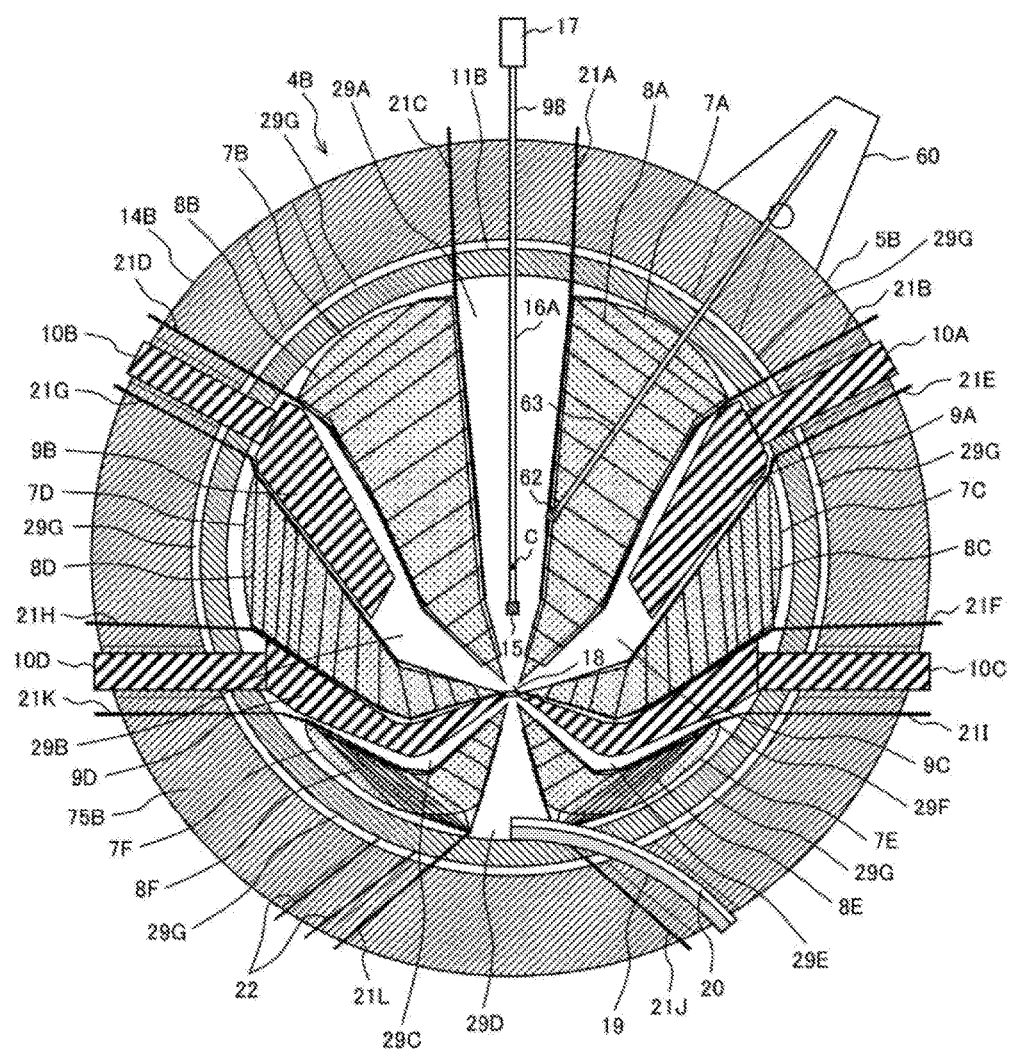

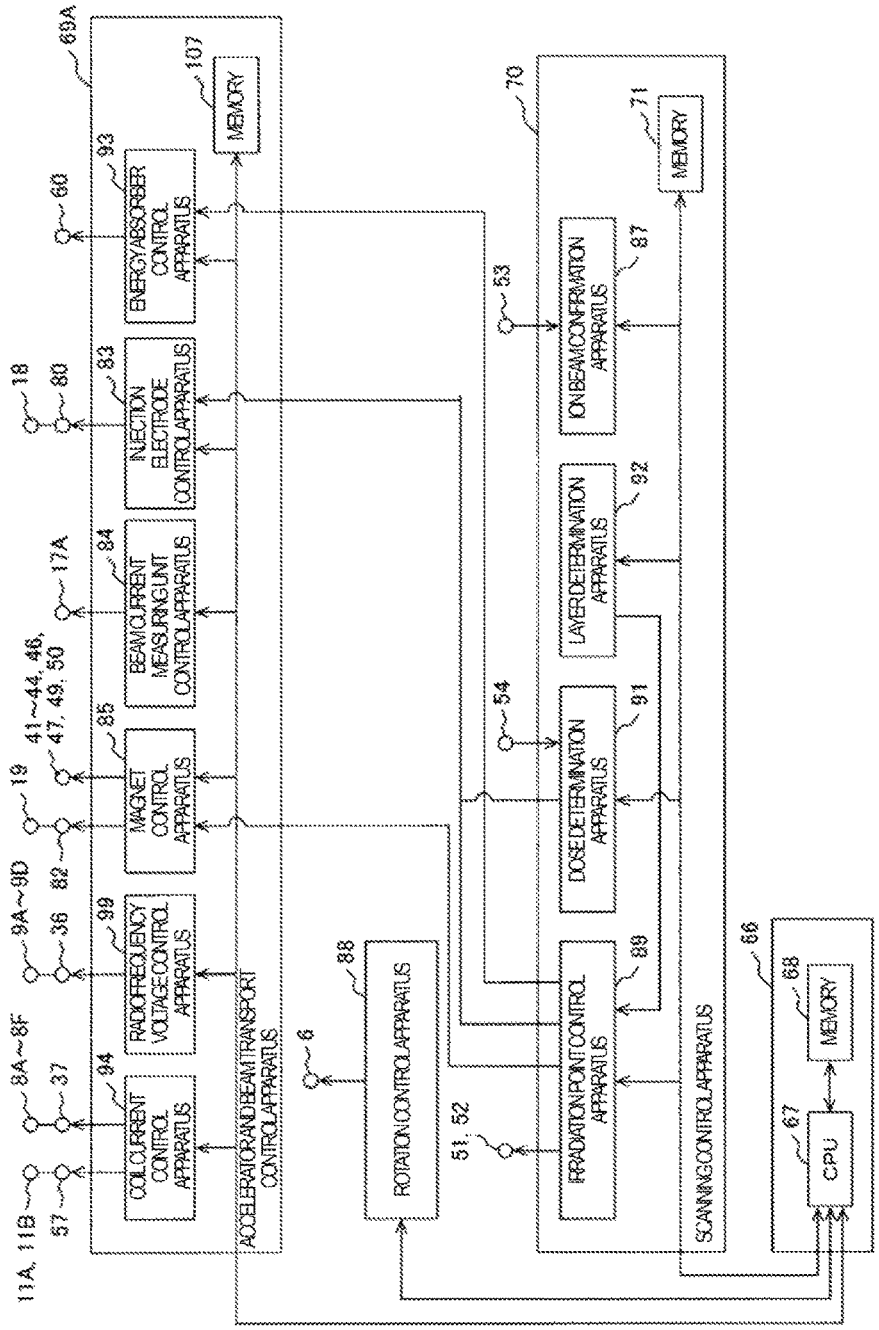
[Fig. 31]

[Fig. 32]
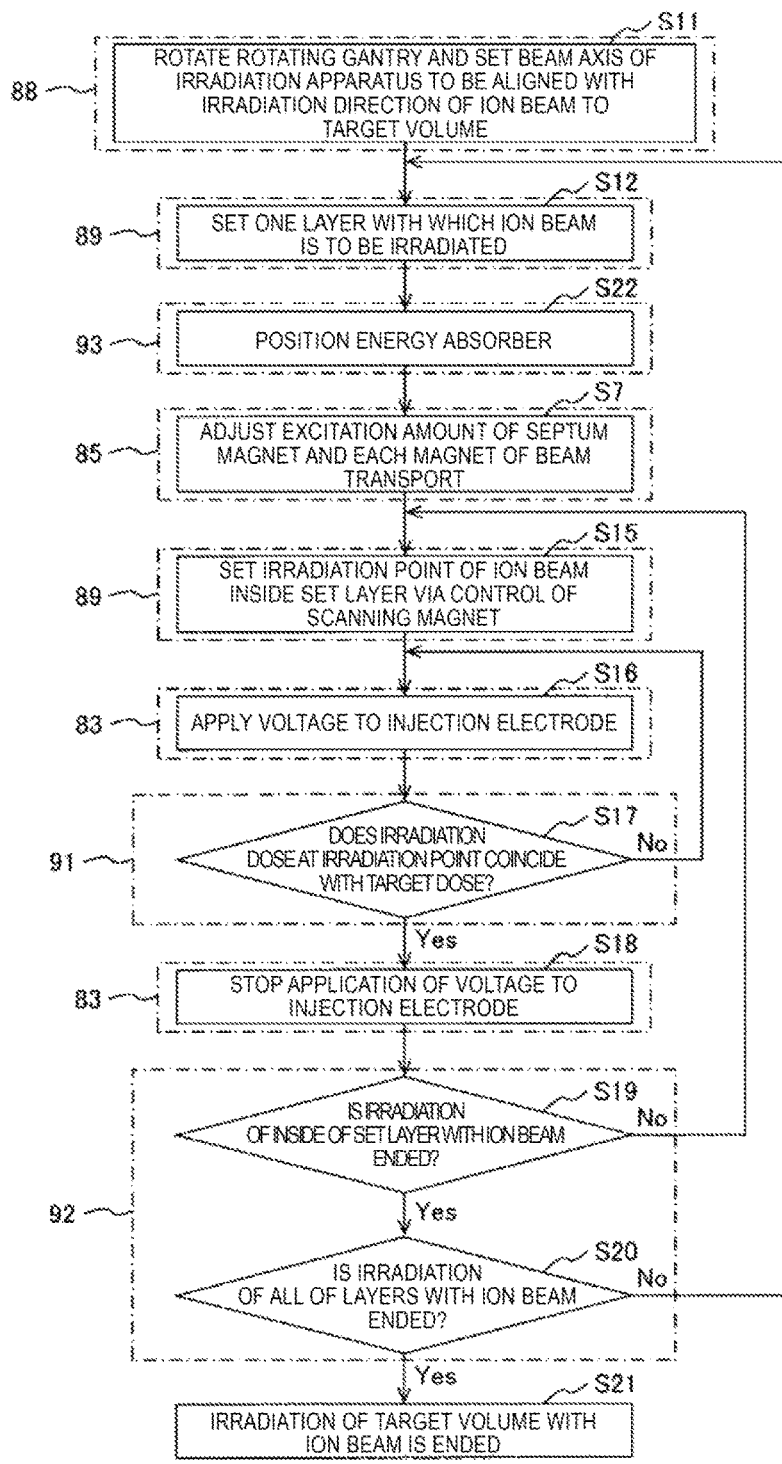

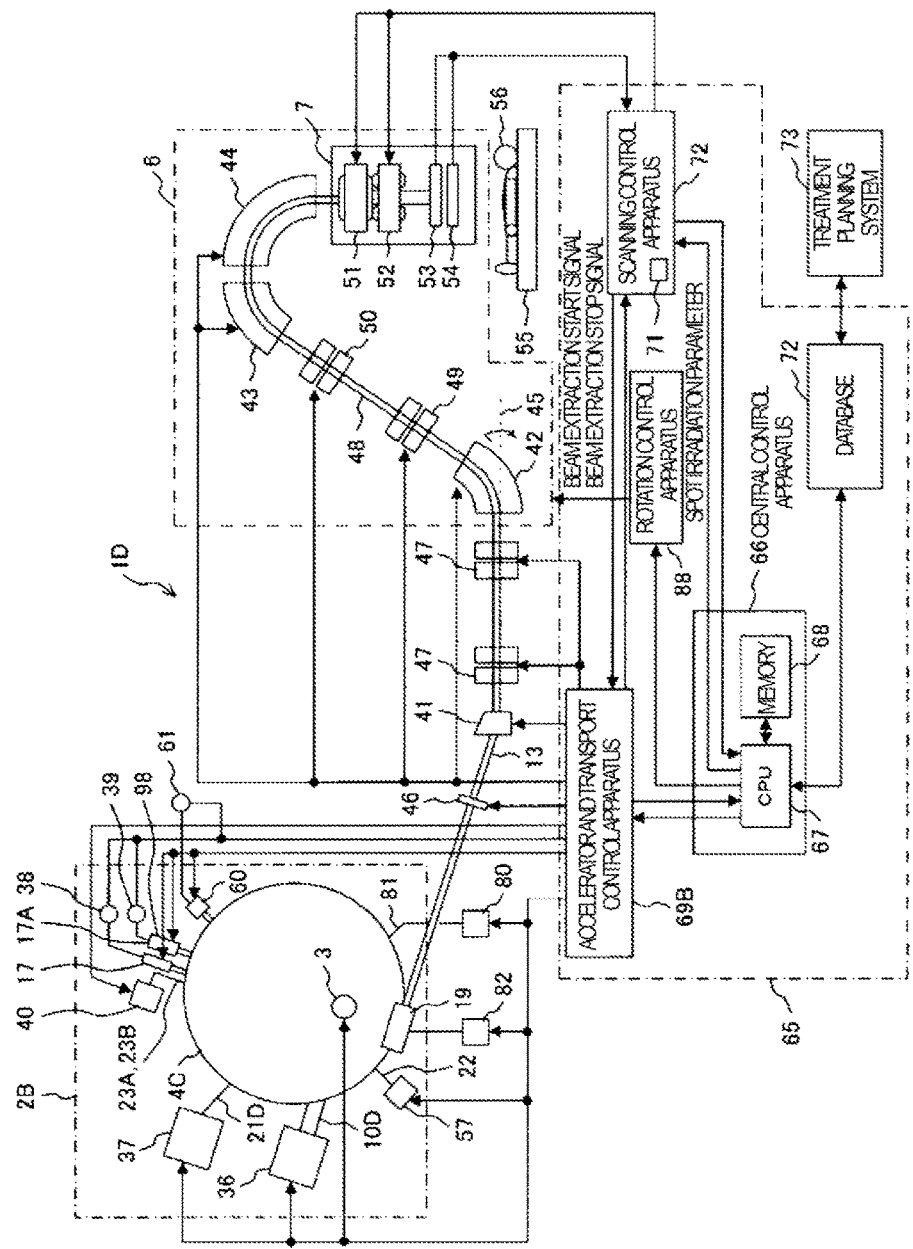
[Fig. 33]

[Fig. 34]
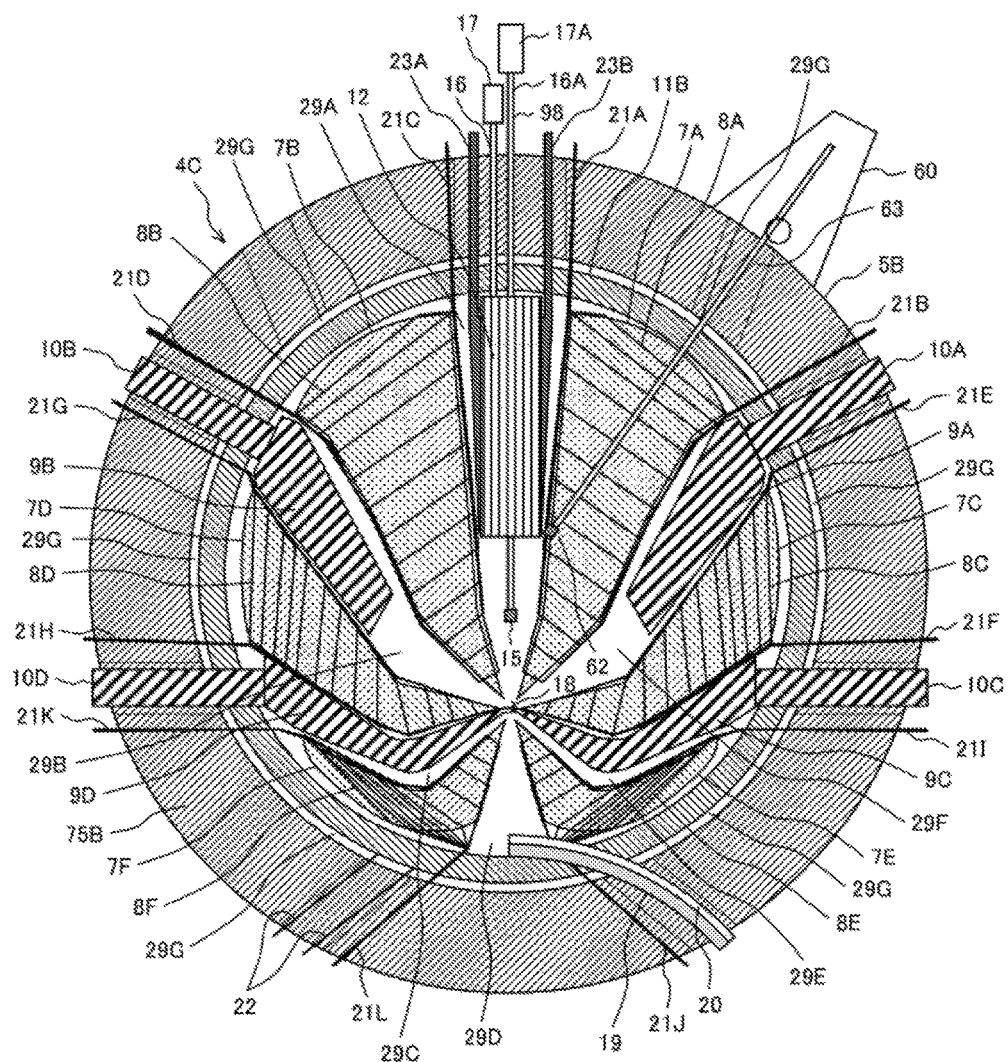

[Fig. 35]
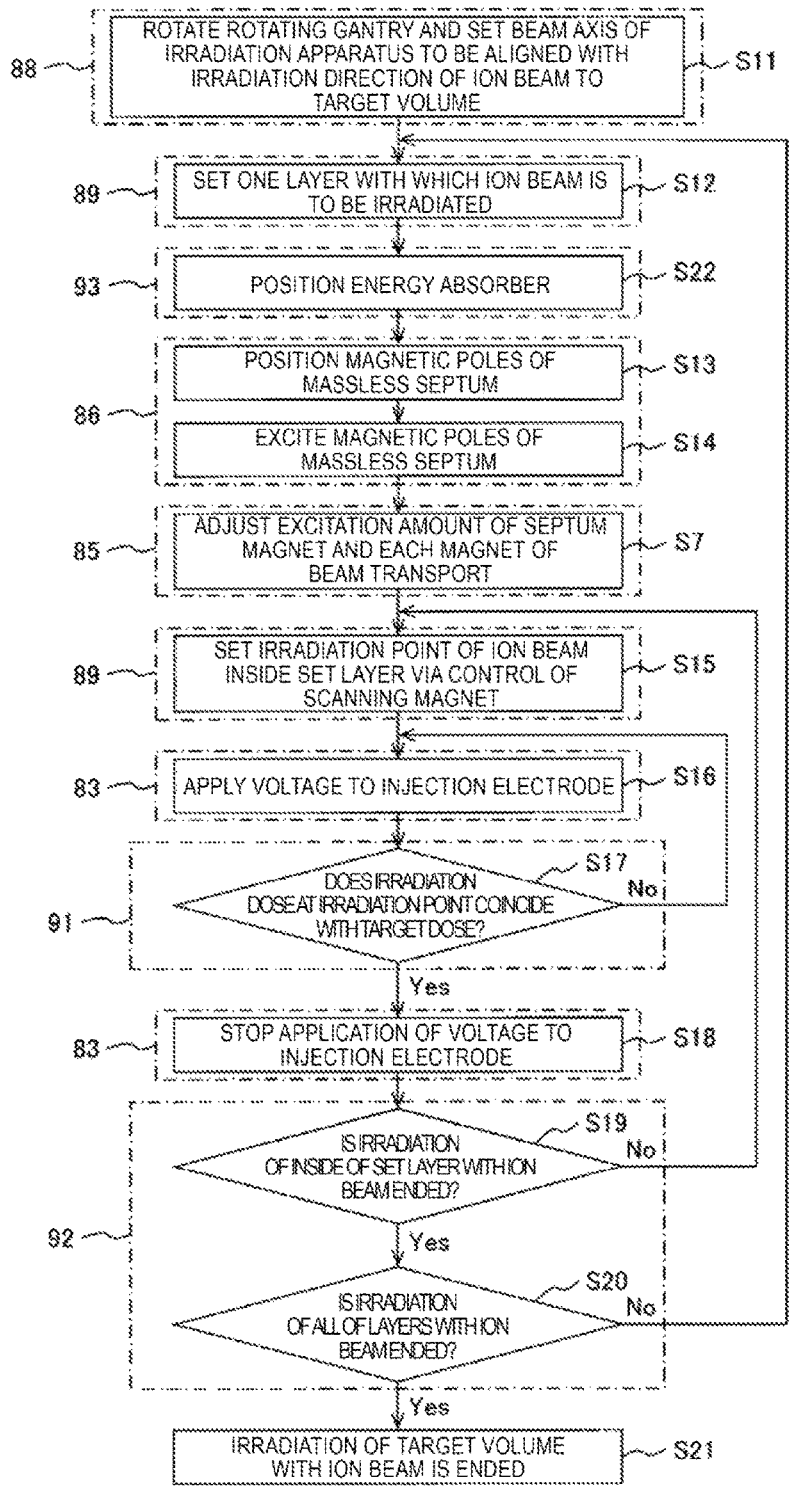

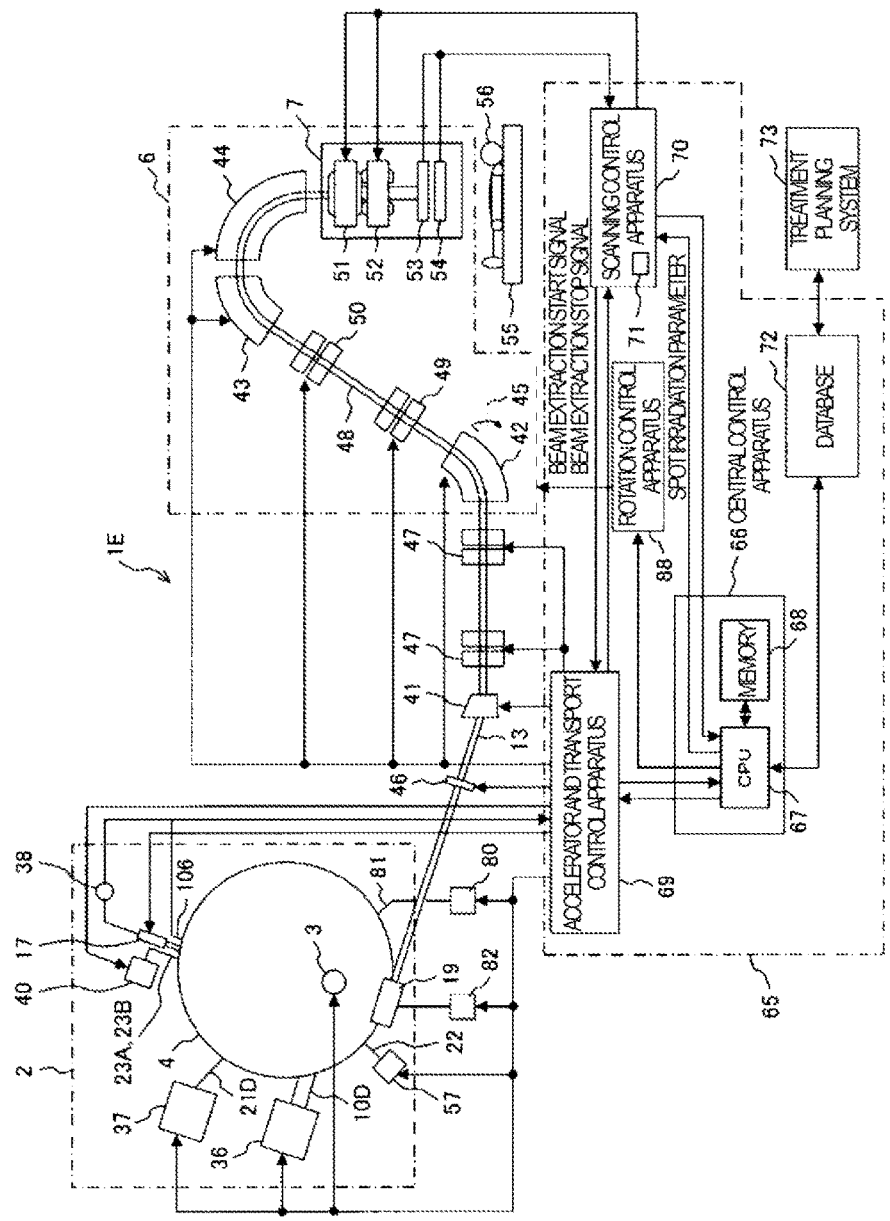
[Fig. 36]

[Fig. 37]
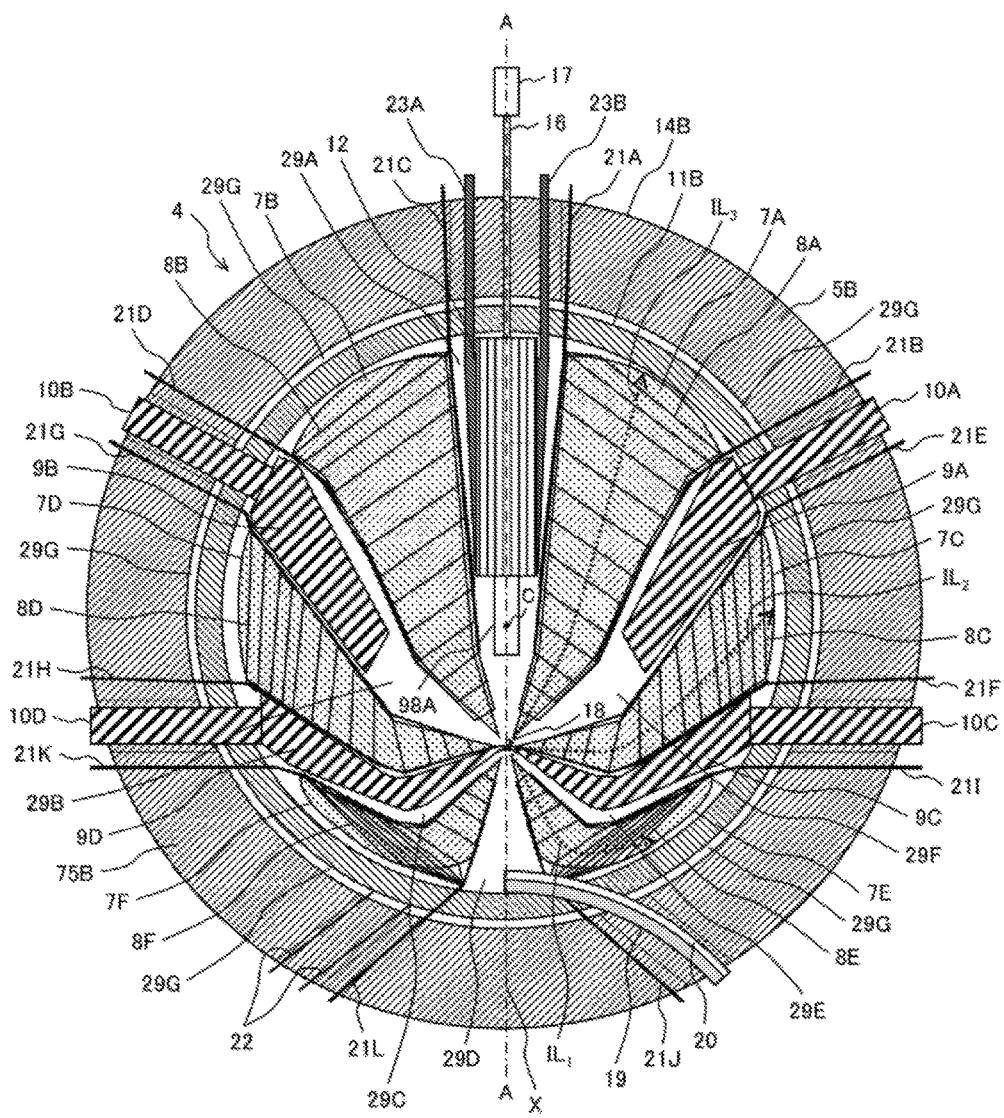

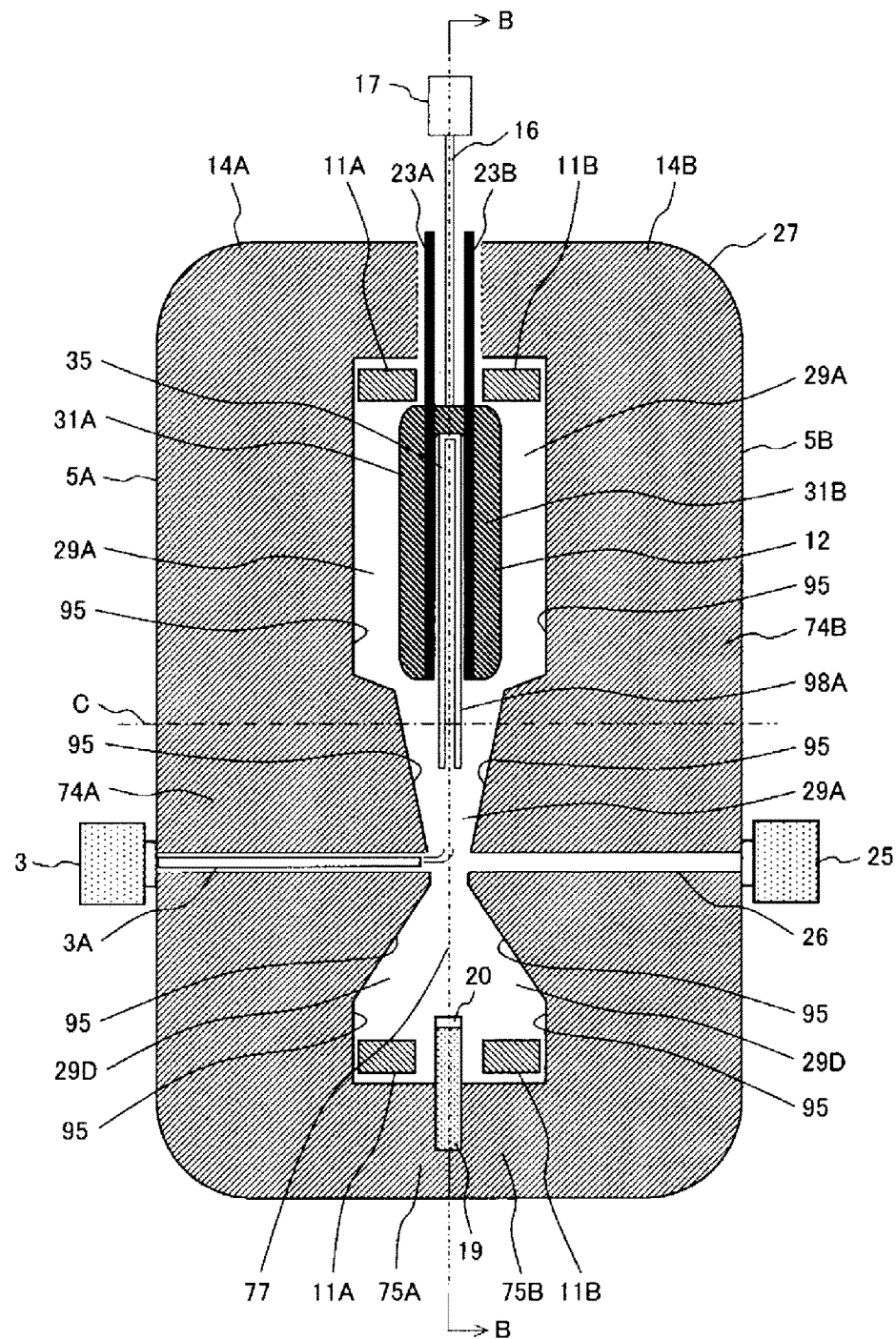
[Fig. 38]

[Fig. 39]
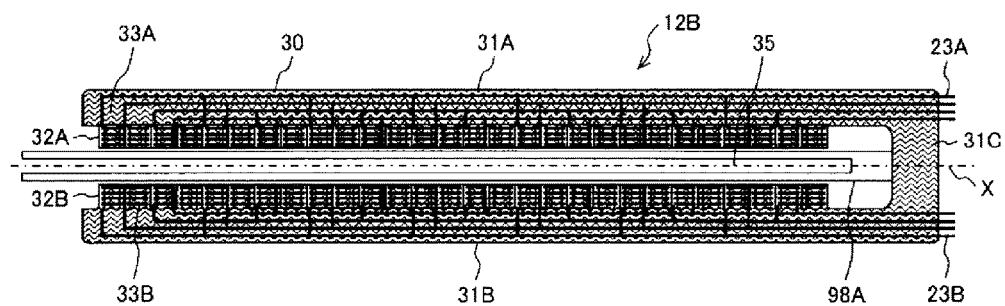

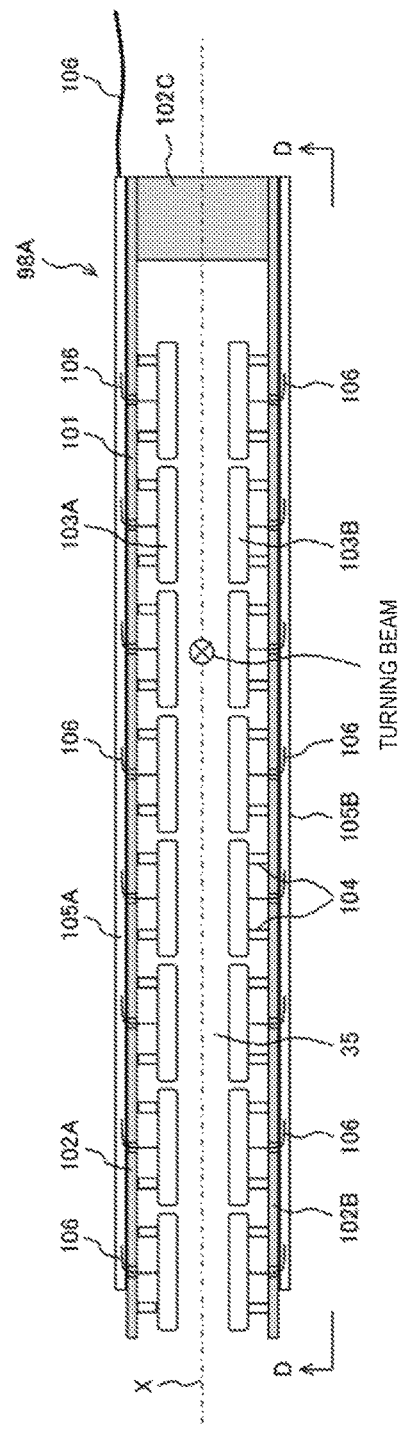
[Fig. 40]

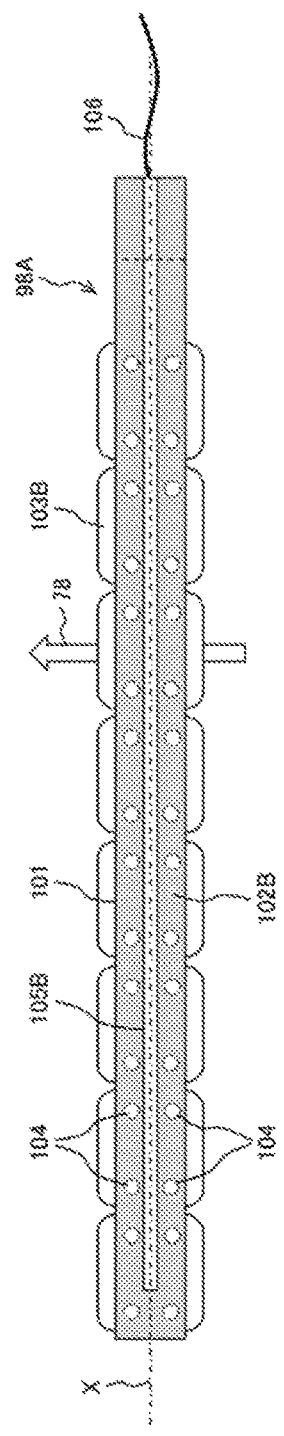
[Fig. 41]

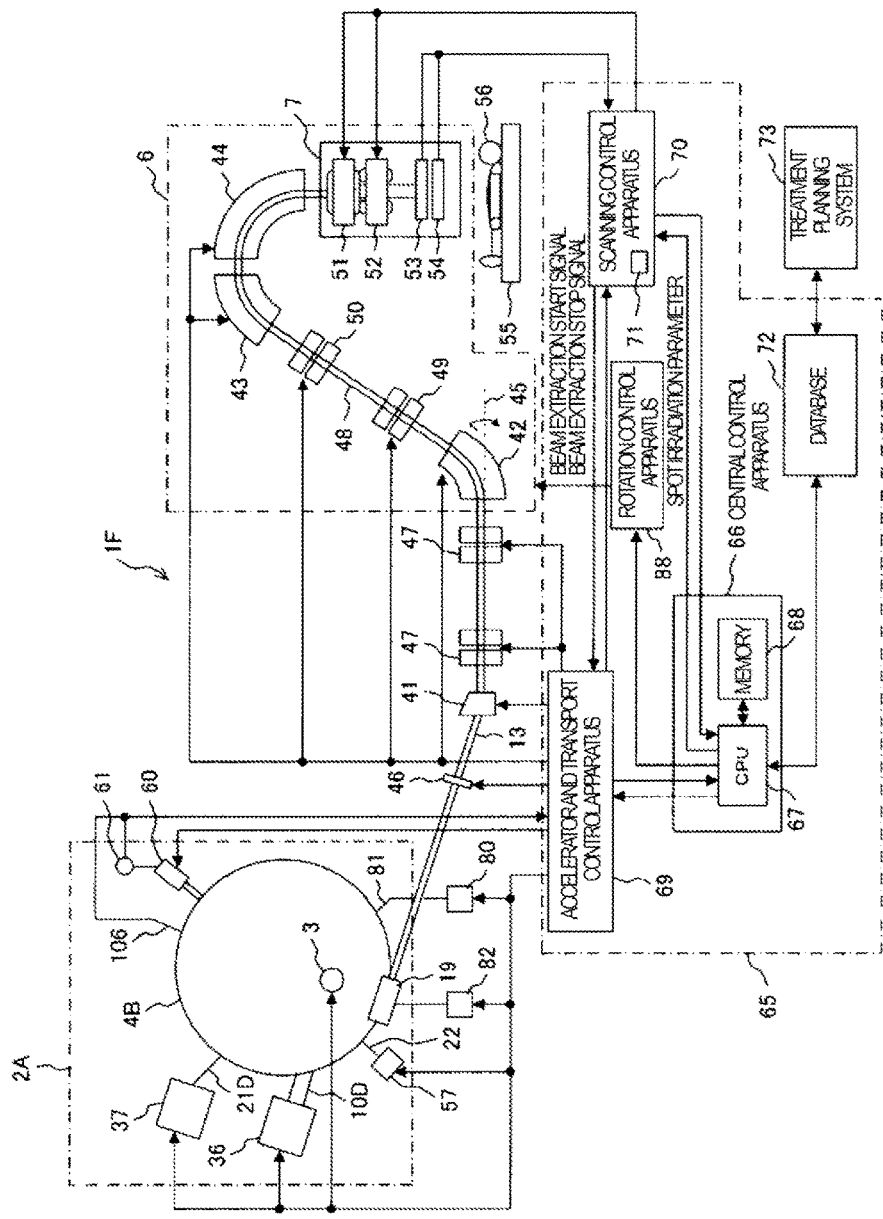
[Fig. 42]

[Fig. 43]
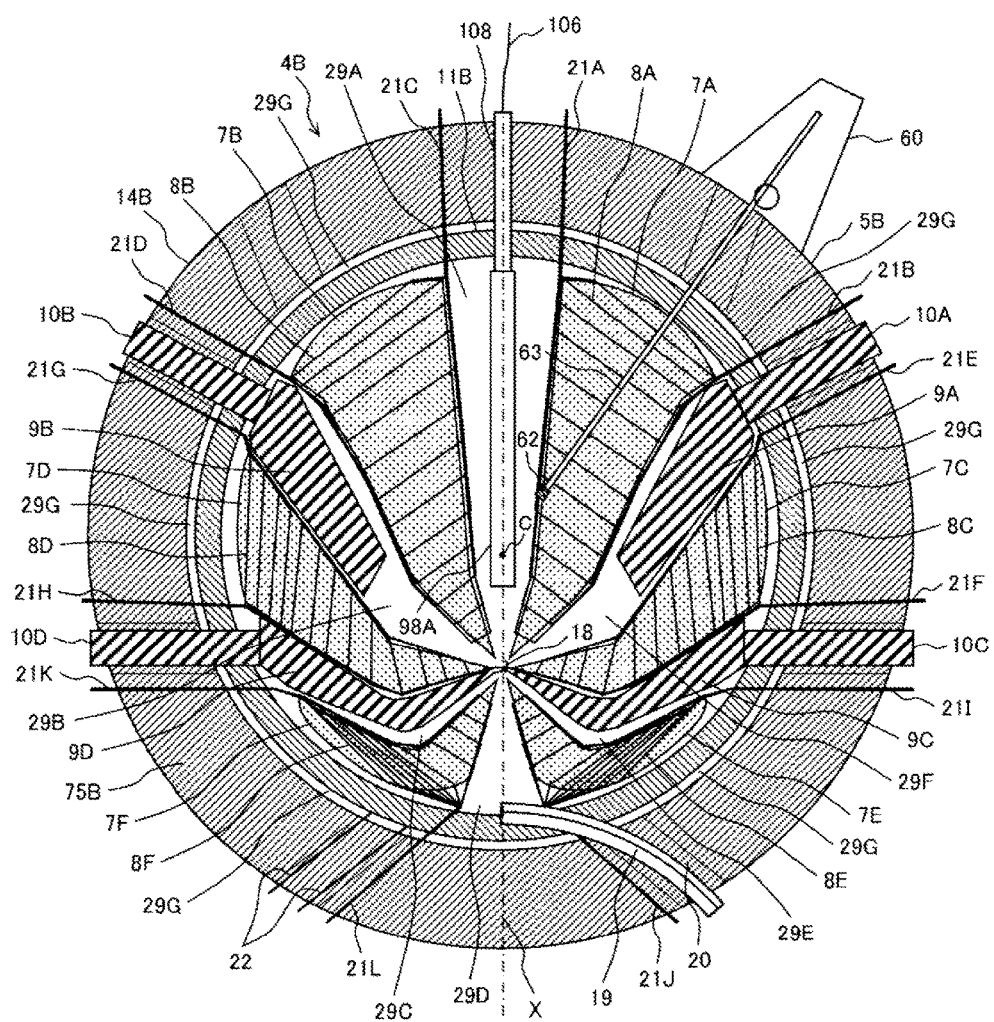

[Fig. 44]
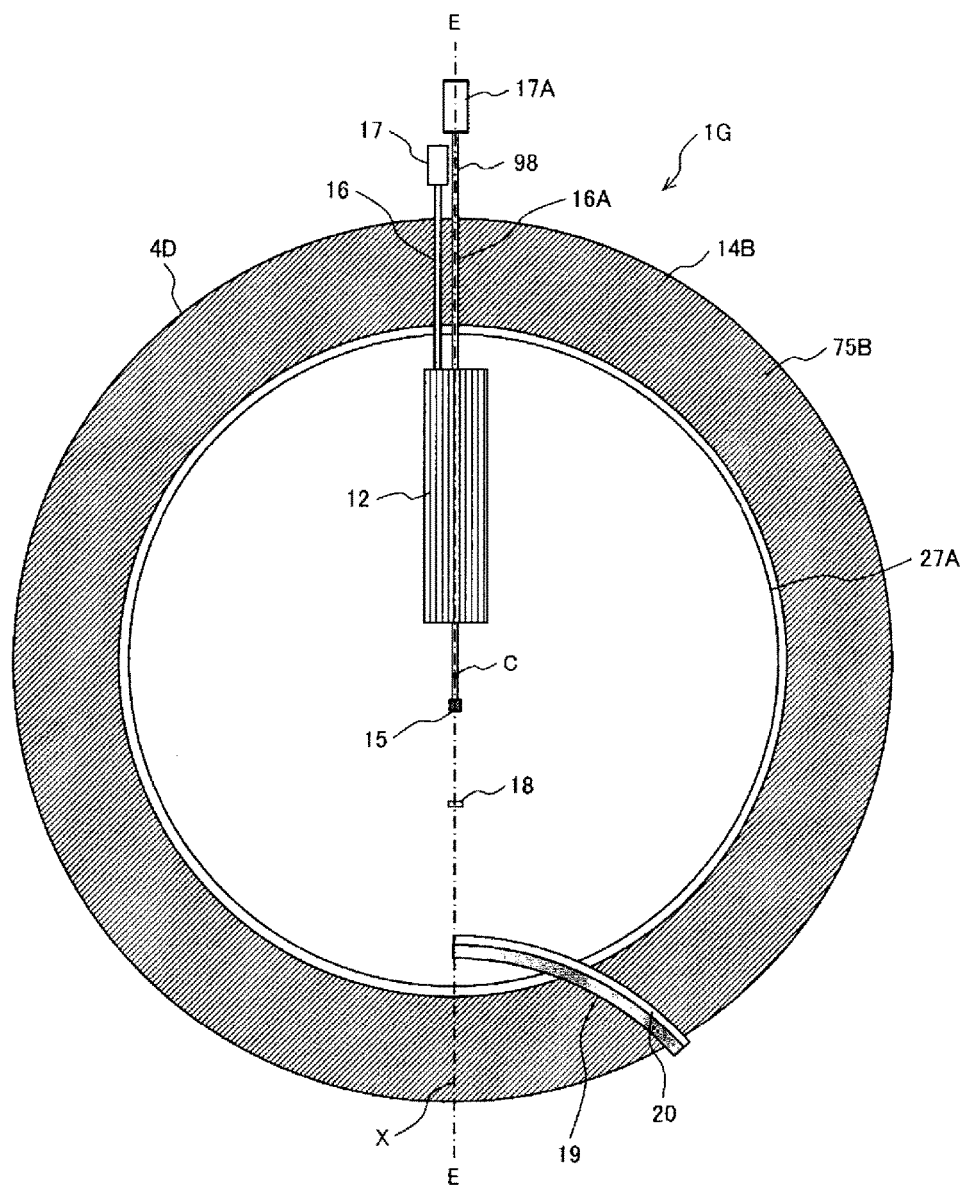

[Fig. 45]
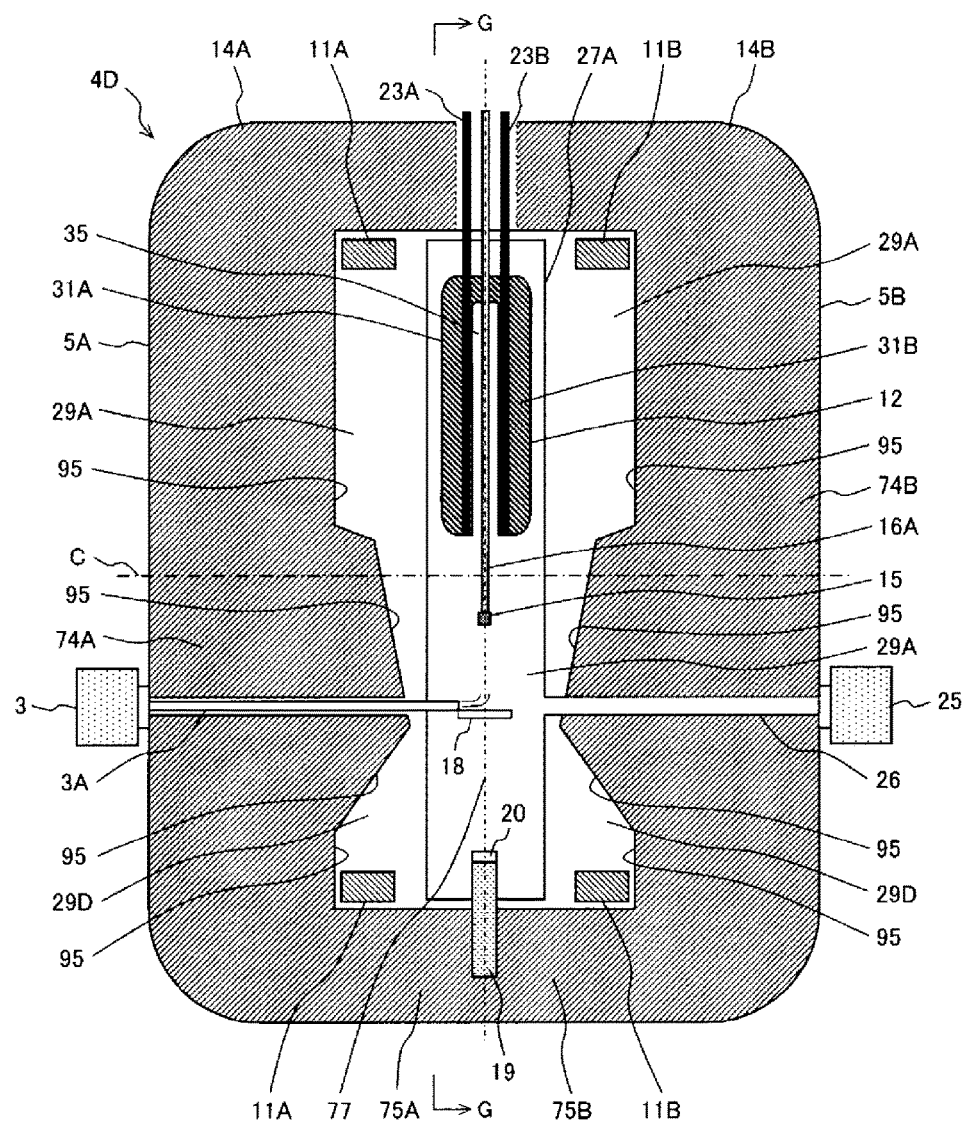

[Fig. 46]
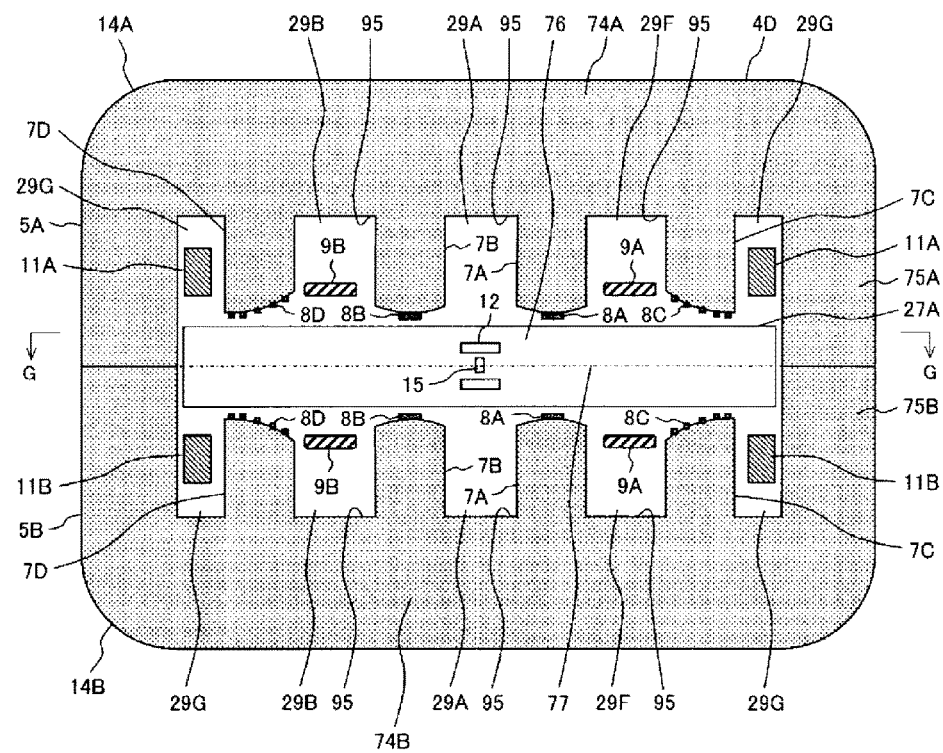
[Fig. 47]
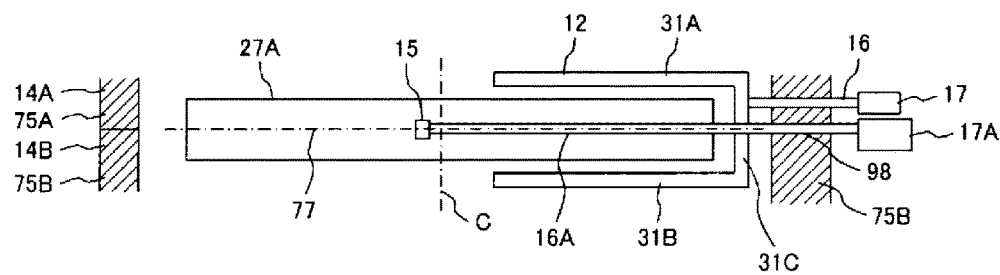

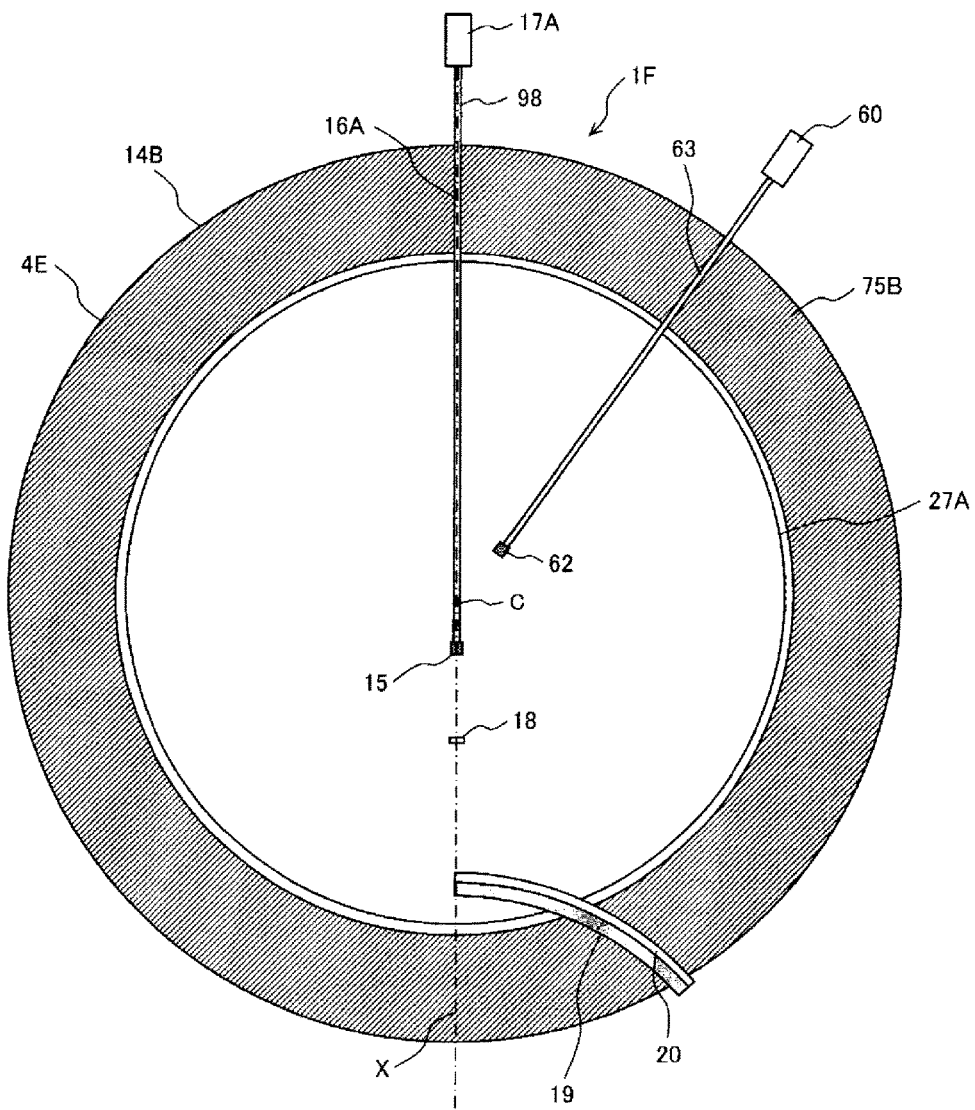
[Fig. 48]

ACCELERATOR AND PARTICLE BEAM IRRADIATION SYSTEM

TECHNICAL FIELD

The present invention relates to an accelerator and a particle beam irradiation system, particularly, to an accelerator and a particle beam irradiation system suitable for cancer treatment.

BACKGROUND ART

A particle beam irradiation system can be roughly classified into a particle beam irradiation system (for example, refer to PTL 1) including a synchrotron as an accelerator, and a particle beam irradiation system (for example, refer to PTL 2) including a cyclotron as an accelerator.

A particle beam irradiation system including a synchrotron includes an ion source; a linear accelerator; a synchrotron; a beam transport; a rotating gantry; and an irradiation apparatus. The synchrotron includes an annular beam duct, and the beam duct is provided with multiple bending magnets, multiple quadrupole magnets, a radiofrequency acceleration cavity, an extraction radiofrequency electrode, and an extraction deflector. The ion source is connected to the linear accelerator, and the linear accelerator is connected to the synchrotron. A portion of the beam transport, which is connected to an extraction port of the synchrotron, is installed in the rotating gantry, and communicates with the irradiation apparatus installed in the rotating gantry.

Ions (for example, protons or carbon ions) extracted from the ion source are accelerated by the linear accelerator. An ion beam generated by the linear accelerator is injected into the annular beam duct of the synchrotron. The ion beam turning through the beam duct is accelerated to a predetermined energy in the radiofrequency acceleration cavity to which a radiofrequency voltage is applied. A radiofrequency voltage is applied from a radiofrequency electrode of the extraction radiofrequency electrode to the ion beam which has turned around and reached the predetermined energy, thereby extracting the ion beam to the beam transport via the extraction deflector. A tumor volume of a patient on a treatment bed is irradiated with the ion beam from the irradiation apparatus. The rotating gantry rotates the irradiation apparatus such that a beam path of the irradiation apparatus coincides with an irradiation direction of the ion beam toward the target volume.

In a case where the target volume is divided into multiple layers in an irradiation direction of an ion beam, and each layer is scanned with an ion beam, a layer to which an ion beam has to reach is specified by changing the energy of the ion beam. As described above, the energy of an ion beam is adjusted by controlling the pattern of a radiofrequency voltage applied to the radiofrequency acceleration cavity, an excitation pattern of the quadrupole magnets, and an excitation pattern of the bending magnets. The scanning of the inside of each layer with an ion beam is controlled by adjusting an excitation current of an operation magnet provided in the irradiation apparatus.

A particle beam irradiation system including a cyclotron includes an ion source; a cyclotron; a beam transport; a rotating gantry; and an irradiation apparatus. The cyclotron includes a vacuum chamber formed of a pair of facing iron cores having a circular section; a radiofrequency acceleration apparatus; and an extraction magnet. The beam transport communicates with an extraction portion of the cyclotron in which the extraction magnet is disposed. The beam transport, the rotating gantry, and the irradiation apparatus of the particle beam irradiation system including a cyclotron have substantially the same structures of those of the particle beam irradiation system including a synchrotron.

In the particle beam irradiation system including a cyclotron, ions (for example, protons or carbon ions) extracted from the ion source are injected to the center of a section of the iron cores of the cyclotron, and are accelerated by the radiofrequency acceleration apparatus. An accelerated ion beam turns in a spiral pattern from the center of the iron cores toward an inner surface of a return yoke, and is extracted to the beam transport by the extraction magnet provided in a peripheral portion of the iron cores. A tumor volume of a patient on a treatment bed is irradiated with the extracted ion beam from the irradiation apparatus via the beam transport.

As described above, in a case where the target volume is divided into multiple layers, and each layer is scanned with an ion beam using the particle beam irradiation system including a cyclotron, the energy of an ion beam extracted to the beam transport is adjusted by using a degrader provided in the beam transport. The degrader is formed of a single metal plate or a combination of multiple metal plates having different thicknesses. The degrader reduces the energy of an ion beam passing through the degrader, that is, adjusts the energy of an ion beam with which the target volume is irradiated. Since the energy of an ion beam accelerated by the cyclotron typically is constant, the energy of an ion beam is increased to the maximum energy required for cancer treatment by the cyclotron, the energy is dampened and adjusted to a predetermined energy when the ion beam penetrates through a metal plate provided in the degrader.

PTL 3 discloses a cyclotron that is used in this type of particle beam irradiation system and is capable of improving ion beam extraction efficiency. The cyclotron includes a pair of magnetic poles between which ion beam turning trajectories are formed, which includes multiple protrusions and multiple recesses which are alternately disposed in a circumferential direction, and by which hill regions are formed interposed between the protrusions and valley regions are formed interposed between the recesses along the turning trajectories; dee electrodes which are provided in the valley regions; and an acceleration cavity that is disposed in at least one valley region other than the valley regions in which the dee electrodes are provided, and on an outer circumferential side in a radial direction of the ion beam turning trajectories, and accelerates an ion beam. In the cyclotron in which the acceleration cavity is provided in addition to the dee electrodes so as to accelerate an ion beam, a turn separation is increased by an increase in the amount of energy increase per one turn of an ion beam, and ion beam extraction efficiency is improved.

PTL 4 discloses a charged particle beam irradiation method in which a tumor volume is divided into multiple layers from a body surface of a patient in an irradiation direction of an ion beam, and multiple irradiation points inside each layer are irradiated with ion beams by scanning the multiple irradiation points with fine ion beams. An ion beam is moved to an adjacent irradiation point inside a layer by controlling a scanning magnet provided in an irradiation apparatus. An ion beam is moved from a distal layer to a proximal layer by changing the energy of an ion beam. A Bragg peak (to be described later) of an ion beam reaches a distal position of a target volume by the extent of the increase in the energy of the ion beam. In a case where the patient is irradiated with an ion beam, a dose distribution illustrated in FIG. 3 of PTL 4 is obtained in a depth direction from the body surface of the patient, a dose reaches the maximum value at a Brigg peak, and the dose distribution is rapidly decreased at a depth at which the Bragg peak is exceed. Cancer treatment via ion beams uses properties in which a dose reaches the maximum value at a Bragg peak and is rapidly decreased at a depth at which the Bragg peak is exceeded.

In a particle beam irradiation system disclosed in PTL 5, a circular accelerator which extracts ion beams is attached to a rotating frame which rotates in a vertical position, and a beam transport chamber is provided to guide ion beams, which are extracted from the accelerator, to a treatment room. The beam transport chamber is connected to an extraction port of the accelerator. The beam transport chamber extends in a radial direction of the accelerator, is bent toward a horizontal direction, and reaches a position directly above the treatment room, and thereafter, the beam transport chamber is bent downward. A beam delivery system is attached to a tip end portion of the beam transport chamber. The treatment room is formed inside a radiation enclosure, and a patient to be irradiated with ion beams lies on a treatment bed installed inside the treatment room. A side wall of the radiation enclosure is disposed between the accelerator and the treatment room. A target volume of the patient on the treatment bed is irradiated with ion beams which are extracted from the circular accelerator and transported via the beam transport chamber and the beam delivery system. In order to change an irradiation direction of an ion beam, the direction of the beam delivery system is changed by rotating the accelerator via rotation of the rotating frame, and turning the beam transport chamber and the beam delivery system around a rotational center of the accelerator.

CITATION LIST

Patent Literature

PTL 1: JP-A-2004-358237
PTL 2: JP-A-2011-92424
PTL 3: JP-A-2014-160613
PTL 4: JP-A-10-118204
PTL 5: Japanese Patent No. 3472657
PTL 6: JP-A-2006-239403

SUMMARY OF INVENTION

Technical Problem

The particle beam irradiation system using a synchrotron is capable of generating multiple ion beams of different energies in the synchrotron, and changing the energies of the ion beams extracted from the synchrotron. In contrast, the particle beam irradiation system using a synchrotron requires the multiple bending magnets and the multiple quadrupole magnets, it is not easy to reduce the size of the synchrotron to a certain size or smaller. Ion beams are intermittently extracted from a synchrotron, and the amount of extraction of ion beams is small.

In contrast, a cyclotron is capable of continuously extracting ion beams, and the amount of extraction of ion beams is large. The energy of an ion beam generated in the cyclotron is constant, and the cyclotron is not capable of extracting ion beams of energies lower than the maximum energy. For this reason, in a case where ion beams of low energies are required, for example, in a case where one layer of a target volume is irradiated with ion beams, it is necessary to adjust the energies of ion beams via the degrader provided in the beam transport such that the ion beams reach that layer. The use of the degrader to adjust the energy of an ion beam causes problems such as an increase in the beam size of an ion beam caused by the degrader, a reduction in the number of ions penetrating through the metal plates of the degrader, and an increase in radioactive waste.

For this reason, a proton beam therapy system is desirable to be able to continuously extract ion beams of different energies and to improve ion beam extraction efficiency.

An object of the present invention is to provide an accelerator and a particle beam irradiation system which are capable of efficiently extracting ion beams of different energies.

Solution to Problem

According to characteristics of the present invention, in order to achieve this object, an accelerator includes: an annular coil; a radiofrequency acceleration apparatus configured to accelerate ion beams on multiple annular beam turning trajectories; a beam extraction path configured to extract the accelerated ion beams to an outside; and a beam separation apparatus configured to separate the ion beams from the beam turning trajectories at multiple positions in a radial direction of the annular coil.

Since the accelerator includes the beam separation apparatus, it is possible to separate the ion beams of different energies from the beam turning trajectories at the multiple positions in the radial direction of the annular coil. It is possible to efficiently extract the respective ion beams of the different energies.

(A1) Hereinafter, a more preferable configuration of an accelerator, in which an ion injection portion, into which ions are supplied from an ion source, is disposed at a position that is different from that of the center of gravity or a central axis of a main coil in a radial direction, each of a pair of iron cores extends radially from the ion injection portion at the periphery of the ion injection portion, forms multiple magnetic poles, a tip end of each of which faces the ion injection portion, and forms multiple recesses which extend radially from the ion injection portion at the periphery of the ion injection portion, the magnetic poles and the recesses are alternately disposed at the periphery of the ion injection portion, and the main coil surrounds the multiple magnetic poles and the multiple recesses which are disposed inside each of the iron core, will be described.

(A2) Preferably, according to (A1), in each of the pair of iron cores, in regions which are positioned on a plane perpendicular to a central axis of the main coil and on both sides of a straight line that connects an inlet of a beam extraction path to the central axis of the main coil, each of radiofrequency acceleration electrodes is disposed between magnetic poles which are adjacent to each other in a circumferential direction of the main coil among the multiple magnetic poles disposed on each of both sides of the straight line and on the plane perpendicular to the central axis. Preferably, respective tip ends of the radiofrequency acceleration electrodes face the ion injection portion, and each of the radiofrequency acceleration electrodes has bent points. Preferably, a portion of each of the radiofrequency acceleration electrodes between the bent points of the radiofrequency acceleration electrode and an end surface of the radiofrequency acceleration electrode facing the main coil is bent toward a first recess which is one of recesses positioned between magnetic poles adjacent to each other in the circumferential direction of the main coil and which is present 180° opposite to the inlet of the beam extraction path.

(A3) Preferably, according to (A1), a beam current measuring apparatus, which is disposed in the first recess, includes a beam current measuring unit that is disposed in the first recess, in a beam turning region formed between the pair of iron cores, and a trajectory plane on which beam turning trajectories are formed and which is perpendicular to the central axis of the main coil; a movement apparatus that moves the beam current measuring unit on the trajectory plane in the radial direction of the main coil; and a position detector that detects the position of the beam current measuring unit to be moved on the trajectory plane.

(A4) Preferably, according to (A1), the accelerator includes a first control apparatus (for example, a coil current control apparatus) that controls an excitation current supplied to each of trim coils which are respectively attached to the multiple magnetic poles, when a beam turning trajectory, which is measured by the beam current measuring apparatus disposed in the first recess, is not positioned at a predetermined position.

(B1) Hereinafter, a more preferable configuration of an accelerator, which includes a beam separation apparatus that separates ion beams from respective beam turning trajectories at multiple positions in a radial direction of a main coil, will be described.

(B2) Preferably, according to (B1), the accelerator further includes a pair of iron cores that are joined together in a state where a beam turning region, on which beam turning trajectories, along which ion beams respectively turn, are formed, is interposed therebetween; main coils which are respectively disposed inside the pair of iron cores; and a beam path that passes through the iron core and is an extraction port of an ion beam, in which an ion injection portion, to which ions are supplied from an ion source and around which the beam turning region is formed, is disposed at a position that is different from the center of the main coil in the radial direction.

(B3) Preferably, according to (B2), multiple magnetic poles and multiple recesses are formed in each of the pair of iron cores, are alternately disposed to surround the ion injection portion, and a bending magnet apparatus which is a beam separation apparatus is disposed in one recess to face the ion injection portion.

(B4) Preferably, according to (B3), the bending magnet apparatus is disposed in a first recess which is one of the recesses and is positioned 180° opposite to an inlet of a beam extraction path relative to the ion injection portion.

(B5) Preferably, according to (B4), a movement apparatus is provided to move the bending magnet apparatus.

(B6) Preferably, according to (B3), a beam current measuring apparatus, which is disposed in the recess in which the bending magnet apparatus is disposed, includes a beam current measuring unit that is disposed in the recess, in the beam turning region formed between the pair of iron cores, and a trajectory plane on which beam turning trajectories are formed and which is perpendicular to a central axis of the main coil; a movement apparatus that moves the beam current measuring unit on the trajectory plane in the radial direction of the main coil; and a position detector that detects the position of the beam current measuring unit to be moved on the trajectory plane.

(B7) Hereinafter, a more preferable configuration of a particle beam irradiation system, which includes the accelerator in (B2) and an irradiation apparatus that outputs ion beams extracted from the accelerator, will be described.

(B8) Preferably, according to (B7), the particle beam irradiation system includes a rotation apparatus that rotates the irradiation apparatus; a fourth control apparatus (for example, a rotation control apparatus) that controls rotation of the rotation apparatus so as to set a beam axis of the irradiation apparatus to be aligned with an irradiation direction of ion beams to a target for beam irradiation; and a first control apparatus (for example, a massless septum control apparatus) that, in order to irradiate a layer of multiple layers, into which the target for beam irradiation is divided in the irradiation direction, with an ion beam of an energy required to reach the layer, controls the movement apparatus such that a pair of facing magnetic poles of the bending magnet apparatus to be excited are positioned on a beam turning trajectory along which an ion beam of the energy turn, and that controls a power supply such that the pair of magnetic poles to be excited are excited.

(C1) Hereinafter, a more preferable configuration of an accelerator in which multiple annular beam turning trajectories, which are formed by multiple magnetic poles formed in each iron core of a pair of iron cores and along which ion beams of different energies respectively turn, are densely formed in the vicinity of an inlet of a beam extraction path, will be described.

(C2) In the accelerator according to (C1), desirably, an eccentric trajectory region is formed at the periphery of an ion injection portion, and in the eccentric trajectory region, the multiple annular beam turning trajectories are formed with the respective centers eccentric with other, the annular beam turning trajectories are densely formed in the vicinity of the beam extraction path between the ion injection portion and the inlet of the beam path, and gaps between annular beam turning trajectories are wide in a direction 180° opposite to the inlet of the beam path relative to the ion injection portion.

(C3) In the accelerator according to (C2), desirably, a concentric trajectory region, in which multiple annular concentric beam turning trajectories are formed around the ion injection portion, is formed, and the eccentric trajectory region surrounds the concentric trajectory region.

Advantageous Effects of Invention

According to the present invention, it is possible to efficiently extract ion beams of different energies from an accelerator.

BRIEF DESCRIPTION OF DRAWINGS

FIG. 1 is a diagram illustrating the configuration of a particle beam irradiation system in Embodiment 1 which is a preferred embodiment of the present invention.

FIG. 2 is a perspective view of an accelerator of the particle beam irradiation system illustrated in FIG. 1.

FIG. 3 is a cross-sectional view (sectional view taken along line II-II in FIGS. 5 and 6) of the accelerator illustrated in FIG. 2.

FIG. 4 is an enlarged view illustrating the vicinity of an injection electrode of the accelerator illustrated in FIG. 2.

FIG. 5 is a sectional view taken along line V-V in FIG. 2.

FIG. 6 is a sectional view taken along line VI-VI in FIG. 2.

FIG. 7 is a side view of a massless septum illustrated in FIG. 2.

FIG. 8 is a view which is seen in a VIII-VIII direction in FIG. 7.

FIG. 9 is a block diagram illustrating a detailed configuration of a control system illustrated in FIG. 1.

FIG. 10 is a graph illustrating multiple ion beam trajectories, multiple isochronous lines, and a magnetic field distribution formed inside the accelerator illustrated in FIG. 2.

FIG. 11 is a graph illustrating a change in a gap between a magnetic pole 8E along an isochronous line $IL_1$ and a median plane illustrated in FIGS. 3 and 10.

FIG. 12 is a graph illustrating a change in a gap between the magnetic pole 8E along an isochronous line $IL_2$ and the median plane illustrated in FIGS. 3 and 10.

FIG. 13 is a graph illustrating a change in a gap between the magnetic pole 8E along an isochronous line $IL_3$ and the median plane illustrated in FIGS. 3 and 10.

FIG. 14 is a characteristic graph illustrating a relationship between the advance distance of an ion beam and magnetic field strength when the energy of the ion beam is changed.

FIG. 15 is a characteristic graph illustrating a relationship between the advance distance of an ion beam and an n value when the energy of the ion beam is changed.

FIG. 16 is a characteristic graph illustrating a change of each of a modulation wave, a double modulation wave, and a triple modulation wave versus the kinetic energy of an ion beam.

FIG. 17 is a characteristic graph illustrating a change in a betatron oscillation frequency in horizontal and vertical directions versus the kinetic energy of an ion beam.

FIG. 18 is a characteristic graph illustrating a relationship between the advance distance of an ion beam and a horizontal β function when the energy of the ion beam is changed.

FIG. 19 is a characteristic graph illustrating a relationship between the advance distance of an ion beam and a vertical β function when the energy of the ion beam is changed.

FIG. 20 is a graph illustrating the amount of ejection of an extracted ion beam versus the kinetic energy of the ion beam.

FIG. 21 is a characteristic graph illustrating a relationship between the advance distance of an ion beam and a horizontal displacement of the ion beam from a trajectory until the ion beam ejected by the massless septum reaches an extraction position.

FIG. 22 is a graph illustrating excitation of a pair of facing magnetic poles of the massless septum illustrated in FIG. 7.

FIG. 23 is a flowchart illustrating a sequence from injection of ions into the accelerator to extraction of ion beams from the accelerator in a particle beam irradiation method of the particle beam irradiation system illustrated in FIG. 1.

FIG. 24 is a graph illustrating a relationship between a position in a radial direction of a vacuum chamber and the number of ion beams (beam current).

FIG. 25 is graphs illustrating a change of each state quantity of the accelerator of the particle beam irradiation system in operation.

FIG. 26 is a flowchart illustrating a sequence of irradiating a target volume of a patient with ion beams in the particle beam irradiation method of the particle beam irradiation system illustrated in FIG. 1.

FIG. 27 is a view illustrating beam turning trajectories formed inside an accelerator of a particle beam irradiation system in Embodiment 2 which is another preferred embodiment of the present invention.

FIG. 28 is a view illustrating the configuration of a particle beam irradiation system in Embodiment 3 which is still another preferred embodiment of the present invention.

FIG. 29 is a block diagram illustrating the configuration of a particle beam irradiation system in Embodiment 4 which is still another preferred embodiment of the present invention.

FIG. 30 is a detailed cross-sectional view of an accelerator illustrated in FIG. 29.

FIG. 31 is a block diagram illustrating a detailed configuration of a control system illustrated in FIG. 29.

FIG. 32 is a flowchart illustrating a sequence of irradiating a target volume of a patient with ion beams in a particle beam irradiation method of the particle beam irradiation system illustrated in FIG. 29.

FIG. 33 is a block diagram illustrating the configuration of a particle beam irradiation system in Embodiment 5 which is still another preferred embodiment of the present invention.

FIG. 34 is a detailed cross-sectional view of an accelerator illustrated in FIG. 33.

FIG. 35 is a flowchart illustrating a sequence of irradiating a target volume of a patient with ion beams in a particle beam irradiation method of the particle beam irradiation system illustrated in FIG. 33.

FIG. 36 is a block diagram illustrating the configuration of a particle beam irradiation system in Embodiment 6 which is still another preferred embodiment of the present invention.

FIG. 37 is a detailed cross-sectional view (sectional view taken along line B-B in FIG. 38) of an accelerator illustrated in FIG. 36.

FIG. 38 is a sectional view taken along line A-A in FIG. 37.

FIG. 39 is an enlarged view illustrating the vicinity of a massless septum illustrated in FIG. 38.

FIG. 40 is a side view of a beam current measuring apparatus illustrated in FIG. 39.

FIG. 41 is a view which is seen in a D-D direction in FIG. 40.

FIG. 42 is a block diagram illustrating the configuration of a particle beam irradiation system in Embodiment 7 which is still another preferred embodiment of the present invention.

FIG. 43 is a detailed cross-sectional view of an accelerator illustrated in FIG. 42.

FIG. 44 is a cross-sectional view (sectional view taken along line G-G in FIGS. 45 and 46) illustrating the vicinity of a vacuum chamber of a particle beam irradiation system in Embodiment 8 which is still another preferred embodiment of the present invention.

FIG. 45 is a sectional view taken along line E-E in FIG. 44.

FIG. 46 is a sectional view taken along line F-F in FIG. 44.

FIG. 47 is a view illustrating another example of disposition of a massless septum.

FIG. 48 is a cross-sectional view of a particle beam irradiation system in Embodiment 9 which is still another preferred embodiment of the present invention.

DESCRIPTION OF EMBODIMENTS

Inventors have done various studies so as to realize an accelerator that is capable of continuously extracting ion beams like a cyclotron and extracting ion beams of different energies like a synchrotron.

First, the inventors have paid attention to a concept in which gaps (gaps between beam turning trajectories in a radial direction of a vacuum chamber) between beam turning trajectories of ion beams turning around inside the vacuum chamber of the cyclotron are increased. In a case where the gaps between the beam turning trajectories are increased, that is, turn separations have been increased, the diameter of the vacuum chamber is increased, and the size of the cyclotron is increased. This is contrary to a reduction in the size of the accelerator. In the cyclotron in the related art, concentric circular beam turning trajectories are formed inside the vacuum chamber, and it is not easy to ensure a turn separation at a high energy. Therefore, it is not easy to efficiently extract ion beams of different energies.

In a cyclotron, a circular vacuum chamber is used, an ion source communicates with the center of the vacuum chamber such that ions are injected to the center of the vacuum chamber. The inventors have considered a concept in which in the cyclotron, the ion source connected to the center of the vacuum chamber is moved to a beam extraction port formed in the vacuum chamber and is connected to the vacuum chamber, and ions from the ion source are not injected to the center of the vacuum chamber, but are injected to a position offset to the beam extraction port inside the vacuum chamber. As a result, gaps between beam turning trajectories formed inside the vacuum chamber are narrow between an ion injection point, to which ions are injected from the ion source, and the beam extraction port, and unlike those between the ion injection point and the beam extraction port, gaps between beam turning trajectories formed inside the vacuum chamber can be increased between the ion injection point and a direction positioned 180° opposite to the beam extraction port in the vacuum chamber.

The inventors have devised new accelerators capable of efficiently extracting ion beams of different energies by adopting the aforementioned concept regarding the formation of aforementioned beam turning trajectories.

Embodiments of the present invention, which adopt the accelerators newly devised by the inventors, will be described with reference to the accompanying drawings.

Embodiment 1

Hereinafter, a particle beam irradiation system in Embodiment 1, which is a preferred embodiment of the present invention, will be described with reference to FIGS. 1 to 8.

A particle beam irradiation system 1 in the embodiment is disposed in a building (not illustrated), and is installed on a floor of the building. The particle beam irradiation system 1 includes an ion beam generator 2; a beam transport 13; a rotating gantry 6; an irradiation apparatus 7; and a control system 65. The ion beam generator 2 includes an ion source 3, and an accelerator 4 connected to the ion source 3. The accelerator 4 in the embodiment is an energy-variable continuous wave accelerator.

The beam transport 13 includes a beam path (beam duct) 48 that reaches the irradiation apparatus 7. The beam transport 13 is configured such that multiple quadrupole magnets 46, a bending magnet 41, multiple quadrupole magnets 47, a bending magnet 42, quadrupole magnets 49 and 50, and bending magnets 43 and 44 are disposed on the beam path 48 in the listed sequence from the accelerator 4 toward the irradiation apparatus 7. A portion of the beam path 48 of the beam transport 13 is installed in the rotating gantry 6, and the bending magnet 42, the quadrupole magnets 49 and 50, and the bending magnets 43 and 44 are also installed in the rotating gantry 6. The beam path 48 is connected to a beam extraction path 20 (refer to FIG. 2) that is formed in a septum magnet 19 for extraction provided in the accelerator 4. The rotating gantry 6 is a rotating apparatus that rotates around a rotational shaft 45 so as to turn the irradiation apparatus 7 around the rotational shaft 45.

The irradiation apparatus 7 includes two scanning magnets (ion beam scanners) 51 and 52; a beam point monitor 53; and a dose monitor 54. The scanning magnets 51 and 52, the beam point monitor 53, and the dose monitor 54 are disposed along a central axis, that is, a beam axis of the irradiation apparatus 7. The scanning magnets 51 and 52, the beam point monitor 53, and the dose monitor 54 are disposed inside a casing (not illustrated) of the irradiation apparatus 7. The beam point monitor 53 and the dose monitor 54 are disposed downstream of the scanning magnets 51 and 52. The scanning magnet 51 bends ion beams in a plane perpendicular to the central axis of the irradiation apparatus 7, and scans the ion beams in a y direction. The scanning magnet 52 bends ion beams in the plane, and scans the ion beams in an x direction perpendicular to the y direction. The irradiation apparatus 7 is attached to the rotating gantry 6, and is disposed downstream of the bending magnet 44. A treatment bed 55, on which a patient 56 lies, is disposed to face the irradiation apparatus 7.

The control system 65 includes a central control apparatus 66; an accelerator and transport control apparatus 69; a scanning control apparatus 70; a rotation control apparatus 88; and a database 72. The central control apparatus 66 includes a central processing unit (CPU) 67 and a memory 68 connected to the CPU 67. The accelerator and transport control apparatus 69, the scanning control apparatus 70, the rotation control apparatus (the fourth control apparatus) 88, and the database are connected to the CPU 67. A charged particle beam irradiation system 1 includes a treatment planning system 73. The treatment planning system 73 is connected to the database 72.

Figure 9:
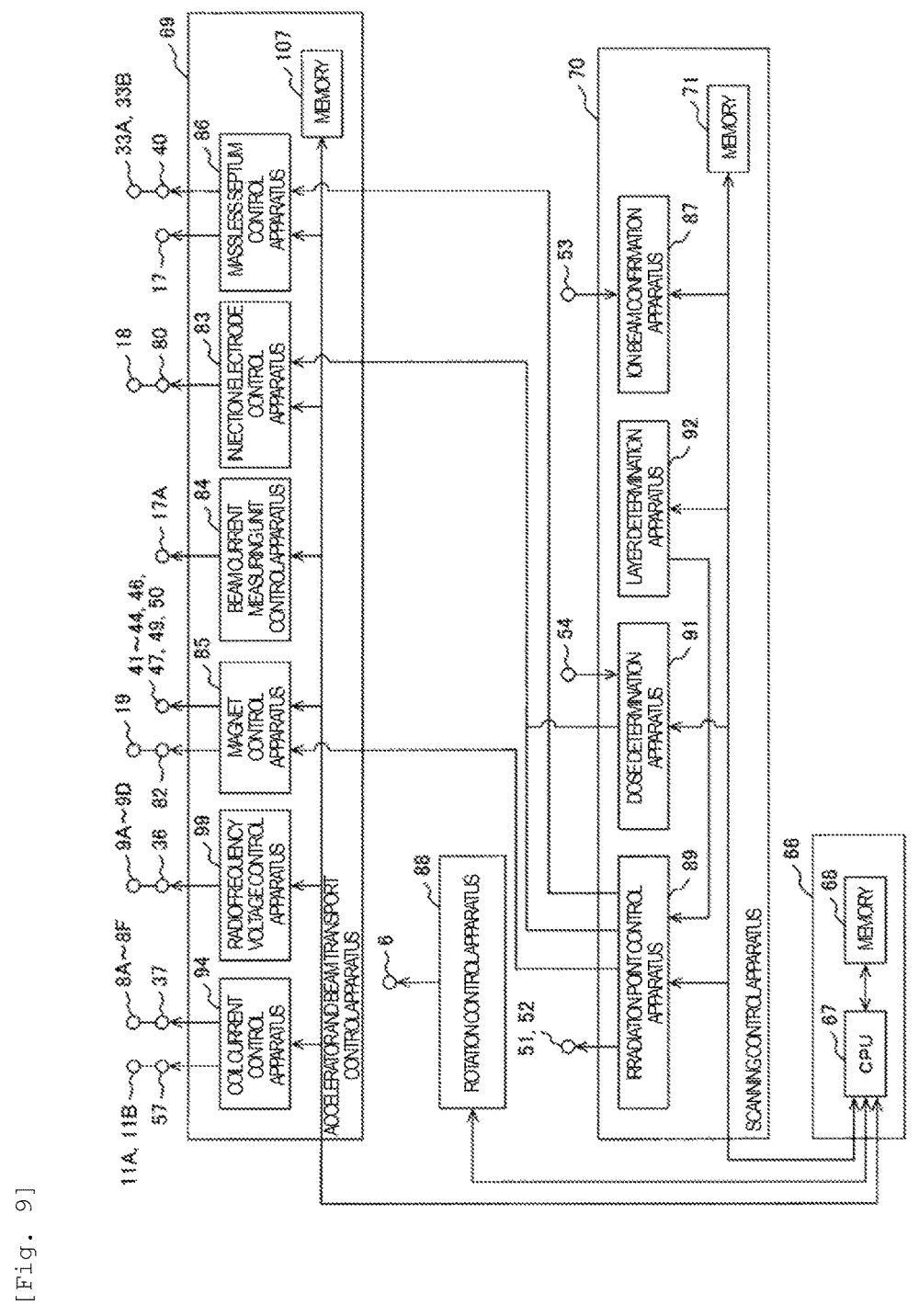

The control system 65 will be described in detail with reference to FIG. 9. The accelerator and transport control apparatus 69 includes an injection magnet control apparatus 83; a beam current measuring unit control apparatus 84; a magnet control apparatus 85; a massless septum control apparatus (a first control apparatus) 86; a coil current control apparatus (a third control apparatus) 94; a radiofrequency voltage control apparatus 99; and a memory 107. The scanning control apparatus includes an ion beam confirmation apparatus 87; an irradiation point control apparatus 89; a dose determination apparatus 91; a layer determination apparatus 92; and a memory 70. The CPU 67 is connected to the injection magnet control apparatus 83, the beam current measuring unit control apparatus 84, the magnet control apparatus 85, the massless septum control apparatus 86, the coil current control apparatus 94, the radiofrequency voltage control apparatus 99, the memory 107, the ion beam confirmation apparatus 87, the irradiation point control apparatus 89, the dose determination apparatus 91, the layer determination apparatus 92, and the memory 70. The irradiation point control apparatus 89 is connected to the injection magnet control apparatus 83, the magnet control apparatus 85, and the massless septum control apparatus 86. The dose determination apparatus 91 is connected to the injection magnet control apparatus 83. The layer determination apparatus 92 is connected to the irradiation point control apparatus 89. The memory 107 is connected to the injection magnet control apparatus 83, the beam current measuring unit control apparatus 84, the magnet control apparatus 85, the massless septum control apparatus 86. The memory 70 is connected to the irradiation point control apparatus 89, the dose determination apparatus 91, and the layer determination apparatus 92.

Hereinafter, the configuration of the accelerator 4 will be described in detail with reference to FIGS. 3, 4, 5, and 6. The accelerator 4 includes a vacuum chamber 27 including circular iron cores 14A and 14B which face each other. The iron cores 14A and 14B are joined together such that the vacuum chamber 27 is formed and an outer shell of the accelerator 4 is formed, which will be described later. The iron core 14A includes a return yoke 5A and magnetic poles 7A to 7F. The iron core 14B includes a return yoke 5B and magnetic poles 7A to 7F. A specific configuration of each of the magnetic poles 7A to 7F will be described later. The return yoke 5A includes a circular base portion 74A having a predetermined thickness, and a cylindrical portion (for example, a circular cylinder-shaped portion) 75A that extends from a surface of the base portion 74A in a direction perpendicular to the surface. The return yoke 5B includes a base portion 74B, and a cylindrical portion (for example, a circular cylinder-shaped portion) 75B that extends from a surface of the base portion 74B in a direction perpendicular to the surface (refer to FIGS. 5 and 6). The base portion 74A seals one end portion of the cylindrical portion 75A, and the return yoke 5A opens in the other end portion. The base portion 74B seals one end portion of the cylindrical portion 75B, and the return yoke 5B opens in the other end portion. Contact surfaces of the cylindrical portions 75A and 75B are sealed which are contact surfaces of the iron cores 14A and 14B of the vacuum chamber 27.

As illustrated in FIGS. 5 and 6, the vacuum chamber 27 is configured such that the iron cores 14A and 14B, specifically, the return yokes 5A and 5B are joined together in a state where open portions of the return yokes 5A and 5B are disposed to face each other, that is, the cylindrical portions 75A and 75B face each other. In the embodiment, the vacuum chamber 27 is installed on the floor of the building such that the return yoke 5B is installed at a lower position on the floor and the return yoke 5A is mounted on the return yoke 5B (refer to FIG. 6). In the embodiment, the cylindrical portions 75A and 75B respectively form side walls of the return yokes 5A and 5B, and serve a side wall of the vacuum chamber 27. An ion injection tube 3A is connected to the ion source 3 disposed outside the iron core 14A, is attached to the base portion 74A of the return yoke 5A, and passes through the base portion 74A.

A median plane 77 (refer to FIGS. 5 and 6) illustrated by the alternate long and short dash line is a plane which is formed inside the vacuum chamber 27 and at a contact position between the return yokes 5A and 5B, and a plane on which ion beams accelerate and turn inside the vacuum chamber 27. Beam turning trajectories, along which respective ion beams of different energies turn, are formed on the median plane 77, which will be described later. Since ion beams turn in a direction (direction of a central axis C of the vacuum chamber 27) perpendicular to the median plane 77 while being subjected to betatron oscillation, the ion beams turn in a beam turning region 76 (refer to FIGS. 5 and 6) having a predetermined width in the direction perpendicular to the median plane 77. The central axis C of the vacuum chamber 27 also is a central axis of the iron cores 14A and 14B.

A suction tube 26 is disposed on an extension line of a central axis of the ion injection tube 3A, passes through the base portion 74B, and is attached to the base portion 74B. A vacuum pump 25 is attached to an outer surface of the base portion 74B, and is connected to the suction tube 26. The suction tube 26 opens in the beam turning region 76.

The accelerator 4 includes the magnetic poles 7A, 7B, 7C, 7D, 7E, and 7F; radiofrequency acceleration electrodes 9A, 9B, 9C, and 9D; annular coils 11A and 11B; a massless septum 12; a beam current measuring unit 15; an injection electrode 18; and the septum magnet 19 for extraction.

The annular coil (preferably, a circular coil) 11B is disposed inside the cylindrical portion 75B of the return yoke 5B along an inner surface of the cylindrical portion 75B (refer to FIGS. 3, 5, and 6). Two lead-out wirings 22 are connected to the annular coil 11B, pass through the cylindrical portion 75B, and reach the outside of the vacuum chamber 27.

Similar to the annular coil 11B, the annular coil 11A is disposed inside the cylindrical portion 75A of the return yoke 5A along an inner surface of the cylindrical portion 75A (refer to FIGS. 5 and 6). Similar to the annular coil 11B, two lead-out wirings (not illustrated) are also connected to the annular coil 11A, and the lead-out wirings pass through the cylindrical portion 75A, and reach the outside of the vacuum chamber 27. The central axis C of the vacuum chamber 27 is a central axis of each of the annular coils 11A and 11B. The center of gravity of each of the annular coils 11A and 11B is positioned on the central axis C. The annular coils 11A and 11B are annular main coils.

The curved septum magnet 19 passes through the cylindrical portions 75A and 75B, and is attached to the cylindrical portion 75B of the return yoke 5B. One end of the septum magnet 19 is positioned inside the vacuum chamber 27, and is positioned on the inside the annular coils 11A and 11B. The septum magnet 19 forms a beam extraction path 20. The one end of the septum magnet 19, and one end, that is, an inlet of the beam extraction path 20 are positioned inside the vacuum chamber 27, and are positioned close to inner surfaces of the annular coils 11A and 11B inside the annular coils 11A and 11B. The septum magnet 19 is disposed between the annular coils 11A and 11B in the direction of the central axis C of the vacuum chamber 27.

The magnetic poles 7A, 7B, 7C, 7D, 7E, and 7F are formed in each of the iron cores 14A and 14B. Each of the magnetic poles 7A, 7B, 7C, 7D, 7E, and 7F which are formed in the iron core 14A protrudes from the base portion 74A of the return yoke 5A in an extension direction of the cylindrical portion 75A. Each of the magnetic poles 7A, 7B, 7C, 7D, 7E, and 7F which are formed in the iron core 14B protrudes from the base portion 74B of the return yoke 5B in an extension direction of the cylindrical portion 75B (refer to FIG. 6). The radiofrequency acceleration electrodes 9A, 9B, 9C, and 9D are respectively attached to the cylindrical portions 75A and 75B of the return yokes 5A and 5B via waveguide tubes 10A to 10D. Each of the magnetic poles 7A, 7B, 7C, 7D, 7E, and 7F and the radiofrequency acceleration electrodes 9A, 9B, 9C, and 9D, which are provided in the return yoke 5B, is disposed inside the annular coil 11B (refer to FIG. 3). Similar to the magnetic poles and the radiofrequency acceleration electrodes which are provided in the return yoke 5B, each of the magnetic poles 7A, 7B, 7C, 7D, 7E, and 7F and the radiofrequency acceleration electrodes 9A, 9B, 9C, and 9D, which are provided in the return yoke 5A, is also disposed inside the annular coil 11A.

Disposition of each of the magnetic poles 7A, 7B, 7C, 7D, 7E, and 7F and the radiofrequency acceleration electrodes 9A, 9B, 9C, and 9D, which are provided in the return yoke 5B, will be described in detail with reference to FIG. 3. The magnetic poles 7A, 7B, 7C, 7D, 7E, and 7F of the return yoke 5A are respectively symmetrical in shape and disposition with the magnetic poles 7A, 7B, 7C, 7D, 7E, and 7F of the return yoke 5B relative to the median plane 77. The radiofrequency acceleration electrodes 9A, 9B, 9C, and 9D of the return yoke 5A are respectively symmetrical in shape and disposition with the radiofrequency acceleration electrodes 9A, 9B, 9C, and 9D of the return yoke 5B relative to the median plane 77. For this reason, description of each of the magnetic poles and the radiofrequency acceleration electrodes of the return yoke 5A will be omitted.

The magnetic poles 7A, 7B, 7C, 7D, 7E, and 7F, which are formed on the base portion 74B of the return yoke 5B, are protrusions which protrude from the base portion 74B (refer to FIG. 6).

In the return yoke 5B, the magnetic poles 7A, 7B, 7C, 7D, 7E, and 7F and recesses 29A to 29F are alternately disposed in a circumferential direction of the return yoke 5B. That is, the recess 29A (a first recess) is formed between the magnetic poles 7A and 7B, the recess 29B is formed between the magnetic poles 7B and 7D, and the recess 29F is formed between the magnetic poles 7A and 7C (refer to FIGS. 3, 4, and 6). In the return yoke 5B, the recess 29C is formed between the magnetic poles 7D and 7F, the recess 29D (a second recess) is formed between the magnetic poles 7F and 7E, and the recess 29E is formed between the magnetic poles 7E and 7C (refer to FIGS. 3, 4, and 5). In the return yoke 5B, a recess 29G is formed between the magnetic poles 7A, 7B, 7C, 7D, 7E, and 7F and the cylindrical portion 75B, and the annular coil 11B is disposed in side of the recess 29G (refer to FIGS. 3 and 6).

A tip end portion of the ion injection tube 3A is surrounded by tip ends of the magnetic poles 7A, 7B, 7C, 7D, 7E, and 7F formed on the base portion 74A of the return yoke 5A. The injection electrode 18 is attached to a tip end of the ion injection tube 3A, crosses the median plane 77, and is disposed in the beam turning region 76. The tip end of the ion injection tube 3A communicates with the beam turning region 76. An ion inlet port, which is an ion injection port formed at the tip end of the ion injection tube 3A, and the injection electrode 18 are disposed on an alternate long and short dash line X that connects the central axis C of the annular coils 11A and 11B to the inlet of the beam extraction path 20. The ion inlet port and the injection electrode 18 are disposed offset toward the inlet of the beam extraction path 20 from the central axis C of the annular coils 11A and 11B. That is, the ion inlet port and the injection electrode 18 are disposed at a different position from that of the central axis C, and are disposed at a different position from that of the center of gravity of the annular coils 11A and 11B. The ion inlet port and the injection electrode 18 are disposed at a different position from that of the central axis C of the iron cores 14A and 14B. The ion inlet port is an ion injection port through which ions are injected to the beam turning region 76. An ion injection portion 109 (refer to FIG. 10) receives ions from the ion inlet port. The ion injection portion 109 is a region that is formed inside an innermost beam turning trajectory, and specifically is formed at the periphery of the injection electrode 18 in the beam turning region 76.

The recess 29D (the second recess) which is positioned between the injection electrode 18 and the inlet of the beam extraction path 20, and the recess 29A (the first recess), which is positioned 180° opposite to the inlet of the beam extraction path 20 relative to the injection electrode 18, are disposed straight along the alternate long and short dash line X.

In the accelerator of the embodiment, multiple protrusions (magnetic poles) are formed in the facing iron cores so as to obtain strong convergence by intensifying and weakening a magnetic field along beam turning trajectories. Hereinafter, in the accelerator of the embodiment in which an ion injection point is provided at a position that is on a trajectory plane and is different from that of the center of the circular iron core, the shapes of the protrusions (magnetic poles) required to obtain a magnetic field distribution for forming eccentric beam turning trajectories will be described. The shapes of the iron cores and the recesses (magnetic poles) suitable for forming eccentric beam turning trajectories differ depending on masses or charges of accelerated ion particles, and are not limited to the shapes illustrated in the drawings. The shapes of the magnetic poles illustrated in the drawings and the following description are an example in which protons are used in the present invention. The center of the iron cores are positioned on the central axis of the iron cores.

The magnetic poles 7A, 7B, 7C, 7D, 7E, and 7F, which are formed on the base portion 74A of the return yoke 5B, are radially disposed around the ion injection port, that is, the position of the injection electrode 18, in a horizontal direction (direction perpendicular to the central axis C). The width of each of the magnetic poles in the circumferential direction of the annular coil 11B is decreased toward the injection electrode 18. A tip end of each of the magnetic poles is sharp, and each sharp tip end faces the injection electrode 18. The width of each of the magnetic poles 7A, 7B, 7C, 7D, 7E, and 7F in the circumferential direction of the annular coil 11B is increased to the maximum value in a portion of each magnetic pole which faces the annular coil 11B.

The magnetic pole 7A is bent at bent points 24A and 24B which are formed on two facing side surfaces of the magnetic pole 7A. The magnetic pole 7B is bent at bent points 24C and 24D which are formed on two facing side surfaces of the magnetic pole 7B. The magnetic pole 7C is bent at bent points 24E and 24F which are formed on two facing side surfaces of the magnetic pole 7C (refer to FIG. 4). The magnetic pole 7D is bent at bent points 24G and 24H which are formed on two facing side surfaces of the magnetic pole 7D. The magnetic pole 7E is bent at bent points 24I and 24J which are formed on two facing side surfaces of the magnetic pole 7E. The magnetic pole 7F is bent at bent points 24K and 24L which are formed on two facing side surfaces of the magnetic pole 7F (refer to FIG. 4).

A portion of each of the magnetic poles 7A, 7B, 7C, 7D, 7E, and 7F between the bent points and an end surface thereof facing the annular coil 11B is bent toward the recess 29A. That is, the portion of each of the magnetic poles 7A, 7C, and 7E between the bent points and the end surface thereof facing the annular coil 11B is bent toward the recess 29A in a turning direction of ion beams. The portion of each of the magnetic poles 7B, 7D, and 7F between the bent points and the end surface thereof facing the annular coil 11B is bent toward the recess 29A in a direction opposite to the turning direction of ion beams. The absolute value of the bending angle of a bending portion of the magnetic pole 7A is the same as that of the bending angle of a bending portion of the magnetic pole 7B. The absolute value of the bending angle of a bending portion of the magnetic pole 7C is the same as that of the bending angle of a bending portion of the magnetic pole 7D. The absolute value of the bending angle of a bending portion of the magnetic pole 7E is the same as that of the bending angle of a bending portion of the magnetic pole 7F. The absolute values of the bending angles of the magnetic poles 7A, 7C, and 7E are increased in the listed sequence. The absolute values of the bending angles of the magnetic poles 7E and 7F are the maximum values.

A portion of the magnetic pole 7A between the bent points 24A and 24B and the tip end thereof, a portion of the magnetic pole 7B between the bent points 24C and 24D and the tip end thereof, a portion of the magnetic pole 7C between the bent points 24E and 24F and the tip end thereof, a portion of the magnetic pole 7D between the bent points 24G and 24H and the tip end thereof, a portion of the magnetic pole 7E between the bent points 24I and 24J and the tip end thereof, and a portion of the magnetic pole 7F between the bent points 24K and 24L and the tip end thereof are disposed around the injection electrode 18 at every 60° in the horizontal direction.

In the embodiment, concentric trajectory region is formed around the injection electrode 18 (the ion inlet port of the ion injection tube 3A), and eccentric trajectory region is formed to surround the concentric trajectory region. The concentric trajectory region is formed as a predetermined region inside the bending portions of the magnetic poles 7A to 7F. As a result, the shape of each magnetic pole formed inside the bent points is similar to that of a radial sector type AVF cyclotron having six sectors. In the concentric trajectory region, the respective centers of the annular beam turning trajectories, which are formed in the concentric trajectory region and along which ion beams of different energies turn, are the same. That is, the magnet poles are formed such that a magnetic field can be intensified and weakened, that is, convergence and dispersion of beams can be obtained at a predetermined periodic timing of a beam turning trajectory or at a predetermined turning angle at which a magnetic pole is radially installed relative to the center of a beam turning trajectory.

Relative to the alternating long and short dash line X, the magnetic poles 7A and 7B are symmetrical in shape with each other, the magnetic poles 7C and 7D are symmetrical in shape with each other, the magnetic poles 7E and 7F are symmetrical in shape with each other, the recesses 29F and 29B are symmetrical in shape with each other, and the recesses 29E and 29C are symmetrical in shape with each other. Among six magnetic poles (protrusions) 7A to 7F formed in each of the iron cores 14A and 14B, the magnetic poles 7A, 7C, and 7E are installed to be respectively reflection-symmetrical to the magnetic poles 7B, 7D, and 7F relative to a straight line that connects the central axis C of the annular coils to the inlet of the beam extraction path 20. At the same time, in the embodiment, the magnets are installed such that all of the magnets are not rotationally symmetrical in shape with each other relative to the center of the circular iron cores, the center of gravity of the annular coils, the ion injection point. The reason for this is that even if the center of a beam turning trajectory is gradually displaced for each energy, a magnetic field can be intensified and weakened, that is, convergence and dispersion of beams can be obtained at a predetermined periodic timing of each beam turning trajectory, or as a result, at substantially the same turning angle relative to the center of each beam turning trajectory. For this reason, the magnets are reflection-symmetrical in shape with each other relative to a direction in which the centers of the beam turning trajectories are shifted, and the magnets are installed in such a way as to be diagonally inclined toward a direction opposite to the direction in which the centers are shifted. That is, the magnets are shaped such that that the magnets are not rotationally symmetrical in shape with each other. In such shapes of the magnets, the center of gravity of all of the six magnetic poles is displaced from the center of the iron cores toward the direction opposite to the direction in which the centers of the beam turning trajectories are shifted. Therefore, the center of the iron cores and the center of gravity of all of the six magnetic poles are positioned at different coordinates on a horizontal plane. A relationship between the shapes of the magnets and the beam turning trajectories will be described in detail later with reference to FIG. 10.

A trim coil 8A is installed on the magnetic pole 7A, and lead-out wirings 21A and 21B are respectively connected to both ends of the trim coil 8A. A trim coil 8B is installed on the magnetic pole 7B, and lead-out wirings 21C and 21D are respectively connected to both ends of the trim coil 8B. A trim coil 8C is installed on the magnetic pole 7C, and lead-out wirings 21E and 21F are respectively connected to both ends of the trim coil 8C. A trim coil 8D is installed on the magnetic pole 7D, and lead-out wirings 21G and 21H are respectively connected to both ends of the trim coil 8D. A trim coil 8E is installed on the magnetic pole 7E, and lead-out wirings 21I and 21J are respectively connected to both ends of the trim coil 8E. A trim coil 8F is installed on the magnetic pole 7F, and lead-out wirings 21L and 21K are respectively connected to both ends of the trim coil 8F. Each of the lead-out wirings 21A to 21K passes through a gap between the annular coils 11A and 11B, passes through the cylindrical portion 75B, and is extracted to the outside of the vacuum chamber 27.

The trim coils 8A to 8F are respectively installed on the magnetic poles 7A to 7F so as to generate an isochronous magnetic field which is desired to be generated in the median plane 77, and thus, a gap between windings of each of the installed trim coils is not constant. In each of the magnetic poles 7A to 7F, the gap between windings of each of the installed trim coils is decreased to the extent that the trim coil is closer to the inner surface of each of the annular coils than the injection electrode 18. The gap between windings of each of the trim coils installed on the magnetic poles 7A, 7C, and 7E is decreased in the listed sequence. The gap between windings of each of the trim coils installed on the magnetic poles 7B, 7D, and 7F is decreased in the listed sequence. Since beam turning trajectories 78 of a wide range of energies are densely formed in a range which is narrow in a radial direction of the annual coils, and in the vicinity of the inlet of the beam extraction path 20, in each of the magnetic poles 7E and 7F adjacent to the inlet of the beam extraction path 20, the gap between windings of the installed trim coil is decreased on an outer circumferential portion of each of the magnetic poles 7E and 7F so as to cope with a required steep magnetic field radial gradient and required high energy beam turning trajectories.

The disposition of the radiofrequency acceleration electrodes 9A, 9B, 9C, and 9D in the return yoke 5B will be described with reference to FIGS. 3 and 6.

The radiofrequency acceleration electrode 9A is disposed inside the recess 29F between the magnetic poles 7A and 7C, and is connected to the waveguide tube 10A. The radiofrequency acceleration electrode 9A inside the recess 29F is disposed between the bent points 24B and 24E and the annular coil 11B. The radiofrequency acceleration electrode 9B is disposed inside the recess 29B between the magnetic poles 7B and 7D, and is connected to the waveguide tube 10B. The radiofrequency acceleration electrode 9B inside the recess 29B is disposed between the bent points 24D and 24G and the annular coil 11B. Ion inlet port-side end surfaces of the radiofrequency acceleration electrodes 9A and 9B may be respectively positioned at a midpoint between the bent points of the radiofrequency acceleration electrode 9A and the ion inlet port and at a midpoint between the bent points of the radiofrequency acceleration electrode 9B and the ion inlet port. The waveguide tubes 10A and 10B pass through the gap between the annular coils 11A and 11B, pass through the cylindrical portion 75B, and are extracted to the outside of the vacuum chamber 27. The width of each of the radiofrequency acceleration electrodes 9A and 9B in the circumferential direction of the annular coil 11B is increased from the injection electrode 18 toward the annular coil 11B.

The radiofrequency acceleration electrode 9C is disposed inside the recess 29E between the magnetic poles 7C and 7E, and is connected to the waveguide tube 10C. The radiofrequency acceleration electrode 9C is bent at bent points 24M and 24N (refer to FIG. 4) which are formed on two side surfaces thereof. A portion of the radiofrequency acceleration electrode 9C between the bent points 24M and 24N and an end surface thereof facing the annular coil 11B is bent toward the recess 29A (the first recess) in the turning direction of ion beams. The width of the radiofrequency acceleration electrode 9C in the circumferential direction of the annular coil 11B is decreased from the bending positions of the bent points 24M and 24N toward a tip end thereof, and is increased from the bent points toward the end surface facing the annular coil 11B. The radiofrequency acceleration electrode 9D is disposed inside the recess 29C between the magnetic poles 7D and 7F, and is connected to the waveguide tube 10D. The radiofrequency acceleration electrode 9D is bent at bent points 24O and 24P (refer to FIG. 4) which are formed on two side surfaces thereof. A portion of the radiofrequency acceleration electrode 9D between the bent points 24O and 24P and an end surface thereof facing the annular coil 11B is bent toward the recess 29A (the first recess) in the direction opposite to the turning direction of ion beams. The width of the radiofrequency acceleration electrode 9D in the circumferential direction of the annular coil 11B is decreased from the bending positions of the bent points 24O and 24P toward a tip end thereof, and is increased from the bent points toward the end surface facing the annular coil 11B. The waveguide tubes 10C and 10D pass through the gap between the annular coils 11A and 11B, pass through the cylindrical portion 75B, and are extracted to the outside of the vacuum chamber 27. The tip ends of the radiofrequency acceleration electrodes 9C and 9D are positioned close to the injection electrode 18, and are connected to each other in an ion injection region in which the injection electrode 18 is installed. The injection electrode faces a connection portion between the radiofrequency acceleration electrodes 9C and 9D, and is disposed in the beam turning region 76 while being positioned away from the connection portion.

The recess 29A, the injection electrode 18, the recess 29D are disposed along the alternate long and short dash line X passing through the central axis C of the vacuum chamber 27.

As illustrated in FIG. 6, each of the magnetic poles 7A to 7F, which are formed on the base portion 74A of the return yoke 5A, are a protrusion that protrudes from the cylindrical portion 75A. Similar to the return yoke 5B, also in the return yoke 5A, a recess 29G is formed between the magnetic poles 7A, 7B, 7C, 7D, 7E, and 7F and the cylindrical portion 75A, and the annular coil 11A is disposed inside the recess 29G (refer to FIG. 6).

In a state where the return yokes 5A and 5B are disposed to face each other, and are joined together, the magnetic poles 7A face each other, the magnetic poles 7B face each other, the magnetic poles 7C face each other, the magnetic poles 7D face each other, the magnetic poles 7E face each other, and the magnetic poles 7F face each other. In a state where the return yokes 5A and 5B are joined together in such a manner, the recesses 29A face each other, the recesses 29B face each other, the recesses 29C face each other, the recesses 29D face each other, the recesses 29E face each other, and the recesses 29F face each other.

Relative to the median plane 77, the magnetic poles 7A are symmetrical in shape with each other, the magnetic poles 7B are symmetrical in shape with each other, the magnetic poles 7C are symmetrical in shape with each other, the magnetic poles 7D are symmetrical in shape with each other, the magnetic poles 7E are symmetrical in shape with each other, and the magnetic poles 7F are symmetrical in shape with each other, all of which are formed in the return yokes 5A and 5B. Relative to the median plane 77, the recesses 29A are symmetrical in shape with each other, the recesses 29B are symmetrical in shape with each other, the recesses 29C are symmetrical in shape with each other, the recesses 29D are symmetrical in shape with each other, the recesses 29E are symmetrical in shape with each other, and the recesses 29F are symmetrical in shape with each other, all of which are formed in the return yokes 5A and 5B.

As illustrated in FIG. 5, at the position of the ion injection tube 3A, a bottom surface 95 of the recess 29A formed in the return yoke 5A approaches closest to a bottom surface 95 of the recess 29A formed in the return yoke 5B. In the vacuum chamber 27, the bottom surfaces 95 are surfaces which are inclined in a direction that is 180° opposite to the inlet of the beam extraction path 20 relative to the injection electrode 18, specifically, are inclined toward the massless septum 12 disposed inside the recess 29A. A width between the bottom surfaces 95 in a direction of the central axis C is gradually increased from the ion injection tube 3A toward the massless septum 12. As for the magnitude of the width formed between the bottom surfaces 95, the width between the bottom surface 95 of the recess 29A formed in the return yoke 5A and the bottom surface 95 of the recess 29A formed in the return yoke 5B becomes the maximum value at a position at which the massless septum 12 is disposed.

As illustrated in FIG. 5, at the position of the ion injection tube 3A, the bottom surface 95 of the recess 29D formed in the return yoke 5A approaches closest to the bottom surface 95 of the recess 29D formed in the return yoke 5B. In the vacuum chamber 27, the bottom surfaces 95 are surfaces which are inclined from the position of the ion injection tube 3A toward the septum magnet 19. A width between the bottom surfaces 95 in the direction of the central axis C is gradually increased from the ion injection tube 3A toward the septum magnet 19. A width between a portion (on which the annular coil 11A is disposed) of the bottom surface 95 of the recess 29D formed in the return yoke 5A and a portion (on which the annular coil 11A is disposed) of the bottom surface 95 of the recess 29D formed in the return yoke 5B is the same as that between a portion (on which the massless septum 12 is disposed) of the bottom surface 95 of the recess 29A formed in the return yoke 5A and a portion (on which the massless septum 12 is disposed) of the bottom surface 95 of the recess 29A formed in the return yoke 5B.

The magnetic poles 7A, 7B, 7C, 7D, 7E, and 7F, the base portion 74A, and the cylindrical portion 75A are integrally formed into the iron core 14A. The magnetic poles 7A, 7B, 7C, 7D, 7E, and 7F, the base portion 74B, and the cylindrical portion 75B are integrally formed into the iron core 14B.

As illustrated in FIG. 6, a gap 28A is formed between the magnetic pole 7A of the return yoke 5A and the facing magnetic pole 7A of the return yoke 5B, a gap 28B is formed between the magnetic poles 7B which face each other in an axial direction of the vacuum chamber 27, a gap 28C is formed between the magnetic pole 7C of the return yoke 5A and the facing magnetic pole 7C of the return yoke 5B, and a gap 28D is formed between the magnetic pole 7D of the return yoke 5A and the facing magnetic pole 7D of the return yoke 5B. In addition, gaps are respectively formed between the magnetic pole 7E of the return yoke 5A and the facing magnetic pole 7E of the return yoke 5B and between the magnetic pole 7F of the return yoke 5A and the facing magnetic pole 7F of the return yoke 5B, which is not illustrated. A gap is also formed between the radiofrequency acceleration electrode 9A of the return yoke 5A and the facing radiofrequency acceleration electrode 9A of the return yoke 5B. A gap is also formed between the radiofrequency acceleration electrode 9B of the return yoke 5A and the facing radiofrequency acceleration electrode 9B of the return yoke 5B. Similarly, a gap is also formed between the radiofrequency acceleration electrode 9C of the return yoke 5A and the facing radiofrequency acceleration electrode 9C of the return yoke 5B, and a gap is also formed between the radiofrequency acceleration electrode 9D of the return yoke 5A and the facing radiofrequency acceleration electrode 9D of the return yoke 5B, which is not illustrated.

All of the gaps formed between the magnetic poles and the gaps formed between the radiofrequency acceleration electrodes contain the median plane 77, and form the beam turning region 76 in which ion beams turn in the horizontal direction.

The massless septum 12 is disposed inside the recesses 29A formed in the return yokes 5A and 5B (refer to FIG. 5), and is positioned between the magnetic poles 7A and 7B. The massless septum 12 will be described in detail with reference to FIGS. 7 and 8. Each of the massless septum 12 and an energy absorber 62 (to be described later) is a beam separation apparatus that deviates an ion beam from a beam turning trajectory along which the ion beam turns.

The massless septum 12 includes an iron core member 30 and coils 33A and 33B. The iron core member 30 includes iron core portions 31A and 31B made of steel and a connection portion 31C made of steel. The flat plate-like iron core portion 31A and the flat plate-like iron core portion 31B are disposed while being parallel to and facing each other. One end portion of the iron core portion 31A is connected to one end portion of the iron core portion 31B via the connection portion 31C. Multiple (for example, 28) magnetic poles 32A which are protrusions are formed on a surface of the iron core portion 31A which faces the iron core portion 31B. The magnetic poles 32A are disposed in a row in a longitudinal direction of the iron core portion 31A, with a predetermined gap therebetween. The coil 33A is separately wrapped around each of the magnetic poles 32A. Multiple (for example, 28) magnetic poles 32B which are protrusions are formed on a surface of the iron core portion 31B which faces the iron core portion 31A. The magnetic poles 32B are disposed in a row in a longitudinal direction of the iron core portion 31B, with a predetermined gap therebetween. The coil 33B is separately wrapped around each of the magnetic poles 32B.

Wirings 23A are respectively connected to both ends of each of the coils 33A. As illustrated in FIG. 8, multiple wirings 23A are bundled, one bundle of the wirings 23A is attached to one side surface of the iron core portion 31A, and the other bundle of the wirings 23A is attached to the other side surface of the iron core portion 31A. Wirings 23B are respectively connected to both ends of each of the coils 33B. As illustrated in FIG. 8, multiple wirings 23B are bundled, one bundle of the wirings 23B is attached to one side surface of the iron core portion 31B, and the other bundle of the wirings 23B is attached to the other side surface of the iron core portion 31B.

The multiple magnetic poles 32A which are formed in the iron core portion 31A, and the multiple magnetic poles 32B, which are formed in the iron core portion 31B, are disposed such that each one of the magnetic poles 32A faces each one of the magnetic poles 32B. A beam passage 35 is formed between the magnetic poles 32A and the magnetic poles 32B, and is a gap through which turning ion beams pass. The beam passage 35 contains a portion of the median plane 77.

One end portion of a bar-shaped operation member 16 is attached to the connection portion 31C in which a through hole 31D of the massless septum 12 is formed. The operation member 16 is a support member for the massless septum 12, and is connected to a piston of a movement apparatus 17 including the piston and a cylinder (refer to FIG. 3). A position detector 38 is attached to the movement apparatus 17, and detects the position of the massless septum 12 inside the vacuum chamber 27 (refer to FIG. 1). The operation member 16 is disposed between the annular coils 11A and 11B, and is slidably attached to the cylindrical portion 75B in a state where the operation member 16 has passed through the cylindrical portion 75B of the return yoke 5B. The movement apparatus 17 may be a motor. In a case where a motor is used as the movement apparatus 17, an encoder is used as the position detector 38, and is connected to a rotational shaft of the motor.

The massless septum 12 is a bending magnet apparatus that bends ion beams at different positions in the radial direction of the annular coils disposed inside the return yokes.

A beam current measuring apparatus 98 includes a beam current measuring unit 15; a movement apparatus 17A; and a position detector 39. The beam current measuring unit 15 is disposed at the position of the recess 29A on the median plane 77 inside the vacuum chamber 27, and on the alternate long and short dash line X which passes through the central axis C of the vacuum chamber 27 and the injection electrode 18 (refer to FIG. 3). A bar-shaped operation member 16A connected to the beam current measuring unit 15 passes through the vacuum chamber 27, and extends to the outside of the vacuum chamber 27. The operation member 16A is a support member for the beam current measuring unit 15. On the outside of the vacuum chamber 27, the operation member 16A is connected to a piston of the movement apparatus 17A including the piston and a cylinder. The operation member 16A is disposed between the annular coils 11A and 11B, and is slidably attached to the cylindrical portion 75B in a state where the operation member 16A has passed through the cylindrical portion 75B of the return yoke 5B. A position detector 39 is attached to the movement apparatus 17A, and detects the position of the beam current measuring unit 15 inside the vacuum chamber 27 (refer to FIG. 1). The movement apparatus 17A may be a motor. In a case where a motor is used as the movement apparatus 17A, an encoder is used as the position detector 39, and is connected to a rotational shaft of the motor.

The operation member 16A is inserted into the beam passage formed between the multiple magnetic poles 32A and the multiple magnetic poles 32B of the massless septum 12 through the through hole 31D that is formed in the connection portion 31C (refer to FIG. 5). For this reason, when the operation member 16A is moved in a radial direction of the vacuum chamber 27 along the alternate long and short dash line X, the beam current measuring unit 15 is moved on the median plane 77 inside the beam passage 35. Since gaps between the beam turning trajectories 78 are wide at the position of the recess 29A on the alternate long and short dash line X along end surfaces of the magnetic poles 32A of the massless septum 12, it is possible to easily measure a beam current of each of the beam turning trajectories 78 by moving the beam current measuring unit 15 on the alternate long and short dash line X in the radial direction of the annular coils and performing measurement.

A radiofrequency power supply 36 is connected to the waveguide tube 10D that is connected to the radiofrequency acceleration electrode 9D (refer to FIG. 1). The waveguide tubes 10A, 10B, and 10C, which are respectively connected to the other radiofrequency acceleration electrodes 9A, 9B, and 9C, are respectively connected to radiofrequency power supplies 36 which are respectively provided for the radiofrequency acceleration electrodes, which is not illustrated. A power supply 37 is connected to the lead-out wirings 21C and 21D which are respectively connected to both the ends of the trim coil 8B provided on the magnetic pole 7B (refer to FIG. 1). The lead-out wirings, which are respectively connected to both the ends of the trim coil 8A and 8C to 8F provided on the other magnetic poles 7A and 7C to 7F, are respectively connected to power supplies 37 which are respectively provided for the magnetic poles, which are not illustrated. The radiofrequency power supplies and the magnetic poles are present inside the return yoke 5B. In the return yoke 5A, the radiofrequency acceleration electrodes 9A, 9B, 9C, and 9D are respectively connected to separate radiofrequency power supplies 36, and the magnetic poles 7A, 7B, 7C, 7D, 7E, and 7F are respectively connected to separate power supplies 37. The injection power supply 18 is connected to a power supply 82 via a wiring 81 (refer to FIG. 1).

A power supply 57 is connected to the two lead-out wirings 22 which are connected to the annular coil 11B provided in the return yoke 5B (refer to FIG. 1). The power supply 57 is connected to the two lead-out wirings 22 which are connected to the annular coil 11A provided in the return yoke 5A. One power supply 40 is connected to the wirings 23A and the wirings 23B which are respectively connected to the coils 33A and the coils 33B which are respectively wrapped around the magnetic poles 32A and the magnetic poles 32B of the massless septum 12 (refer to FIG. 1).

An excitation current is supplied from the power supply 57 to the annular coils 11A and 11B via the respective lead-out wirings 22. The iron cores 14A and 14B are magnetized due to action of the excitation current. An excitation current is supplied from the power supplies 37 to the respective trim coils 8A to 8F, which are provided on the magnetic poles 7A to 7F, via the lead-out wiring 21A, the lead-out wiring 21C, the lead-out wiring 21E, the lead-out wiring 21G, the lead-out wiring 21G, the lead-out wiring 21I, the lead-out wiring 21K. As a result, the magnetic poles 7A to 7F are excited. The ion source is started. A radiofrequency voltage is applied to the radiofrequency acceleration electrodes 9A to 9D from the respective radiofrequency power supplies 36 via the respective waveguide tubes 10A to 10D. A voltage is applied to the injection electrode 18 from the power supply 82.

Due to magnetization of the iron cores 14A and 14B, a magnetic circuit is formed by a closed loop from each of the magnetic poles 7A to 7F formed in the return yoke 5B, each of the magnetic poles 7A to 7F formed in the return yoke 5A, the base portion 74A of the return yoke 5A, the cylindrical portion 75A of the return yoke 5A, the cylindrical portion 75B of the return yoke 5B, the base portion 74B of the return yoke 5B, and each of the magnetic poles 7A to 7F formed in the return yoke 5B. At this time, magnetic lines of force are generated from the bottom surfaces 95 of the recesses 29A to 29F of the return yoke 5B toward the facing bottom surfaces 95 of the recesses 29A to 29F of the return yoke 5A. Magnetic lines of force generated between facing bottom surfaces 95 are less than magnetic lines of force generated between facing magnetic poles. A magnetic field formed between facing magnetic poles (protrusions) is higher than a magnetic field formed between facing recesses.

As a result, a magnetic field distribution illustrated in FIG. 10 is formed on the median plane 77 inside the vacuum chamber 27. This magnetic field distribution represents the distribution of isochronous magnetic fields. An isochronous magnetic field represents a magnetic field in which, even if the radius of a beam turning trajectory, along which an ion beam turn, is increased due to an increase in the energy of the accelerated ion beam, the length of time required for one turn of the ion beam is not changed. The isochronous magnetic fields are formed by the magnetic poles 7A to 7F. In FIG. 10, "high" represents a high magnetic field strength region, and "low" represents a low magnetic field strength region. High magnetic field strength regions and low magnetic field strength regions are alternately formed at the periphery of the ion inlet port, that is, the injection electrode 18. For example, in a high magnetic field strength region, the highest magnetic field strength is 2.2 T, and in a low magnetic field strength region, the lowest magnetic field strength is 0.84 T. In the embodiment, there are six high magnetic field strength regions and six low magnetic field strength regions. When FIGS. 3 and 10 overlap each other such that the positions of the injection electrodes 18 coincide with each other and the positions of the septum magnets (in FIG. 10 a point (concentration point) at which beam turning trajectories 78 are offset toward the septum magnet 19, and the multiple beam turning trajectories 78 are concentrated) coincide with each other, the six high magnetic field strength regions respectively overlap the magnetic poles 7A to 7F illustrated in FIG. 3. That is, the magnetic poles are respectively disposed in the high magnetic field strength regions. The six low magnetic field strength regions respectively overlap the recesses 29A to 29F illustrated in FIG. 3. That is, the recesses are respectively disposed in the low magnetic field strength regions.

Ions (for example, protons ($H^+$)) released from the ion source 3A are injected into the beam turning region 76 via the ion injection tube 3A, and an advance direction of the ions is bent toward the horizontal direction in the beam turning region 76 due to action of the injection electrode 18 to which a voltage is applied. The injected protons are accelerated by the radiofrequency acceleration electrodes 9A to 9D in a state where the magnetic poles 7A to 7F and the annular coils 11A and 11B are excited. The protons are accelerated in the vicinity of the injection electrode 18 by the radiofrequency acceleration electrodes 9C and 9D, and are accelerated in the vicinity of the annular coils 11A and 11B by the radiofrequency acceleration electrodes 9A to 9D. The accelerated protons form a proton ion beam (hereinafter, simply referred to as an ion beam), and the proton ion beam turns on the median plane 77 along beam turning trajectories formed at the periphery of the injection electrode 18. Specifically, since the ion beam is subjected to betatron oscillation in the direction perpendicular to the median plane 77, the ion beam turns in the beam turning region 76 having a predetermined width with the median plane 77 as a center in the direction perpendicular thereto.

FIG. 10 illustrates the beam turning trajectories 78 and magnetic field strength distributions on the median plane 77 inside the annular coil 11B, and illustrates multiple isochronous lines 79. An isochronous line represents a line that connects together the positions of turning ions (for example, protons) which are present at the same time. Each of the isochronous lines 79 illustrated by the dotted lines in FIG. 10 extends radially from the injection electrode 18, and is bent in the middle of the line (at the position of a beam turning trajectory of an ion beam of 35 MeV). Side surfaces of the magnetic poles 7A to 7F provided on each of the return yokes 5A and 5B respectively coincide with the corresponding isochronous lines 79 illustrated in FIG. 10.

As illustrated in FIG. 10, in the accelerator 4, multiple beam turning trajectories 78 are formed in the beam turning region 76. In FIG. 10, in an ion beam energy range of 250 MeV or less, the beam turning trajectory 78 is illustrated for every 0.25 MeV of energy in an energy region having an energy of 0.5 MeV or less, for every 0.5 MeV of energy in an energy region having an energy range exceeding 0.5 MeV and less than or equal to 1 MeV, for every 1 MeV of energy in an energy region having an energy range exceeding 1 MeV and less than or equal to 10 MeV or less, for every 5 MeV of energy in an energy region having an energy range exceeding 10 MeV and less than or equal to 50 MeV, for every 10 MeV of energy in an energy region having an energy range exceeding 50 MeV and less than or equal to 100 MeV, for every 20 MeV of energy in an energy region having an energy range exceeding 100 MeV and less than or equal to 220 MeV, and for every 15 MeV of energy in an energy region having an energy range exceeding 220 MeV and less than or equal to 250 MeV.

The beam turning trajectories 78, along which ion beams of an energy of 35 MeV or less respectively turn, are annular beam turning trajectories centered around the injection electrode 18. The beam turning trajectories 78, along which ion beams of an energy exceeding 35 MeV respectively turn, are annular beam turning trajectories which are eccentric from the injection electrode 18. As a result, between the injection electrode 18 and the septum magnet 19, the centers of the beam turning trajectories 78 of ion beams of an energy exceeding 35 MeV are offset away from the inlet of the beam extraction path 20, and gaps between the beam turning trajectories 78 are narrow on an inlet side of the beam extraction path 20. Particularly, the beam turning trajectories 78 of ion beams of an energy exceeding 60 MeV are concentrated in a predetermined range on the inlet side of the beam extraction path 20. In a region that is positioned 180° opposite to the inlet of the beam extraction path 20 relative to the injection electrode 18, gaps between the beam turning trajectories 78 of ion beams of an energy exceeding 35 MeV are increased to the extent that the gaps between the beam turning trajectories 78 are decreased between the injection electrode 18 and the inlet of the beam extraction path 20.

The protons, which have passed through the ion injection tube 3A and have been bent toward the horizontal direction in the beam turning region 76 by the injection electrode 18, form an ion beam of a low energy, and the ion beam turns along a beam turning trajectory along which an ion beam of a low energy turns. The ion beam is accelerated in the portion of the radiofrequency acceleration electrode 9C (to which a radiofrequency voltage has been applied) between the bent points 24M and 24N and the tip end, and in the portion of the radiofrequency acceleration electrode 9D (to which a radiofrequency voltage has been applied) between the bent points 24O and 24P and the tip end. The accelerated ion beam moves to one of the beam turning trajectories 78 positioned outside the aforementioned beam turning trajectory. For example, an ion beam of 10 MeV turning along the beam turning trajectory 78 of an ion beam of 10 MeV is accelerated in the aforementioned portions of the radiofrequency acceleration electrodes 9C and 9D. The accelerated ion beam moves to the beam turning trajectory 78 of an ion beam of 11 MeV, and turns along the beam turning trajectory 8. In this manner, the turning ion beam is accelerated and sequentially moves to the outside beam turning trajectories 78, for example, moves to the beam turning trajectory 78 of an ion beam of 119 MeV. An ion beam of 119 MeV turning along this beam turning trajectory 78 is accelerated by the radiofrequency acceleration electrodes 9A to 9D, and moves to the outside beam turning trajectory 78 of an ion beam of 220 MeV.

An ion beam of 220 MeV turning along the beam turning trajectory 78 of an ion beam of 220 MeV is ejected from the beam turning trajectory 78 by the massless septum 12, that is, is separated from the beam turning trajectory 78, and then the ion beam of 220 MeV is extracted to the beam path 48 of the beam transport 13 through the beam extraction path 20 formed in the septum magnet 19. An ion beam of 140 MeV turning along the beam turning trajectory 78 of an ion beam of 140 MeV is ejected therefrom by the massless septum 12, and then the ion beam of 140 MeV is extracted to the beam path 48 through the beam extraction path 20. As such, the accelerator 4 of the ion beam generator 2 is capable of extracting ion beams of different energies. The beam turning trajectories 78 are offset toward the inlet of the beam extraction path 20 and the gaps between the beam turning trajectories 78 are narrow between the injection electrode 18 and the inlet of the beam extraction path 20. The gaps between the beam turning trajectories 78 are wide in the region that is positioned 180° opposite to the inlet of the beam extraction path 20 relative to the injection electrode 18. As a result, the aforementioned extraction of ion beams can be realized. Particularly, in the eccentric trajectory region (to be described later), concentration of multiple beam turning trajectories 78 (along which ion beams of different energies turn) on the inlet side of the beam extraction path 20 contributes to extraction of the ion beams of different energies. The function of the massless septum 12 will be described in detail later.

In the accelerator 4 of the embodiment, the following trajectory regions are formed on the median plane 77 on which the beam turning trajectories 78 are formed in the beam turning region 76: the concentric trajectory region (for example, as illustrated in FIG. 10, a region that contains the beam turning trajectory 78 along which an ion beam of 35 MeV turns, and is positioned inside the beam turning trajectory 78) in which multiple concentric annular beam turning trajectories are formed around the injection electrode 18 (the ion inlet port of the ion injection tube 3A); and the eccentric trajectory region (for example, as illustrated in FIG. 10, a region that is positioned outside the beam turning trajectory 78 along which an ion beam of 35 MeV turns) which surrounds the concentric trajectory region and in which multiple annular beam turning trajectories having the respective eccentric centers are formed, gaps between the annular beam turning trajectories are narrow between the injection electrode 18 and the inlet of the beam extraction path 20, and the gaps between the annular beam turning trajectories are wide in the region that is positioned 180° opposite to the inlet of the beam extraction path 20 relative to the injection electrode 18.

The bent points 24M to 24P, which are formed in the radiofrequency acceleration electrodes 9C and 9D disposed inside the vacuum chamber 27, are positioned at the position of the beam turning trajectory 78 along which an ion beam of 35 MeV turns illustrated in FIG. 10.

In the accelerator 4, a change in the gap between the magnetic pole 7E of the return yoke 5A and the facing magnetic pole 7E of the return yoke 5B along an isochronous line $IL_1$ is illustrated in FIG. 11, a change in the gap between the magnetic pole 7C of the return yoke 5A and the facing magnetic pole 7C of the return yoke 5B along an isochronous line $IL_2$ is illustrated in FIG. 12, and a change in the gap between the magnetic pole 7A of the return yoke 5A and the facing magnetic pole 7A of the return yoke 5B along an isochronous line $IL_3$ is illustrated in FIG. 13. Gaps illustrated in FIGS. 11, 12, and respectively represent half the gap between the facing magnetic poles 7E, half the gap between the facing magnetic poles 7C, and half the gap between the facing magnetic poles 7A. These gaps are respectively equivalent to a gap between the magnetic pole 7E and the median plane 77, a gap between the magnetic pole 7C and the median plane 77, and a gap between the magnetic pole 7A and the median plane 77. The isochronous lines $IL_1$, $IL_2$, and $IL_3$ are illustrated in FIGS. 3 and 10. The isochronous lines $IL_1$, $IL_2$, and $IL_3$ are respectively equivalent to the center lines of the magnetic poles 7E, 7C, and 7A.

As illustrated in FIG. 11, the gap between the magnetic pole 7E and the median plane 77 becomes the minimum value when the gap is positioned from the tip end of the magnetic pole 7E in a preferable range of 93.0% to 96.0% of the length between the tip end (facing the injection electrode 18) of the magnetic pole 7E and the end surface (facing the inner surface of the annular coil 11B) of the magnetic pole 7E along the isochronous line $IL_1$. This implies that the center line height (the height of the magnetic pole 7E from the bottom surface 95 of each of the recesses 29D and 29E) of the magnetic pole 7E in the direction of the central axis C becomes the maximum value at a position in this range. Similar to the magnetic pole 7E, the center line height (the height of the magnetic pole 7F from the bottom surface 95 of each of the recesses 29C and 29D) of the magnetic pole 7F disposed symmetrical with the magnetic pole 7E relative to the alternate long and short dash line X) in the direction of the central axis C becomes the maximum value when a portion of the magnetic poles 7F is positioned from the tip end facing the injection electrode 18 in the aforementioned range relative to the center line length of the magnetic pole 7F.

As illustrated in FIG. 12, the gap between the magnetic pole 7C and the median plane 77 becomes the minimum value when the gap is positioned from the tip end of the magnetic pole 7C in a preferable range of 86.2% to 89.2% of the length between the tip end (facing the injection electrode 18) of the magnetic pole 7C and the end surface (facing the inner surface of the annular coil 11B) of the magnetic pole 7C along the isochronous line $IL_2$. This implies that the center line height (the height of the magnetic pole 7C from the bottom surface 95 of each of the recesses 29E and 29F) of the magnetic pole 7C in the direction of the central axis C becomes the maximum value at a position in this range. Similar to the magnetic pole 7C, the center line height (the height of the magnetic pole 7B from the bottom surface 95 of each of the recesses 29B and 29C) of the magnetic pole 7D (disposed symmetrical with the magnetic pole 7C relative to the alternate long and short dash line X) in the direction of the central axis C becomes the maximum value when a portion of the magnetic poles 7D is positioned from the tip end facing the injection electrode 18 in the aforementioned range relative to the center line length of the magnetic pole 7D.

As illustrated in FIG. 13, the gap between the magnetic pole 7A and the median plane 77 becomes the minimum value when the gap is positioned from the tip end of the magnetic pole 7A in a preferable range of 88.7% to 91.7% of the length between the tip end (facing the injection electrode 18) of the magnetic pole 7A and the end surface (facing the inner surface of the annular coil 11B) of the magnetic pole A along the isochronous line $IL_3$. This implies that the center line height (the height of the magnetic pole 7A from the bottom surface 95 of each of the recesses 29A and 29F) of the magnetic pole 7A in the direction of the central axis C becomes the maximum value at a position in this range. Similar to the magnetic pole 7A, the center line height (the height of the magnetic pole 7B from the bottom surface 95 of each of the recesses 29A and 29B) of the magnetic pole 7B (disposed symmetrical with the magnetic pole 7A relative to the alternate long and short dash line X) in the direction of the central axis C becomes the maximum value when a portion of the magnetic poles 7B is positioned from the tip end facing the injection electrode 18 in the aforementioned range relative to the center line length of the magnetic pole 7B. The position of the bottom surface 95 of the recess 29E in the direction of the central axis C is the same as that of the bottom surface 95 of each of the recesses 29A to 29C and 29F in the direction of the central axis C, which is not illustrated.

In the return yoke 5A, the center line height of each of the magnetic poles 7E and 7F in the direction of the central axis C becomes the maximum value at a position in the aforementioned range of the magnetic poles 7E and 7F of the return yoke 5B. In the return yoke 5A, the center line height of each of the magnetic poles 7C and 7D in the direction of the central axis C becomes the maximum value at a position in the aforementioned range of the magnetic poles 7C and 7D of the return yoke 5B. In the return yoke 5A, the center line height of each of the magnetic poles 7A and 7B in the direction of the central axis C becomes the maximum value at a position in the aforementioned range of the magnetic poles 7A and 7B of the return yoke 5B.

As a result, as illustrated in FIG. 10, in the magnetic field strength distribution on the median plane 77 between the return yokes 5B and 5A, magnetic field strength between the magnetic poles 7E and 7F of the return yoke 5B and the facing magnetic poles 7E and 7F of the return yoke 5A becomes the maximum value of 2.2 T at a position in the aforementioned range, magnetic field strength between the magnetic poles 7C and 7D of the return yoke 5B and the facing magnetic poles 7C and 7D of the return yoke 5A becomes the maximum value of 2.2 T at a position in the aforementioned range, and magnetic field strength between the magnetic poles 7A and 7B of the return yoke 5B and the facing magnetic poles 7A and 7B of the return yoke 5A becomes the maximum value of 2.2 T at a position in the aforementioned range. Accordingly, as illustrated in FIG. 10, magnetic field strength on the median plane 77 becomes the maximum value at the position of each of the beam turning trajectories 78 of ion beams of 200 MeV and 180 MeV in a region in which the magnetic poles 7A to 7F are disposed and which is positioned inside the inner surfaces of the annular coils 11A and 11B. Due to such a magnetic field strength distribution, a convergence force can be applied in a direction perpendicular to the beam turning trajectories, and ion beams are capable of stably turning along the beam turning trajectories 78.

In the accelerator 4 of the embodiment, the magnetic field distribution on the median plane 77 is not uniform, and thus, the formed beam turning trajectories 78 have an annular shape, and do not have a perfect circular shape. As described above, in the iron cores 14A and 14B, magnetic field strength at the positions of the magnetic poles (protrusions) 7A to 7F is higher than that at the positions of the recesses 29A to 29F, and thus, the curvatures of beam turning trajectories between facing magnetic poles respectively formed in the iron cores 14A and 14B are increased. Six pairs of the facing magnetic poles are disposed for one turn of the beam turning trajectory 78. For this reason, each of the beam turning trajectories has a shape in which corners of a substantially hexagonal shape are positioned on the beam turning trajectory. In FIG. 14, this tendency becomes stronger by the extent of the increase in the amplitude of magnetic field strength along a beam turning trajectory. In a case the amplitudes of magnetic field strength are the same, this tendency becomes strong because bending of an ion beam becomes easier by the extent of the decrease in the energy of a beam turning trajectory. The center of a beam turning trajectory which does not have a perfect circular shape is the center of gravity of the shape of the trajectory, and is an arithmetic mean point of coordinates of the trajectory.

In a typical cyclotron, to the extent that beam turning trajectories are present close to the outer circumference, bending of ion beams becomes difficult as the energies of the ion beams are increased, and dense formation of the ion beams becomes difficult. For this reason, it is necessary to increase the amplitudes of magnetic field strength along the beam turning trajectories illustrated in FIG. 14. That is, typically, the accelerator is designed such that radial magnetic field strength along the center line of each of the magnets becomes the maximum value on a beam turning trajectory (the outermost circumferential beam turning trajectory) of the maximum energy.

Characteristics of the accelerator 4 in the embodiment will be described with reference to FIGS. 14 to 21. Hereinafter, unless specified, the direction perpendicular to the central axis C is referred to as a "horizontal direction", and the direction of the central axis C, that is, the direction perpendicular to the median plane 77 is referred to as a "vertical direction".

FIG. 14 illustrates magnetic field strength distributions along four beam turning trajectories 78 along which an ion beam of 0.5 MeV, an ion beam of 70 MeV, an ion beam of 160 MeV, and an ion beam of 235 MeV respectively turn. A position for an advance distance of "0" represents the position of an intersection between each of the beam turning trajectories 78 and the straight line (the alternate long and short dash line X) (connecting the inlet of the beam extraction path 20 to the central axis C) in the vicinity of the inlet (extraction port of the accelerator 4) of the beam extraction path 20 formed in the septum magnet 19. The position for an advance distance of "1" represents a half turn position of an ion beam which is away from the extraction port of the accelerator 4 along the beam turning trajectory 78. Since magnetic field strength along the beam turning trajectory 78 for each of the beam turning trajectories 78 is changed as illustrated in FIG. 14, a convergence force (amplitude) can be ensured, and ion beams of energies are capable of stably turning along the respective beam turning trajectories 78. For the beam turning trajectory 78 along which an ion beam of 235 MeV turns, a convergence force is ensured in a magnetic field strength distribution which is not a simple sinusoidal wave, and the ion beam is capable of stably turning along the beam turning trajectory. Specifically, a magnetic field is formed on the beam turning trajectory of an ion beam of 235 MeV such that, among six maximum peaks of the strength of the magnetic field through which the ion beam passes during one turn, maximum peaks positioned second and fifth from the position for an advance distance of 0 are lower than others, and the values of minimum peaks on both sides of the maximum peaks are higher than others. For this reason, a change in the amplitude of the magnetic field strength along the beam turning trajectory of an ion beam of 235 MeV is smaller than that of the beam turning trajectory of an ion beam of 160 MeV.

FIG. 15 illustrates changes in the gradients of normalized magnetic fields along the respective beam turning trajectories 78. A normalized magnetic field represents an n value in Expression (1).

$$n = \frac{B\rho}{B^2} \frac{\partial B_z}{\partial r} \qquad (1)$$

B represents magnetic field strength, Bρ represents magnetic rigidity of an ion beam, and $B_z$ represents a vertical component of a magnetic field. r represents a vertical position coordinate with respect to a beam turning trajectory on a trajectory plane which is the median plane 77, and an outward direction is considered to be positive. When n is less than one, an ion beam turning along a beam turning trajectory converges in the horizontal direction, and when n is greater than zero, an ion beam turning along a beam turning trajectory converges in the vertical direction.

In three beam turning trajectories 78 along which an ion beam of 70 MeV, an ion beam of 160 MeV, and an ion beam of 235 MeV respectively turn, an n value at the position (half turn position from each intersection which will be described later) for an advance distance of "1" is a small value. In contrast, the absolute value of an n value is increased in the vicinity of positions for an advance distance of "0" on the beam turning trajectories 78, which are the positions of the intersections between the beam turning trajectories 78 and the straight line (the alternate long and short dash line X) (connecting the inlet of the beam extraction path 20 to the central axis C) in the vicinity of the inlet (extraction port of the accelerator 4) of the beam extraction path 20. As described above, at the position for an advance distance of "0", the beam turning trajectories are concentrated, and gaps between adjacent beam turning trajectories are small. As a result, a magnetic field gradient, that is, the absolute value of an n value is increased. In contrast, the absolute value of a magnetic field gradient is decreased at the position (half turn position) for an advance distance of "1" at which gaps between adjacent beam turning trajectories are large. As such, a horizontal convergent action and a vertical convergent action are alternately exerted on ion beams turning along the respective beam turning trajectories, and thus, the ion beams are capable of stably turning in the horizontal and vertical directions.

The characteristics illustrated in FIG. 15 imply the following concept. The integrated absolute value of an n value (represented in Expression (2)) for a semicircle (the sum of a ¼ circle formed in a clockwise direction starting from the position for an advance distance of "1" and a ¼ circle formed in a counter-clockwise direction starting from the position for an advance distance of "1") of each of the annular beam turning trajectories 78, the midpoint of which is a position (position for an advance distance of "1") 180° opposite to the inlet of the beam extraction path 20 with respect to the central axis C, is less than the integrated absolute value of an n value for a semicircle (the sum of a ¼ circle formed in the clockwise direction starting from the position for an advance distance of "0" and a ¼ circle formed in the counter-clockwise direction starting from the position for an advance distance of "0") of the annular beam turning trajectory 78, the midpoint of which is the intersection (position for an advance distance of "0") on the inlet side of the beam extraction path 20.

The integrated absolute value of an n value (represented in Expression (1)) for a semicircle of an annular beam turning trajectory, the midpoint of which is the position 180° opposite to the inlet of the beam extraction path, is less than the integrated absolute value of an n value for a semicircle of the beam turning trajectory, the midpoint of which is the inlet of the beam extraction path. As a result, it is possible to efficiently extract ion beams of different energies, and in a case where beam turning trajectories of different energies are densely formed on the inlet side of the beam extraction path while being eccentric with each other, the dense formation allows a reduction in the gradients of magnetic fields generated on the inlet side of the beam extraction path.

Hereinafter, a magnetic field distribution will be described in detail. Magnetic field strength B ($L_1$) at a position on a beam turning trajectory 78 is represented by Expression (2).

$$B(L_1)=B_0+B_1\cos(2\pi L_1/L_2)+B_2\cos(4\pi L_1/L_2)+B_3\cos(6\pi L_1/L_2) \quad (2)$$

B represents magnetic field strength, $L_1$ represents the advance distance of an ion beam along the beam turning trajectory, $L_2$ represents the length of a semicircle of the beam turning trajectory, $B_0$ represents a median value (average magnetic field strength exerted on the ion beam) of the magnetic field strength, and $B_1$, $B_2$, and $B_3$ represent Fourier expansion coefficients of the magnetic field strength of the beam turning trajectories 78 of energies. When the length of the semicircle of the beam turning trajectory is taken as a reference wavelength, $B_1$ represents a radiofrequency amplitude, $B_2$ represents a double radiofrequency amplitude, and $B_3$ represent a triple radiofrequency amplitude.

In the embodiment, as illustrated in FIG. 16, in a case where the kinetic energy of an ion beam is approximately 180 MeV or higher, the triple radiofrequency magnetic field component $B_3$ is increased, and, at the same time, the double radiofrequency magnetic field component $B_2$ is decreased. For this reason, on the beam turning trajectory 78 along which an ion beam of an energy of 180 MeV or higher, it is possible to ensure a convergence force of the ion beam without increasing the maximum magnetic field. The triple radiofrequency magnetic field component $B_3$ is the concentric trajectory region.

FIG. 17 illustrates a change in a betatron oscillation frequency in the horizontal and vertical directions versus the kinetic energy of an ion beam. The betatron oscillation frequency is substantially simply increased in the horizontal direction as the kinetic energy of the ion beam is increased. The change magnitude of the betatron oscillation frequency is 0.6 or less in a kinetic energy range of 0 MeV to 250 MeV. A beam turning trajectory is biased in the vertical direction in the vicinity of a kinetic energy of 50 MeV, and even if the kinetic energy is increased, the betatron oscillation frequency converges to 0.5 or less in the vertical direction. For this reason, ion beams are capable of stably turning in the beam turning region 76 that is formed between facing magnetic poles and between facing radiofrequency acceleration electrodes illustrated in FIG. 6. Ion beams are capable of stably passing though the beam passage 35 formed in the massless septum 12 illustrated in FIG. 7.

FIG. 18 illustrates a change in a horizontal β function along each of the beam turning trajectories 78 for a half turn (advance distance of an ion beam: 1) from an intersection (advance distance of an ion beam: 0) between the straight line straight line (the alternate long and short dash line X) (connecting the central axis C to the inlet of the beam extraction path 20) and each of the beam turning trajectories 78 (along which ion beams of 0.5 MeV, 70 MeV, 160 MeV, and 235 MeV respectively turn) in the vicinity of the inlet of the beam extraction path 20. A β function represents the amount of a spatial extent of an ion beam. The massless septum 12 is disposed at the position at which the advance distance of an ion beam is 1.

In FIG. 18, the horizontal β function is 10 m or less at the position at which the massless septum 12 is disposed. As a result, it is possible to separate the beam turning trajectories 78 from each other along which the ion beams of 0.5 MeV, 70 MeV, 160 MeV, and 235 MeV respectively turn. For this reason, it is possible to separately eject the ion beams of the energies via the massless septum 12, and to extract the ion beams from the accelerator 4 into the beam transport 13.

FIG. 19 illustrates a change in a vertical β function along each of the beam turning trajectories 78 for a half turn (advance distance of an ion beam: 1) from an extraction port (advance distance of an ion beam: 0) of each of the beam turning trajectories 78 along which ion beams of 0.5 MeV, 70 MeV, 160 MeV, and 235 MeV respectively turn. The vertical β function of each of the ion beams of 70 MeV, 160 MeV, and 235 MeV extracted from the accelerator 4 is 3 m or less at the position at which the massless septum 12 is disposed and the advance distance of each ion beam is 1. As a result, the ion beams of the energies are capable of easily passing through the beam passage 35 of the massless septum 12. The vertical β function between the extraction port of each of the beam turning trajectories 78 and the half turn position is 100 m or less which is a limit in which the ion beams do not collide with the magnetic poles inside the accelerator 4. As a result, the ion beams are capable of stably turning in the beam turning region 76 formed between facing magnetic poles and between facing radiofrequency acceleration electrodes without colliding the magnetic poles and the radiofrequency acceleration electrodes.

FIG. 20 illustrates the amount of ejection (caused by excitation of the magnetic poles of the massless septum 12) of each ion beam turning along the beam turning trajectory 78 versus the kinetic energy of the turning ion beam when the ion beam is extracted from the accelerator 4. In FIG. 10, the inlet of the beam extraction path 20 formed in the septum magnet 19 is positioned −720 mm from the center of a beam turning trajectory of the minimum energy. The energy of each ion beam extracted from the accelerator 4 is 70 MeV or higher. A "trajectory position" illustrated in FIG. 20 represents the position of the beam turning trajectory 78 through which each ion beam, which has not been ejected by the massless septum 12, passes, which is closest to the inlet of the beam extraction path 20, and is present in the vicinity of the inlet of the beam extraction path 20. The amount of offset between the trajectory position illustrated in FIG. 20 and the inlet of the beam extraction path 20 represents the amount of trajectory displacement caused by ejection of a turning ion beam from the beam turning trajectory 78 via the massless septum 12. The amount of ejection of a turning ion beam is increased by the extent of the decrease in the energy of the ion beam. An excitation current supplied to the coils 33A and 33B, which are respectively provided on a pair of the corresponding magnetic poles 32A and 32B of the massless septum 12, is adjusted according to the amount of ejection.

A pair of the magnetic poles 32A and 32B of the massless septum 12 generates magnetic lines of force (magnetic lines of force from the magnetic pole 32B toward the magnetic pole 32A) in the same direction as a direction of magnetic lines of force generated in the recesses 29A of the return yokes 5A and 5B in which the massless septum 12 is disposed, and the pair of magnetic poles 32A and 32B is excited to intensify a magnetic field. A magnetic field peak illustrated in FIG. 22 is formed at a predetermined position which is present in the beam passage 35 formed in the massless septum 12 and on the median plane 77 in the radial direction of the vacuum chamber 27. The position of the magnetic field peak corresponds to the position of any one of the 28 pairs of magnetic poles 32A and 32B which are formed in the massless septum 12 and can be selectively excited. The curvature of an ion beam, which passes through a region in the beam passage 35 in which a magnetic field is locally intensified and which is formed by exciting the pair of magnetic poles 32A and 32B of the massless septum 12, is increased compared to the curvature of the beam turning trajectory 78. For this reason, betatron oscillation of the ion beam in the horizontal direction is amplified by the extent of the excitation amount and the width of the massless septum 12, and the ion beam is ejected inward from the beam turning trajectory 78 along which the ion beam turns, and is separated from the beam turning trajectory 78. Since it is possible to adjust the position of a pair of the magnetic poles 32A and 32B to be excited in the radial direction by moving the massless septum in the radial direction via the movement apparatus 17, similar to a case in which 28 or more pairs of the magnetic poles 32A and 32B are provided in the massless septum 12, it is possible to accurately adjust the position of occurrence of the peak of magnetic field strength in the beam passage 35.

FIG. 21 illustrates a horizontal displacement of each of an ejected ion beam of 70 MeV, an ejected ion beam of 160 MeV, and an ejected ion beam of 235 MeV from the respective beam turning trajectories in the beam turning region 76 from when the ion beams of the energies are ejected by the massless septum 12 until the ion beams of the energies ejected from the massless septum 12 reach the inlet of the beam extraction path 20 formed in the septum magnet 19. Unlike other drawings, in FIG. 21, the massless septum 12 is disposed at the position at which the advance distance of an ion beam is "0", and the inlet (ion beam extraction position) of the beam extraction path 20 is positioned at the position (half turn position from the massless septum 12) at which the advance distance of an ion beam is "1". A positive horizontal displacement value implies that an ejected ion beam is displaced toward the outside of the beam turning trajectory 78, and a negative horizontal displacement (displacement on the median plane 77) value implies that an ejected ion beam is displaced toward the inside of the beam turning trajectory 78. An ion beam, which has been ejected toward the inside of a beam turning trajectory by the massless septum 12, is displaced inward to some extent, and then, is greatly displaced toward the outside of the beam turning trajectory according to betatron oscillation in the horizontal direction. The massless septum 12 is controlled such that the absolute value of a horizontal displacement of an ejected ion beam is increased to the extent that the energy of a turning ion beam is decreased. An outward displacement of the beam turning trajectory is increased at the ion beam extraction position. As illustrated in FIG. 21, the reason distances between the inlet of the beam extraction path 20 and the beam turning trajectories 78, along which ion beams of different energies respectively turn, are different from each other is that distances between the septum magnet 19 and the beam turning trajectories 78 of the ion beams of the energies are different from each other as illustrated in FIG. 20.

Due to the characteristics illustrated in FIGS. 14 to 21, the accelerator 4, in which the concentric trajectory region and the eccentric trajectory region are formed, is capable of stably turning ion beams of energies along the respective beam turning trajectories 78, and is capable of continuously extracting ion beams of different energies with which layers, into which a target volume (with which ion beams are irradiated) is divided and which are positioned at different depths, can be irradiated.

A particle beam irradiation method of the particle beam irradiation system will be described with reference to FIGS. 23 to 26.

Before a target volume of the patient 56 is irradiated with ion beams and is treated, treatment planning data is prepared for the patient 56 using treatment planning system 73. The treatment planning data contains data regarding a patient identification number, the number of layers into which a target volume is divided from the body surface of the patient in a depth direction, the energy of an ion beam with which each layer is irradiated, an irradiation direction of an ion beam, an irradiation point (spot point) inside each layer, an ion beam dose for the irradiation point inside each layer, and the like. The treatment planning data prepared by the treatment planning system 73 is stored in the database 72 which is a storage apparatus.

The CPU 67 reads the treatment planning data regarding the patient 56 to be treated here from the database 72 based on input patient identification information, and stores the treatment planning data in the memory 68. The memory 68 stores the value of an excitation current which is supplied to the quadrupole magnets 46, 47, 49, and 50 of the beam transport 13 and the bending magnets 41 to 44 to correspond to the energies (for example, 70 MeV to 235 MeV) of irradiating ion beams; position information regarding beam turning trajectories, along which the ion beams of energies respectively turn, on the median plane 77 inside the accelerator 4; and the value of an excitation current which is supplied to the coils 33A and 33B, which are respectively wrapped around the magnetic poles 32A and 32B of the massless septum 12, when the ion beams turning along the beam turning trajectories are ejected.

In order to treat the target volume of the patient 56, the CPU 67, which is a control information preparation apparatus, prepares control command information used to control the magnets of the beam transport 13 and the massless septum 12 based on the treatment planning data, the value of the excitation current supplied to the magnets of the beam transport 13, the position information regarding the beam turning trajectories, and the value of the excitation current supplied to the coils 33A and 33B of the massless septum 12.

The memory 68 stores the sequence of steps illustrated in FIG. 23. The CPU 67 outputs the control command information to control apparatuses included in each of accelerator and transport control apparatus 69 and the scanning control apparatus 70, based on the sequence.

An excitation current is supplied to the annular coils and the trim coils (Step S1). The coil current control apparatus 94 receives the control command information from the CPU 67, and controls the power supplies 37 and the power supply 57 so as to execute Step S1. As described above, an excitation current is supplied from the power supplies 37 to the respective trim coils 8A to 8F, and the magnetic poles 7A t 7F are excited. An excitation current is supplied from the power supply 57 to the annular coils 11A and 11B, and the iron cores 14A and 14B are excited. As a result, magnetic lines of force are generated in the iron cores 14A and 14B. An annular coil current and a trim coil current illustrated in FIG. 25 respectively flow through the annular coils 11A and 11B and the trim coils 8A to 8F. The vacuum pump 25 is driven all the time such that air inside the vacuum chamber 27 is discharged via the suction tube 26 and a vacuum state inside the vacuum chamber 27 is maintained. Through portions of the return yokes 5A and 5B of the vacuum chamber 27 for the waveguide tubes, the lead-out wirings, and the operation members 16 and 16A are sealed with sealing members such that sealability is maintained.

The ion source is started (Step S2). The accelerator and transport control apparatus 69 receives the control command information from the CPU 67, and starts and controls the ion source 3.

A radiofrequency voltage is supplied to the radiofrequency acceleration electrodes (Step S3). In order to execute Step S3, the radiofrequency voltage control apparatus 99 adjust a radiofrequency voltage applied to the radiofrequency acceleration electrodes 9A to 9D by controlling the radiofrequency power supplies 36 based on the control command information from the CPU 67. As a result, as described above, a radiofrequency voltage is applied to the radiofrequency acceleration electrodes 9A to 9D. A radiofrequency voltage having a frequency illustrated in FIG. 25 is applied to the radiofrequency acceleration electrodes 9A to 9D.

A voltage is applied to the injection electrode (Step S4). In order to execute Step S4, the injection magnet control apparatus 83 applies a voltage to the injection electrode 18 by controlling the power supply 80 based on the control command information from the CPU 67. Due to the application of a voltage to the injection electrode 18, the ion source 3 injects ions (protons) into the ion injection portion 109 (formed in the beam turning region 76) through the ion inlet port formed at the tip end of the ion injection tube 3A. The injected ions are bent toward the horizontal direction by the injection electrode 18, are accelerated in the connection portion between the radiofrequency acceleration electrodes 9C and 9D which are positioned close to the ion injection portion 109, and are started to turn in a counter-clockwise direction.

An ion beam turns inside the accelerator until the energy of the ion beam is increased to a set energy (Step S5). The injected ions form an ion beam, and in a state where the magnetic poles 7A to 7F and the annular coils 11A and 11B are excited, first, the ion beam is accelerated to an energy of 70 MeV by the radiofrequency acceleration electrodes 9C and 9D to which radiofrequency voltage have been applied. The ion beam is accelerated four times by the two radiofrequency acceleration electrodes during one turn of each of beam turning trajectories of energies of 70 MeV or less. In a region having an energy exceeding 70 MeV, the radiofrequency acceleration electrodes 9A and 9B, to which a radiofrequency voltage has been applied, also contribute to acceleration of the ion beam. As a result, the ion beam is accelerated to an energy of 220 MeV by the radiofrequency acceleration electrodes 9A to 9D. The ion beam is accelerated eight times by the four radiofrequency acceleration electrodes during one turn of each of beam turning trajectories of energies exceeding 70 MeV. The accelerated ion beam turns along the beam turning trajectories 78 on the median plane 77 inside the accelerator 4, and the energy of the ion beam is increased to the set energy (for example, 250 MeV). At a position at which the massless septum 12 is disposed, the ion beams turning along the beam turning trajectories 78 for ion beams of 70 MeV to 250 MeV illustrated in FIG. 10 pass through the beam passage 35 formed between facing magnetic poles 32A and 32B of the massless septum 12.

The target volume of the patient 56 is irradiated with an ion beam having an energy of 70 MeV or higher for treatment. The ion beam having an energy of 70 MeV or higher is an ion beam having the minimum energy among ion beams with which the target volume, which is a target for irradiation, is irradiated.

Ion beams turning along the beam turning trajectories are measured (Step S6). In order to execute Step S6, the beam current measuring unit control apparatus 84 controls the movement apparatus 17A based on the control command information from the CPU 67. The movement apparatus 17A is driven by this control such that the operation member 16A is moved. Typically, the beam current measuring unit 15, which is pulled out to a position between the annular coils 11A and 11B, reaches the inside of the beam passage 35 through the through hole 31D of the connection portion 31C due to the movement of the operation member 16A, and is moved toward the injection electrode 18 along the alternate long and short dash line X on the median plane 77. While being moved toward the injection electrode 18, the beam current measuring unit 15 measures a beam current of an ion beam turning along each of the beam turning trajectories 78 (for example, as illustrated in FIG. 10, from the beam turning trajectory 78 along which an ion beam of 250 MeV turns to the beam turning trajectory 78 along which an ion beam of 70 MeV turns) for each of the beam turning trajectories 78. The beam current values measured by the beam current measuring unit 15 are respectively equivalent to the energies of the ion beams turning along the beam turning trajectories 78. Energy information items corresponding to the measured beam current values are sent to the beam current measuring unit control apparatus 84. The position of the beam current measuring unit 15 toward the injection electrode 18 for each of the beam turning trajectories 78 is detected by the position detector 39. Position information regarding the beam current measuring unit 15 detected by the position detector 39, that is, position information items regarding the positions of the beam turning trajectories 78 in the radial direction of the annular coils is sent to the beam current measuring unit control apparatus 84. The beam current measuring unit control apparatus 84 stores the energy information items corresponding to the measured beam current values and the position information items regarding the beam turning trajectories 78 in the memory 107 of the accelerator and transport control apparatus 69 in a state where the energy information items are respectively associated with the position information items. FIG. 24 illustrates an example of information in which the energy information items are respectively associated with the beam turning trajectories 78.

It is determined whether the beam turning trajectories are respectively formed at predetermined positions (Step S23). The coil current control apparatus 94 determines whether the beam turning trajectories 78 are respectively formed on the median plane 77 at the predetermined positions, based on the position information items regarding the beam turning trajectories 78 which are read from the memory 107.

The excitation current supplied to the trim coils is adjusted (Step S24). When at least one beam turning trajectory 78 among the beam turning trajectories 78 is offset from the predetermined position, the determination result of Step S23 is considered to be "No". In this case, in order for the beam turning trajectory 78 (has been offset from the predetermined position) to be formed at the predetermined position, the coil current control apparatus 94 adjusts the excitation current supplied to the trim coils 8A to 8F by controlling the power supplies 37 which are respectively connected to the trim coils 8A to 8F installed on the magnetic poles 7A to 7F. The position of a beam turning trajectory is corrected by adjusting an excitation current.

Thereafter, each of Steps S6 and S23 is executed. When the determination result of Step S23 is considered to be "No", each of Steps S24, S6, and S23 is repeated until the determination result of Step S23 becomes "Yes". When all of the beam turning trajectories 78 are respectively formed on the median plane 77 at the predetermined positions, the determination result of Step S23 becomes "Yes", and Step S7 is executed.

Excitation amounts of the septum magnet and each magnet of the beam transport are adjusted (Step S7). In order to execute Step S7, the magnet control apparatus 85 adjusts the excitation current, which is supplied to the septum magnet 19, to an excitation current corresponding to the energy (for example, 250 MeV) of an ion beam to be extracted by controlling the power supply 82 based on the control command information from the CPU 67. The septum magnet 19 is excited by the excitation current. The magnet control apparatus 85 adjusts the excitation current, which is supplied to the quadrupole magnets 46, 47, 49, and 50 and the bending magnets 41 to 44 of the beam transport 13, to an excitation current corresponding to an energy (for example, 250 MeV) of an ion beam to be extracted by controlling the separate power supplies (not illustrated) based on the control command information. The quadrupole magnets and the bending magnets are excited by the excitation current. The septum magnet 19 and each magnet provided in the beam transport 13 are excited such that the ion beam of 250 MeV can be transported to the extraction system 7.

The positions of the magnetic poles of the massless septum are adjusted (Step S8). In order to execute Step S8, based on the control command information from the CPU 67, the massless septum control apparatus 86 controls the movement apparatus 17 such that the movement apparatus 17 moves the operation member 16. As a result, the massless septum 12 is moved toward the injection electrode 18 along the alternate long and short dash line X in the radial direction of the vacuum chamber 27 from a position that is 180° opposite to the inlet of the beam extraction path 20 relative to the central axis C of the vacuum chamber 27. The massless septum 12 can be moved approximately 10 mm by the movement apparatus 17. The massless septum 12 is moved this distance so as to finely perform adjustment of the positioning of a pair of facing magnetic poles 32A and 32B. Due to the movement of the massless septum 12, in a region in which gaps between adjacent beam turning trajectories 78 (positioned 180° opposite to the inlet of the beam extraction path 20 relative to the central axis C) are wide, in a state where the massless septum 12 is aligned with the beam turning trajectory 78 along which the ion beam of 250 MeV turns, an injection electrode 18 side corner of each of the pair of magnetic poles 32A and 32B to be excited is aligned with the beam turning trajectory 78. In this case, the position of the massless septum 12 inside the vacuum chamber 27 is a leftmost position of the massless septum 12 illustrated in FIG. 25.

The magnetic poles of the massless septum are excited (Step S9). After the pair of magnetic poles 32A and 32B are aligned with the beam turning trajectory 78 along which the ion beam of 250 MeV turns, in order to execute Step S9, the massless septum control apparatus 86 controls the power supply 40 based on the control command information from the CPU 67. The massless septum control apparatus 86 controls a switch such that the power supply 40 is connected to the wirings 23A and 23B which are respectively connected to the coils 33A and 33B wrapped around the magnetic poles 32A and 32B to be excited. An excitation current is supplied from the power supply 40 to each of the coils 33A and 33B, and the pair of facing magnetic poles 32A and 32B to be excited are excited. Due to the excitation, magnetic lines of force are generated in a magnetic circuit formed by a closed loop from the excited magnetic poles 32A and 32B, to the iron core portion 31B, to the connection portion 31C, to the iron core portion 31A, and to the magnetic pole 32A. Magnetic lines of force from the magnetic pole 32A toward the magnetic pole 32B cross the beam path 35 which is formed between the magnetic poles and through which ion beams pass. Due to action of the magnetic lines of force, the ion beam of 250 MeV is ejected and separated from the beam turning trajectory 78 along which the ion beam turns, and the ion beam of 250 MeV moves toward the inlet of the beam extraction path 20 formed in the septum magnet 19.

Shortly, due to action of the excited septum magnet 19, the ejected ion beam of 250 MeV is extracted to the beam path 48 of the beam transport 13 through the beam extraction path 20. The ion beam is guided to the irradiation apparatus 7 through the beam path 48, and is extracted from the irradiation apparatus 7. At this time, the patient 56 does not lie on the treatment bed 55.

It is confirmed whether the ion beam is extracted from the accelerator (Step S10). The beam point monitor 53 provided in the irradiation apparatus 7 detects the point of the ion beam passing through the irradiation apparatus 7. Detected position information regarding the ion beam is input from the beam point monitor 53 to the ion beam confirmation apparatus 87. When the ion beam confirmation apparatus 87 receives the position information regarding the ion beam, the ion beam confirmation apparatus 87 determines that the ion beam have been extracted from the accelerator 4, and the ion beam confirmation apparatus 87 outputs the determination result to a display apparatus (not illustrated). An operator confirms extraction of the ion beam by observing the determination result displayed on the display apparatus.

The aforementioned description of each of the step of extracting an ion beam from the accelerator is ended.

Hereinafter, in the particle beam irradiation method, each of steps of irradiating layers of a target volume of a patient with ion beams of different energies will be described according to the sequence illustrated in FIG. 26.

After the patient 56 lies on the treatment bed 55, the treatment bed 55 is moved and a target volume is positioned on an extension line of the beam axis of the irradiation apparatus 7.

The rotating gantry is rotated such that the beam axis of the irradiation system is set to be aligned with an irradiation direction of an ion beam toward the target volume (target for beam irradiation) (Step S11). The target volume of the patient 56, on which treatment is performed by irradiating ion beams, is a target for beam irradiation. In order to execute Step S11, the rotation control apparatus 88 controls a rotation apparatus (not illustrated) of the rotating gantry 6 based on the control command information from the CPU 67. The rotation apparatus is driven, and until the beam axis of the irradiation apparatus 7, through which ion beams pass, is set to be aligned with the irradiation direction, the rotating gantry 6 is rotated around the rotational shaft 45 based on the information regarding the irradiation direction of an ion beam which is contained in the treatment planning data.

When the beam axis of the irradiation apparatus 7 coincides with the irradiation direction, the rotation of the rotating gantry 6 is stopped.

One inner layer of the target for beam irradiation, which is irradiated with an ion beam, is set (Step S12). The irradiation point control apparatus 89 sets one inner layer of the target volume which is irradiated with an ion beam, based on the control command information from the CPU 67. The irradiation point control apparatus 89 sets a layer at the most distal position as the one layer based on information regarding multiple divided layers of the target volume contained in the treatment planning data stored in the memory 70. The irradiation point control apparatus 89 retrieves energy information (for example, 220 MeV) regarding an ion beam, with which the set layer is irradiated, from the memory 70. The irradiation point control apparatus 89 outputs the retrieved energy information regarding the ion beam to the massless septum control apparatus 86.

The magnetic poles of the massless septum are positioned (Step S13). Among the multiple magnetic poles 32A and 32B formed in the massless septum 12, one pair of magnetic poles 32A and 32b, which are positioned on the beam turning trajectory 78 of an ion beam of 220 MeV corresponding to the energy (for example, 220 MeV) of the ion beam with which the set layer is irradiated, are positioned closer to the injection electrode 18 than another pair of facing magnetic poles 32A and 32B which have been positioned on the beam trajectory 78, along which the ion beam of 250 MeV turns, in Step S8. The massless septum control apparatus 86 receives information regarding the layer, which has been set by the irradiation point control apparatus 89, from the irradiation point control apparatus 89. Among multiple pairs of magnetic poles 32A and 32B of the massless septum 12, the massless septum control apparatus 86 specifies the pair of magnetic poles 32A and 32B which are positioned on the beam turning trajectory 78 of the ion beam of 220 MeV and are excited, based on the information regarding the energy (220 MeV) of the ion beam (with which the set layer is irradiated) input from the irradiation point control apparatus 89, and the position information (position information regarding the beam current measuring unit 15 which is detected by the position detector 39) regarding the beam turning trajectory 78 which is stored in the memory 107 while being associated with energies. The massless septum control apparatus 86 obtains the amount of movement of the massless septum 12 in the radial direction of the annular coils which is required to position an injection electrode 18 side corner of each of the pair of magnetic poles 32A and 32B, which have been specified based on the position information regarding the beam turning trajectory 78 stored in the memory 107, on the beam trajectory 78 of the ion beam of 220 MeV.

The massless septum control apparatus 86 moves the massless septum 12 toward the injection electrode 18 by controlling the movement apparatus 17 based on the obtained amount of movement of the massless septum 12. Due to this movement, in the region in which gaps between adjacent beam turning trajectories 78 (positioned 180° opposite to the inlet of the beam extraction path 20 relative to the central axis C) are wide, the injection electrode 18 side corner of each of the specified magnetic poles 32A and 32B to be excited is positioned on the beam turning trajectory 78 along which the ion beam of 220 MeV turns. It is possible to confirm the amount of movement of the massless septum 12 when the specified pair of magnetic poles 32A and 32B are positioned, based on position data regarding the massless septum 12 measured by the position detector 38. Step S13 is substantially the same as Step S8.

The magnetic poles of the massless septum are excited (Step S14). After the positioning of the magnetic poles in Step S13 is ended, based on information regarding the specified pair of magnetic poles 32A and 32b, the massless septum control apparatus 86 controls the switch such that the power supply 40 is connected to the wirings 23A and 23B which are respectively connected to the coils 33A and 33B wrapped around the one pair of magnetic poles 32A and 32B to be excited which are positioned in Step S13. The massless septum control apparatus 86 controls the power supply 40 based on the control command information from the CPU 67, such that the power supply 40 outputs an excitation current to obtain the amount of ejection required to inject the ion beam of 220 MeV illustrated in FIG. 20 into the inlet of the beam extraction path 20. The excitation current is supplied to each of the coils 33A and 33B which are respectively wrapped around a pair of facing magnetic poles 32A and 32B to be excited which have been positioned as described above, and the pair of magnetic poles 32A and 32B to be excited are excited. Step S13 is substantially the same as Step S8.

The excitation amount of each of the septum magnet and the magnets of the beam transport is adjusted (Step S7). The magnet control apparatus 85 receives the information regarding the layer, which has been set by the irradiation point control apparatus 89, from the irradiation point control apparatus 89. As described above, based on the energy information (for example, 220 MeV) regarding the ion beam with which the set layer is irradiated, the magnet control apparatus 85 controls the power supply 82 such that the septum magnet 19 is excited by an excitation current corresponding to 220 MeV of the extracted ion beam. As described above, the quadrupole magnets 46, 47, 49, and 50 and the bending magnets 41 to 44 of the beam transport 13 are also excited by an excitation current corresponding to 220 MeV. At this time, the excitation amount of each of the septum magnet 19 and the magnets provided in the beam transport 13 becomes equal to an excitation amount illustrated by the second step from the left in the lowest characteristic graph of FIG. 25.

The scanning magnets are controlled such that the irradiation point of an ion beam inside the set layer is set (Step S15). When the irradiation point control apparatus 89 receives a signal indicating the end of adjustment of the excitation amount of each magnet from the magnet control apparatus 85, based on information regarding an irradiation point inside the set layer contained in the treatment planning data, the irradiation point control apparatus 89 controls an excitation current supplied to each of the scanning magnets 51 and 52 to generate a bending magnetic field in each of the scanning magnets 51 and 52 such that the irradiation point, which is an ion beam target, is irradiated. The bending magnetic field generated in the scanning magnet 51 controls the point of an ion beam in the y direction, which is extracted from the accelerator 4 in Step S16 (to be described later). The bending magnetic field generated in the scanning magnet 52 controls the point of the ion beam in the x direction perpendicular to the y direction, which is extracted from the accelerator 4.

When it is determined that the excitation current supplied to each of the scanning magnets 51 and 52 is controlled for the ion beam to reach the irradiation point which is an ion beam target in Step S15, the irradiation point control apparatus 89 outputs a beam irradiation start signal.

A voltage is applied to the injection electrode (Step S16). Similar to Step S4, when the injection electrode control apparatus 83 receives a beam irradiation start signal from the irradiation point control apparatus 89, the injection electrode control apparatus 83 controls the power supply 80 such that a voltage is applied to the injection electrode 18. Ions, which have been injected into the beam turning region 76 from the ion source 3 via the ion injection tube 3A, are bent toward the horizontal direction by the injection electrode 18, turn on the median plane 77, and are accelerated by the radiofrequency acceleration electrodes 9A to 9D to a radiofrequency voltage is applied. An ion beam turning along the beam turning trajectory 78, along which an ion beam of 220 MeV turns, enters the beam passage 35 formed between the pair of magnetic poles 32A and 32B which have been excited in Step S14. The ion beam entering the beam passage 35 is ejected from the beam turning trajectory 78, along which the ion beam turns, due to action of the pair of excited magnetic poles 32A and 32B. That is, the ion beam is separated from the beam turning trajectory 78. Thereafter, the ion beam is separated from the beam turning trajectory 78, and moves toward the inlet of the beam extraction path 20. Due to action of the septum magnet 19, the ion beam is extracted from the accelerator 4 to the beam path 48 through the beam extraction path 20. The ion beam reaches the irradiation apparatus 7, and a target irradiation point inside the set layer is irradiated with the ion beam due to action of the scanning magnets 51 and 52.

The point of the ion beam, with which the target irradiation point is irradiated, is measured by the beam monitor 53, and based on the measured point, it is confirmed whether the target irradiation point is irradiated with the ion beam.

It is determined whether an irradiation dose applied to the irradiation point coincides with a target dose (Step S17). An irradiation does applied to the target irradiation point is measured by the dose monitor 54. The measured irradiation does is input to the dose determination apparatus 91. The dose determination apparatus 91 determines whether the irradiation dose, with which the target irradiation point has been irradiated and which has been measured, reaches the target irradiation dose. When the measured irradiation dose does not coincide with the target irradiation dose, the determination of Step S17 becomes "No". Each of Steps 16 and 17 is repeatedly executed, and until the measured irradiation dose coincides with the target irradiation dose, the target irradiation point is continuously irradiated with an ion beam. When the measured irradiation dose coincides with the target irradiation dose (When the determination of Step S17 is "Yes"), the dose determination apparatus 91 outputs a beam extraction stop signal to the injection electrode control apparatus 83.

The application of a voltage to the injection electrode is stopped (Step S18). When the injection electrode control apparatus 83 receives a beam extraction stop signal from the dose determination apparatus 91, the injection electrode control apparatus 83 controls the power supply 80 such that the power supply 80 stops applying a voltage to the injection electrode 18. As a result, injection of protons into the beam turning region 76 from the ion source 3 is stopped, and extraction of an ion beam to the beam path 48 from the accelerator 4 is stopped. That is, the irradiation of the target volume with an ion beam is stopped.

It is determined whether irradiation of the inside of the set layer with an ion beam is ended (Step S19). When irradiation of an irradiation point with an ion beam is ended, the layer determination apparatus 92 determines that the irradiation of the irradiation point inside the set layer with the ion beam is ended. When the determination result is "No", that is, when the irradiation of the irradiation point inside the set layer with the ion beam is not ended, each of Steps S15 to S19 is repeatedly executed. In repeated Step S15, an excitation current supplied to each of the scanning magnets 51 and 52 is controlled such that another target irradiation point inside the set layer is irradiated with an ion beam.

When the other irradiation point is irradiated with an ion beam in Step S16, and the determination of Step S17 becomes "Yes", application of a voltage to the injection electrode 18 is stopped in Step S17.

When the determination of Step S19 becomes "Yes", it is determined whether irradiation of all of the layers with ion beams is ended (Step S20). The layer determination apparatus 92 determines whether irradiation of all of the layers with ion beams is ended. Since there remains a layer which has not been irradiated with an ion beam, the determination of Step S20 becomes "No", and Steps S12 to S14, S7, and S15 to S20 are repeatedly executed in the listed sequence. In Step S12, a layer at a second distal position is set. An energy required by an ion beam, with which the layer is irradiated, is 219 MeV.

In repeated Step S13, similar to Step S13, the injection electrode 18 side corner of each of the one pair of magnetic poles 32A and 32B, which have been aligned with the beam turning trajectory 78 along which the ion beam of 220 MeV moves, is positioned on the beam turning trajectory 78 of an ion beam of 219 MeV. The amount of movement of the massless septum 12 in this case becomes greater than that when the magnetic poles 32A and 32B are positioned on the beam turning trajectory 78 along which the ion beam of 220 MeV moves. The one pair of magnetic poles 32A and 32B are excited in Step S14.

In Steps S15 and S16, when a voltage is applied to the injection electrode 18, the ion beam turns along the beam turning trajectory 78, and due to action of the one pair of excited magnetic poles 32A and 32B, the ion beam of 219 MeV is ejected from the beam turning trajectory 78 along which the ion beam of 219 MeV turns. The irradiation apparatus 7 irradiates an irradiation point inside a second distal layer of the target volume with the ejected ion beam. When the determination of Step S17 becomes "Yes", Step S18 is executed, and the irradiation of the irradiation point with the ion beam is stopped.

When the determination of Step S19 becomes "No", each of Steps S15 to S19 is repeated until the determination of Step S19 becomes "Yes". When the determination of Step S19 becomes "No", Steps S12 to S14, S7, and S15 to S20 are repeatedly executed in the listed sequence until the determination of Step S20 becomes "Yes". When each of Steps S12 to S14, S7, and S15 to S20 is repeated, in Step S12, a more proximal layer is set, and the energy of an ion beam reaching the layer is gradually decreased (for example, energy is decreased in a scale of 1 MeV from 220 MeV). In Steps S13 and S14, a pair of facing magnetic poles 32A and 32B of the massless septum 12 are positioned on the beam turning trajectory 78 along which an ion beam of a low energy turns, and thereafter, the magnetic poles are excited. When an ion beam of 180 MeV and an ion beam of 160 MeV are extracted from the accelerator 4, in Step S14, another pair of magnetic poles 32A and 32B, which are positioned adjacent to an injection electrode 18 side of a pair of magnetic poles 32A and 32B that are excited when an ion beam of 220 MeV and an ion beam of 200 MeV are extracted, is excited. In a case where the ion beam of 160 MeV is extracted, the amount of movement of the massless septum 12 when the magnetic poles are positioned in Step 13 becomes greater than that in a case where the ion beam of 180 MeV is extracted.

When the determination of Step S20 becomes "Yes", irradiation of the target volume with ion beams is ended (Step S21).

The ion beam irradiation treatment of the target volume of the patient 56 is ended.

In the embodiment, the iron cores 14A and 14B have a circular shape suitable for forming an outermost circumferential beam turning trajectory on the median plane 77, however, may have another shape. The annular coils 11A and 11B also have a circular shape, however, may have another shape, for example, a clover shape in which the annular coils 11A and 11B surround the magnetic poles formed on the base portions of the return yokes.

In a typical cyclotron, ion beams can be extracted only from a beam turning trajectory of an ion beam of the highest energy, which is formed at the outermost circumference. In contrast, in the embodiment, it is possible to densely form the multiple beam trajectories 78 of different energies in the vicinity of the septum magnet 19 and the inlet of the beam extraction path 20 by forming the eccentric beam trajectory region in an outer circumferential portion of the accelerator in which gaps between the beam trajectories are narrow. Therefore, at any time, it is possible to selectively extract ion beams of different energies not only from the beam trajectory 78 which is positioned at the outermost circumference and along which an ion beam of the highest energy turns, but also from multiple beam turning trajectories 78 formed inside the beam turning trajectory 76. For this reason, in the embodiment, ion beams of different energies can be efficiently extracted from the accelerator 4.

In the embodiment, in the eccentric trajectory region, the multiple annular beam turning trajectories 78 having the respective eccentric centers are densely formed between the injection electrode 18, the ion inlet port, or the ion injection portion 109 and the inlet of the beam extraction path 20 and the gaps between the annular beam turning trajectories 78 are wide in the direction that is 180° opposite to the inlet of the beam extraction path 20 relative to the injection electrode 18. The eccentric trajectory region is present at the periphery of the injection electrode 18 (or the ion inlet port or the ion injection portion 109) in the beam turning region 76, and is formed on the median plane 77 on which the beam turning trajectories 78 are formed. Therefore, in the eccentric beam turning trajectory region, the gaps between the beam turning trajectories 78 of ion beams of different energies are wide in the direction that is 180° opposite to the inlet of the beam extraction path 20 relative to the injection electrode 18. It is possible to efficiently separate ion beams of different energies from the respective beam turning trajectories 78. For this reason, it is possible to efficiently extract ion beams of different energies to the beam path 48 of the beam transport 13 through the beam extraction path 20 formed in the septum magnet 19 of the accelerator 4. In the embodiment, it is possible to continuously extract ion beams of different energies from the accelerator 4.

In the embodiment, the concentric trajectory region, in which the multiple annular beam turning trajectories 78 are formed concentric around the injection electrode 18, is formed inside the eccentric trajectory region on the median plane 77. Therefore, the degree of concentration of the beam turning trajectories 78 is reduced in the vicinity of the inlet of the beam extraction path 20 through which ion beams are extracted. As a result, a magnetic field gradient in the vicinity of the inlet is further decreased. Ion beams of different energies are capable of more stably turning along the respective beam turning trajectories 78.

Since the ion injection portion 109 (or the injection electrode 18 or the ion inlet port) is disposed at the position that is different from that of the center of gravity of the annular coils in the radial direction, the gaps between the multiple adjacent annular beam turning trajectories 78 (formed at the periphery of the ion injection portion (or the injection electrode 18 or the ion inlet port)) are wide in the region positioned opposite to the inlet of the beam extraction path 20 with reference to the ion injection portion (or the injection electrode 18 or the ion inlet port) compared to that in a region closer to the inlet of the beam extraction path 20 than the ion injection portion 109 (or the injection electrode 18 or the ion inlet port). For this reason, in the region in which gaps between adjacent beam turning trajectories 78 are wide and which is positioned opposite to the inlet of the beam extraction path 20, it is possible to easily separate ion beams from the respective beam turning trajectories 78, and it is possible to efficiently extract ion beams of different energies turning along the respective annular beam turning trajectories 78.

Since the ion injection portion 109 (or the injection electrode 18 or the ion inlet port) is disposed at the position that is different from that of the center of the iron cores in the radial direction, the gaps between the multiple adjacent annular beam turning trajectories 78 (formed at the periphery of the ion injection portion 109 (or the injection electrode 18 or the ion inlet port)) are wide in the region positioned opposite to the inlet of the beam extraction path 20 with reference to the ion injection portion 109 (or the injection electrode 18 or the ion inlet port) compared to that in the region closer to the inlet of the beam extraction path than the ion injection portion 109 (or the injection electrode 18 or the ion inlet port). For this reason, in the region in which gaps between adjacent beam turning trajectories 78 are wide and which is positioned opposite to the inlet of the beam extraction path 20, it is possible to easily separate ion beams from the respective beam turning trajectories 78, and it is possible to efficiently extract ion beams of different energies turning along the respective annular beam turning trajectories 78.

Since tip end portions of portions (extending toward the inside of the annular coil from the positions of inner surfaces of the radiofrequency acceleration electrodes 9C and 9D) of the radiofrequency acceleration electrodes 9C and 9D are respectively disposed at positions which are different from that of the center of gravity of the annular coil in the radial direction, the gaps between the multiple adjacent annular beam turning trajectories 78 (formed at the periphery of the positions at which the tip end portions of the radiofrequency acceleration electrodes 9C and 9D are respectively disposed) are wide in the region positioned opposite to the inlet of the beam extraction path 20 with reference to the ion injection portion 109 (or the injection electrode 18 or the ion inlet port) compared to that in the region closer to the inlet of the beam extraction path 20 than the ion injection portion 109 (or the injection electrode 18 or the ion inlet port). For this reason, in the region in which gaps between adjacent beam turning trajectories 78 are wide and which is positioned opposite to the inlet of the beam extraction path 20, it is possible to easily separate ion beams from the respective beam turning trajectories 78, and it is possible to efficiently extract ion beams of different energies turning along the respective annular beam turning trajectories 78.

Since the magnetic poles (protrusions) 7A to 7F are installed in such a way as to extend radially inward from the outer circumference of the iron core toward the position that is different from that of the center of gravity of the iron core in the radial direction, the gaps between the multiple adjacent annular beam turning trajectories 78 (formed at the periphery of the position at which respective tip end portions of the magnetic poles 7A to 7F are disposed and which is different from that of the center of gravity of the iron core in the radial direction) are wide in the region positioned opposite to the inlet of the beam extraction path 20 with reference to the ion injection portion 109 (or the injection electrode 18 or the ion inlet port) compared to that in the region closer to the inlet of the beam extraction path 20 than the ion injection portion 109 (or the injection electrode 18 or the ion inlet port). For this reason, in the region in which gaps between adjacent beam turning trajectories 78 are wide and which is positioned opposite to the inlet of the beam extraction path 2, it is possible to easily separate ion beams from the respective beam turning trajectories 78, and it is possible to efficiently extract ion beams of different energies turning along the respective annular beam turning trajectories 78.

In the embodiment, the multiple beam turning trajectories 78 are densely formed in the vicinity of the inlet of the beam extraction path 20, and thus, ion beams of different energies separated from the respective beam turning trajectories 78 can be easily injected into the inlet of the beam extraction path 20, and it is possible to efficiently extract ion beams of different energies.

In the embodiment, the position of the center of the annular beam turning trajectories 78 formed by the magnetic poles 7A to 7F is different from that of the center of gravity of the annular coils, and thus, the gaps between the multiple adjacent annular beam turning trajectories 78, which are formed at the periphery of the ion injection portion 109 (or the injection electrode 18 or the ion inlet port), are wide in a region close to the center of the annular beam turning trajectories 78 compared to that in the region close to the inlet of the beam extraction path 20. For this reason, in the region in which gaps between adjacent beam turning trajectories 78 are wide and which is positioned close to the center of the beam turning trajectories 78, it is possible to easily separate ion beams from the respective beam turning trajectories 78, and it is possible to efficiently extract ion beams of different energies turning along the respective annular beam turning trajectories 78.

In the embodiment, a region having the highest magnetic field strength on the median plane 77 is formed closer to the ion injection portion 109 (or the injection electrode 18 or the ion inlet port) than an outermost circumferential beam turning trajectory 78 in a first magnetic field region, and thus, it is possible to efficiently extract ion beams of different energies, and to improve stability of an ion beam turning along a beam turning trajectory that is positioned in the outer circumferential portion among the multiple annular beam turning trajectories 78 formed on the median plane 77.

In the embodiment, in the pair of iron cores 14A and 14B, the magnetic poles 7A to 7F are formed at the periphery of the ion injection portion 109 (or the injection electrode 18 or the ion inlet port) such that the magnetic poles 7A to 7F extend radially from the ion injection portion 109 (or the injection electrode 18 or the ion inlet port) and the respective tip ends of the magnetic poles 7A to 7F face the ion injection portion 109 (or the injection electrode 18 or the ion inlet port), the recesses 29A to 29F are formed at the periphery of the ion injection portion 109 (or the injection electrode 18 or the ion inlet port) in such a way as to extend radially from the ion injection portion 109 (or the injection electrode 18 or the ion inlet port), the magnetic poles and the recesses are alternately disposed at the periphery of the ion injection portion 109 (or the injection electrode 18 or the ion inlet port), and the annular coils 11A and 11B surround the respective magnetic poles 7A to 7F and the respective recesses 29A to 29F which are respectively disposed inside the iron cores 14A and 14B. As a result, it is possible to stably inject ions into the beam turning region 76 via the ion injection tube 3A.

In the embodiment, the inlet of the beam extraction path 20 opens in the recesses (the second recess) 29D, and thus, ion beams separated from the respective annular beam turning trajectories 78 can be easily injected into the inlet of the beam extraction path 20, and it is possible to efficiently extract ion beams of different energies turning along the respective annular beam turning trajectories 78. The reason for this is that the annular beam turning trajectories 78 formed in the eccentric trajectory region are densely formed in the recess 29A on the inlet side of the beam extraction path 20.

In the embodiment, each of the magnetic poles 7A to 7F has the bent points, and the portion of each of the magnetic poles 7A to 7F between the bent points and the end surface thereof facing the inner surface of the annular coil is bent toward the recess 29A. As a result, an eccentric beam region, in which there are the multiple eccentric beam turning trajectories 78, is formed, gaps between beam turning trajectories are wide, and it is possible to efficiently extract ion beams of different energies turning along the respective annular beam turning trajectories 78.

In the embodiment, beam current measuring apparatus 98 is disposed in the recess 29A, and thus, it is possible to obtain energy information items regarding ion beams turning along the respective beam turning trajectories 78 and position information items regarding the positions of the beam turning trajectories 78 in the radial direction of the annular coils by performing measurement via the beam current measuring apparatus 98. It is possible to obtain position information regarding the beam turning trajectory 78 corresponding to the energy of an ion beam with which a set layer contained a target volume is irradiated, based on the energy information items regarding the ion beams and the position information items regarding the beam turning trajectories 78. It is possible to specify a pair of facing magnetic poles 32A and 32B to be excited of the massless septum based on the position information. It is possible to accurately position the pair of facing magnetic poles 32A and 32 to be excited on the beam turning trajectory 78 along which the ion beam of an energy (with which the set layer is irradiated) turns.

Since the beam current measuring unit 15 of the beam current measuring apparatus 98 can be moved inside the recess 29A toward the ion injection portion 109 (or the injection electrode 18 or the ion inlet port) along the median plane 77 by the movement apparatus 17A, it is possible to obtain a wide range of energy information regarding ion beams for the respective beam turning trajectories 78 and a wide range position information regarding the beam turning trajectories 78.

When the position of the beam turning trajectory 78, which is measured by the beam current measuring apparatus 98 disposed in the recess 29A, does not coincide with a predetermined position, an excitation current, which is supplied to the trim coils 8A to 8F attached to the respective magnetic poles 7A to 7F, is adjusted by the coil current control apparatus 94. As a result, even if the beam turning trajectory 78, which is not present at the predetermined position, is formed, it is possible to form the beam turning trajectory 78 at the predetermined position.

In the embodiment, as described above, in each of the pair of iron cores 14A and 14B, in regions which are positioned on a plane perpendicular to the central axis C and on both sides of the alternate long and short dash line X, the radiofrequency acceleration electrode 9C with the tip end facing the injection electrode 18 is disposed between the magnetic poles 7C and 7E adjacent to each other in the circumferential direction of the vacuum chamber 27, the radiofrequency acceleration electrode 9D with the tip end facing the injection electrode 18 is disposed between the magnet 7D and the magnetic pole 7F adjacent to each other in the circumferential direction of the vacuum chamber 27, the portion of the radiofrequency acceleration electrode 9C between the bent points 24M and 24N and the end surface of the radiofrequency acceleration electrodes 9C facing the annular coil 11A or 11B is bent toward the recess 29A, the portion of the radiofrequency acceleration electrode 9C between the bent points 24M and 24N and the end surface of the radiofrequency acceleration electrode 9C facing either the annular coil 11A or the annular coil 11B is bent toward the recess 29A. As a result, it is possible to easily accelerate ion beams turning along the respective beam turning trajectories 78 which are present between the beam turning trajectory 78 close to the injection electrode 18 and the beam turning trajectory 78 close to the annular coil 11A or 11B. In the embodiment, the radiofrequency acceleration electrodes 9A and 9B are respectively disposed between the magnetic poles 7A and 7C and between the magnetic poles 7B and 7D, and are respectively disposed between the bent points of the respective magnetic poles and the end surfaces thereof facing either the annular coil 11A or the annular coil 11B. As a result, it is possible to easily accelerate ion beams turning along the respective beam turning trajectories 78 of ion beams of high energies.

In the embodiment, the beam current measuring unit 15 is disposed in the recess 29A and on the median plane 77, and is moved on the median plane 77 along the alternate long and short dash line X by the movement apparatus 17, and the position of the moving beam current measuring unit 15 on the median plane 77 is detected by the position detector 39. As a result, as described above, it is possible to accurately detect a beam current value of each of the beam turning trajectories 78 and the position of each of the beam turning trajectories 78.

Since the massless septum 12 is disposed in the respective recesses 29A of the pair of iron cores 14A and 14B, it is possible to easily dispose the massless septum 12 between the iron cores 14A and 14B.

Since the massless septum 12 is disposed in the recesses 29A, the massless septum 12 is positioned in a portion of the eccentric beam turning trajectory region in which gaps between the beam turning trajectories 78 are wide, and it is possible to efficiently separate ion beams of different energies from the respective beam turning trajectories 78 via the massless septum 12. As a result, it is possible to efficiently extract ion beams of different energies from the accelerator 4.

Since the massless septum 12 includes the multiple pairs of facing magnetic poles 32A and 32B, it is possible to position the massless septum 12 on the beam turning trajectory 78 based on the energy of an ion beam with which a set layer of a target volume is irradiated, and to easily specify a pair of the magnetic poles 32A and 32B to be excited.

Since the movement apparatus 17 is provided to move the massless septum 12 in the radial direction of the annular coils, it is possible to perform adjustment of the positioning of a pair of the magnetic poles 32A and 32B to be excited of the massless septum 12 on the beam turning trajectory 78 along which an ion beam of energy (with which a set layer of a target volume is to be irradiated) turns. For this reason, it is possible to accurately position a pair of the magnetic poles 32A and 32B on the corresponding beam turning trajectory 78.

In a particle beam irradiation system using a cyclotron, a degrader including multiple metal plates of different thicknesses is provided in a beam transport to change the energy of an ion beam with which a target volume is irradiated. In contrast, as described above, in the particle beam irradiation system 1 of the embodiment, ion beams of different energies can be extracted from the accelerator 4, and a degrader is not required. Alternatively, it is possible to considerably reduce the use of the deflector. For this reason, in the particle beam irradiation system 1, it is possible to prevent an increase in the beam size of an ion beam caused by the degrader, a reduction in the number of ions caused by scattering of a portion of ions when the ions penetrate through metal plates of the degrader, and an increase in radioactive waste caused by radioactivation of the degrader.

In the embodiment, in order to maintain a vacuum state of the beam turning region 76 in which ion beams turn, the vacuum chamber 27 is formed such that the pair of iron cores 14A and 14B are disposed to face each other and are joined together. For this reason, it is possible to further reduce the size of the accelerator 4 in the embodiment compared to that of an accelerator in which a vacuum chamber is disposed between facing iron cores 14 and 14B in Embodiments 8 and 9 which will be described later.

In the embodiment, as described above, on the beam turning trajectory 78 along which an ion beam of a low energy (ion beam of 70 MeV or less) turns, an ion beam is accelerated by two radiofrequency acceleration electrodes 9C and 9D. Since the beam turning trajectories 78 are eccentric with each other, on the beam turning trajectory 78 along which an ion beam of a high energy (ion beam of an energy exceeding 70 MeV) which requires stable and fine trajectory control and requires a high radiofrequency acceleration voltage or a long acceleration time for a higher acceleration due to a high energy, an ion beam is accelerated by four radiofrequency acceleration electrodes 9A to 9D.

Even if one or three or more radiofrequency acceleration electrodes, which are disposed between the bent points of the magnetic poles and the inner surface of the annular coil and extend from the ion inlet port to the inner surface of the annular coil, may be provided, the aforementioned functions can be demonstrated. In order to form the eccentric trajectory region is formed on the median plane 77 which is a trajectory plane in the beam turning region 76, among the radiofrequency acceleration electrodes 9A to 9D, the radiofrequency acceleration electrodes 9A and 9C are respectively symmetrical in shape and disposition with the radiofrequency acceleration electrodes 9B and 9D relative to a straight line (the alternate long and short dash line X) that connects the central axis C to the inlet of the beam extraction path 20. As a result, it is possible to easily obtain stability of turning ion beams.

The iron cores 14A and 14B have a circular shape in the horizontal direction, and typically, the center of the iron cores 14A and 14B represents the structural center of the accelerator 4. The annular coils 11A and 11B are circular main coils, and typically, similarly, the center and the center of gravity of the annular coils 11A and 11B represent the structural center of the accelerator 4. In the accelerator 4 of the embodiment, the ion injection portion is installed at a different position from that of the center of the iron cores and the center of gravity of the annular coils. The ion injection portion is provided at a position offset toward the inlet of the beam extraction path 20.

In a typical cyclotron, beam turning trajectories are concentrically formed around the structural center of an accelerator, and thus, ions are injected to the structural center of the accelerator. Strictly speaking, ions are not injected to the central point, but are injected into an innermost beam turning trajectory. In a case where ions are injected and guided to the innermost beam turning trajectory, and a region inside of the innermost beam turning trajectory is defined as an ion injection portion, in a typical cyclotron, the ion injection portion is positioned at the structural center of the accelerator. In contrast, in the accelerator 4 of the embodiment, the ion injection portion is installed at a different position from that of the center of the iron cores and the center of gravity of the annular coils. The ion injection portion is disposed at a position offset toward the inlet of the beam extraction path 20.

Embodiment 2

Hereinafter, a particle beam irradiation system in Embodiment 2, which is another preferred embodiment of the present invention, will be described with reference to FIG. 27.

A particle beam irradiation system 1A in the embodiment includes an accelerator 4A, and has a configuration obtained by replacing the accelerator 4 in the particle beam irradiation system 1 of Embodiment 1 with the accelerator 4A. The rest of the configuration of the particle beam irradiation system 1A is the same as that of the particle beam irradiation system 1.

The accelerator 4A includes the vacuum chamber 27 including the return yokes 5A and 5B. The return yokes 5A and 5B are substantially the same as the return yokes 5A and 5B in Embodiment 1. The return yoke 5B of the accelerator 4A will be described. The return yoke 5B includes six magnetic poles 7A to 7F and four radiofrequency acceleration electrodes 9A to 9D, and six recesses 29A to 29F are formed in the return yoke 5B. The magnetic poles 7A to 7F and the radiofrequency acceleration electrodes 9A to 9D are disposed inside the annular coil 11B. Similar to the accelerator 4, the recesses 29A to 29F are respectively disposed between the magnetic poles 7A to 7F. The radiofrequency acceleration electrodes 9A to 9D of the accelerator 4A are disposed in the same manner in which the radiofrequency acceleration electrodes 9A to 9D are disposed in the accelerator 4.

An ion inlet port and the injection electrode 18 are disposed in the accelerator 4A in a state where the ion inlet port and the injection electrode 18 are moved closer to the inlet of the beam extraction path 20 than in the return yoke 5B of the accelerator 4. The ion injection tube 3A is installed in the return yoke 5A in a state where the ion injection tube 3A is also moved to the position of the injection electrode 18 by the extent of the movement of the injection electrode 18 to the inlet of the beam extraction path 20. The suction tube 26 formed in the return yoke 5B of the accelerator 4A is attached to the return yoke 5B of the accelerator 4A on an extension line of the ion injection tube 3A.

The respective bent points 24A to 24P of the magnetic poles 7A to 7F and the radiofrequency acceleration electrodes 9C and 9D are disposed further inward than in the accelerator 4, and are disposed on the beam turning trajectory 78 which is formed at the periphery of the injection electrode 18 and along which an ion beam of 10 MeV turns. The respective tip ends of the magnetic poles 7A to 7F and the radiofrequency acceleration electrodes 9C and 9D are sharp and face the injection electrode 18. Similar to the shapes illustrated in FIG. 3, the magnetic poles 7A to 7F and the radiofrequency acceleration electrodes 9C to 9D are tapered toward the respective tip ends from the respective bent points. Portions of the magnetic poles 7A to 7F and the radiofrequency acceleration electrodes 9C and 9D between the respective bent points and the respective end surface thereof facing the inner surface of the annular coil 11B respectively have lengths greater than those in the return yoke 5B of the accelerator 4 in Embodiment 1. The radiofrequency acceleration electrodes 9A and 9B, which are disposed closer to the inner surface of the annular coil 11B than the respective bent points of the magnetic poles 7A to 7D, respectively have lengths little longer than those of the radiofrequency acceleration electrodes 9A and 9B of the accelerator 4.

For this reason, a concentric trajectory region formed around the injection electrode 18 inside the return yoke 5B of the accelerator 4A is smaller than that region in the accelerator 4. In contrast, an eccentric trajectory region formed at the periphery of the concentric trajectory region becomes larger than that region in the accelerator 4.

The return yoke 5A of the accelerator 4A also includes the magnetic poles 7A to 7F and the radiofrequency acceleration electrodes 9A to 9D having the same shapes as those in the return yoke 5B of the accelerator 4A. The accelerator 4A has the same configuration as that of the accelerator 4 including the massless septum 12 except for the respective shapes of the magnetic poles 7A to 7F and the radiofrequency acceleration electrodes 9A to 9D and the positions at which the injection electrode 18, the ion injection tube 3A, and the suction tube 26 are respectively disposed.

The particle beam irradiation system 1A in the embodiment also irradiates a target volume of the patient 56 on the treatment bed 55 with ion beams by executing each of Steps S1 to S6, S23, S24, S7 to S14, S7, and S15 to S21 executed by the particle beam irradiation system 1.

In the embodiment, it is possible to obtain the same effects as in Embodiment 1.

Embodiment 3

Hereinafter, a particle beam irradiation system in Embodiment 3, which is still another preferred embodiment of the present invention, will be described with reference to FIG. 28.

A beam transport and a rotating apparatus of the accelerator 4 of a particle beam irradiation system 1B in the embodiment are different from those of the particle beam irradiation system 1 in Embodiment 1. The accelerator 4, the irradiation apparatus 7, and the control system 65 of the particle beam irradiation system 1B are the same as those of the particle beam irradiation system 1.

In Embodiments 1 and 2, the accelerators 4 and 4A are horizontally disposed, and the lower surface of the return yoke 5B of the vacuum chamber 27 is installed such that the lower surface of the return yoke 5B is placed on a floor of a building. The particle beam irradiation system 1B in the embodiment includes a rotating frame that is rotatably installed on the floor. The accelerator 4 disposed vertically is attached to the rotating frame. The rotating frame has the same configuration as that of a rotating frame disclosed in PTL 5, and is supported by rotating rollers that are provided in a support apparatus installed on the floor of the building. The support apparatus is the same as a support apparatus (refer to PTL 6) including multiple rollers which supports a rotating gantry provided in a particle beam irradiation system including a synchrotron in the related art. At least one of the rollers provided in the support apparatus is rotated by the rotating apparatus (for example, a motor). The rotating frame is rotated via rotation of the rollers, and the accelerator 4 is rotated around the central axis C of the vacuum chamber 27. Since the accelerator 4 is vertically disposed, the median plane 77 formed inside the vacuum chamber 27 is perpendicular to the floor.

A treatment room is surrounded by a radiation shielding wall (not illustrated), and the radiation shielding wall has the same structure as that of a radiation enclosure disclosed in PTL 5. A portion of the radiation shielding wall is a side wall, and is disposed between the accelerator 4 attached to the rotating frame and the treatment room. The treatment bed 55, on which the patient 56 to be treated lies, is installed inside the treatment room.

The beam path 48 of a beam transport 13B, that is connected to the beam extraction path 20 formed inside the septum magnet 19 provided in the vacuum chamber 27, extends on the outside of the vacuum chamber 27 in the radial direction of the vacuum chamber 27, is bent in the horizontal direction, and extends to a position directly above the treatment room along the radiation shielding wall which is a ceiling portion of the treatment room. The beam path 48 is bent toward the treatment room from the position directly above the treatment room. Bending magnets 95 and 96 are respectively disposed in bent portions of the beam path 48, and multiple quadrupole magnets 97 are provided on the beam path 48. The irradiation apparatus 7 is attached to a tip end portion of the beam path 48. Similar to the particle beam irradiation system 1 in Embodiment 1, two scanning magnets 51 and 52, the beam point monitor 53, and the dose monitor 54 are attached to the irradiation apparatus 7.

When a target volume is treated by irradiating a tumor volume of the patient 56, who lies on the treatment bed 55 inside the treatment room, with ion beams, the proton beam therapy system 1B executes each of Steps S1 to S6, S23, S24, S7 to S14, S7, and S15 to S21 executed in Embodiment 1. Particularly, in a case where the proton beam therapy system 1B is used, the rotating frame is rotated such that the accelerator 4 is rotated in Step S11. At this time, the beam transport 13B and the irradiation apparatus 7 are turned around the center of rotation (the central axis C) of the accelerator 4. The beam axis of the irradiation apparatus 7 becomes aligned with an irradiation direction of ion beams to the target volume via turning of the irradiation apparatus 7. In this case, the target volume of the patient 56 on the treatment bed 55 is positioned on an extension line of the center of rotation of the accelerator 4.

The target volume is irradiated with ion beams and is treated by executing each of Steps S11 to S14, S7, and S15 to S21.

In the embodiment, it is possible to obtain the same effects as in Embodiment 1. In the embodiment, the accelerator 4 is vertically disposed, and is rotated by the rotating frame, and thus, the size of the particle beam irradiation system 1B becomes smaller than that of the particle beam irradiation system 1 in Embodiment 1.

Embodiment 4

Hereinafter, a particle beam irradiation system in Embodiment 4, which is still another preferred embodiment of the present invention, will be described with reference to FIGS. 29 and 30.

A particle beam irradiation system 1C in the embodiment has a configuration obtained by replacing the ion beam generator 2 in the particle beam irradiation system 1 with an ion beam generator 2A. The ion beam generator 2A has a configuration obtained by replacing the accelerator 4 in the ion beam generator 2 with an accelerator 4B. The accelerator 4B has a configuration obtained by omitting the massless septum 12, the movement apparatus 17, and the power supply 40 from the accelerator 4 and adding the energy absorber 62 and a movement apparatus 60 to the accelerator 4. A control system 65A of the particle beam irradiation system 1C has a configuration obtained by replacing the accelerator and transport control apparatus 69 in the control system 65 with an accelerator and transport control apparatus 69A. The accelerator and transport control apparatus 69A has a configuration obtained by replacing the massless septum control apparatus 86 in the accelerator and transport control apparatus 69 with an energy absorber control apparatus (a second control apparatus) 93. The energy absorber control apparatus 93 is connected to the CPU 67, the memory 107, and the irradiation point control apparatus 89. The rest of the configuration of the accelerator and transport control apparatus 69A is the same as that of the accelerator and transport control apparatus 69. The rest of the configuration of the particle beam irradiation system 1C is the same as that of the particle beam irradiation system 1. The beam current measuring apparatus 98, which is used in the particle beam irradiation system 1 and includes the beam current measuring unit 15, the operation member 16A, the movement apparatus 17, and the position detector 39, is also used in the particle beam irradiation system 1C, which is not illustrated in FIGS. 29 and 30. Similar to the particle beam irradiation system 1, the beam current measuring apparatus 98 is attached to the vacuum chamber 27. The beam current measuring unit 15 and the operation member 16A are disposed in the recess 29A and on the median plane 77.

The energy absorber 62 is disposed inside the vacuum chamber 27 and between the magnetic pole 7A of the return yoke 5A and the magnetic pole 7A of the return yoke 5B which faces the magnet 7A of the return yoke 5A. The energy absorber 62 is attached to a tip end portion of a bar-shaped operation member 63. The energy absorber 62 is a thin aluminum plate, and is disposed to be perpendicular to the beam turning trajectories 78. The energy absorber 62 may be formed of non-magnetic metallic materials such as tungsten, copper, and titanium, or non-metallic materials. The width of the energy absorber 62 in the direction perpendicular to the median plane 77 is smaller than a gap between the magnetic pole 7A of the return yoke 5A and the magnetic pole 7A of the return yoke 5B.

The operation member 63 attached to the energy absorber 62 passes through the vacuum chamber 27, and extends to the outside of the vacuum chamber 27. The operation member 63 is a support member for the energy absorber 62, and is connected to a piston of the movement apparatus 60 including the piston and a cylinder on the outside of the vacuum chamber 27. The operation member 63 is disposed between the facing magnetic poles 29A and between the annular coils 11A and 11B. For example, the operation member 63 is slidably attached to the cylindrical portion 75B in a state where the operation member 63 has passed through the cylindrical portion 75B of the return yoke 5B. A position detector 61 is attached to the movement apparatus 60, and detects the position of the energy absorber 62 inside the vacuum chamber 27 (refer to FIG. 29). The movement apparatus 60 may be a motor. In a case where a motor is used as the movement apparatus 60, an encoder is used as the position detector 38, and is connected to a rotational shaft of the motor. The energy absorber 62, the operation member 63, the movement apparatus 60, and the position detector 61 form an extraction adjustment apparatus which is a type of beam separation apparatus.

Among Steps S1 to S6, S23, S24, and S7 to S10 illustrated in Embodiment 1, the particle beam irradiation system 1C also executes steps except for Steps S8 and S9. Step S22 (refer to FIG. 32) (to be described later) is executed between Steps S7 and S10, instead of Steps S8 and S9. Step S22 will be described in detail later.

In a case where a target volume of the patient 56 on the treatment bed 55 is treated by irradiating the target volume with ion beams, each of Steps S11, S12, S22, S7, and S15 to S21 illustrated in FIG. 32 is executed. Steps other than Step S22 are executed similar to Embodiment 1. Hereinafter, Step S22 will be described.

The energy absorber is positioned (Step S22). In order to execute Step S22, based on control command information from the CPU 67, the energy absorber control apparatus 93 controls the movement apparatus 60 such that the movement apparatus 60 moves the operation member 63. As a result, the energy absorber 62 is moved on the median plane 77 toward the central axis C of the vacuum chamber 27. Due to such a movement of the energy absorber 62, the energy absorber 62 is capable of crossing at least the beam turning trajectories 78 along which ion beams of 70 MeV to 250 MeV respectively turn.

The energy absorber control apparatus 93 specifies the position of the beam turning trajectory 78 of an ion beam of an energy slightly higher than the energy of an ion beam with which a layer set in Step S12 is to be irradiated, based on energy information regarding the ion beam with which the layer is irradiated, which is input from the irradiation point control apparatus 89, the degree of energy dampening performed by the energy absorber 62, and position information regarding the beam turning trajectories 78 which is measured by the position detector 39 and is stored in the memory 107 while being associated with energies. The energy absorber control apparatus 93 moves the energy absorber 62 to the position of the specified beam turning trajectory 78 and positions the energy absorber 62 on the beam turning trajectory 78 by controlling the specified movement apparatus 60.

The position of the energy absorber 62 in the radial direction of the median plane 77 (position inside the vacuum chamber 27 in the radial direction) is measured by the position detector 61. Position information regarding the energy absorber 62 measured by the position detector 61 is input to the energy absorber control apparatus 93. The energy absorber control apparatus 93 determines whether the measured position information regarding the energy absorber 62 coincides with the specified position of the beam turning trajectory 78. In a case where there is no coincidence therebetween, the energy absorber control apparatus 93 controls the movement apparatus 60 such that the energy absorber 62 is moved to the position of the beam turning trajectory. In a case where the measured position information regarding the energy absorber 62 coincides with the position of the beam turning trajectory, the energy absorber control apparatus 93 stops driving of the movement apparatus 60.

In a case where the energy absorber 62 is positioned at the specified position of the beam turning trajectory 78 through control of the movement apparatus 60 via the energy absorber control apparatus 93, after ions are injected into the beam turning region 76 in Step S16, an ion beam turning along the beam turning trajectory 78 at the specified position is dampened when passing through the energy absorber 62. As a result, the ion beam of a dampened energy is positioned outside of an equilibrium trajectory. The beam is subjected to betatron oscillation while moving to the recess 29D in which the beam extraction path 20 is positioned, and moves toward the inlet of the beam extraction path 20. As a result, the ion beam, which has passed through the energy absorber 62, is extracted to the beam path 48 of the beam transport 13 from the accelerator 4B through the beam extraction path 20.

In a case where the energy of an ion beam, with which a layer of the target volume is irradiated, is determined to be 200 MeV based on treatment planning data, an ion beam of 200 MeV is required to be extracted from the accelerator 4B into the beam path 48. The energy of an ion beam, which has passed through the energy absorber 62, is required to be 200 MeV. In this case, energy dampening by the energy absorber 62 is taken into consideration, and thus, an ion beam of an energy of 205 MeV is required to penetrate through the energy absorber 62. In this case, the energy absorber 62 is positioned on a beam turning trajectory along which an ion beam of 205 MeV turns.

When the determination of Step S20 is "No", each of Steps S11, S12, S22, S7, and S15 to S20 is repeatedly executed until the determination of Step S20 becomes "Yes". During repletion, the aforementioned positioning of the energy absorber 62 is performed in Step S22.

In the embodiment, among the effects obtained in Embodiment 1, it is possible to obtain the remaining effects except for an effect obtained by the massless septum 12. In the embodiment, the massless septum 12 with a complicated structure and the power supply 40 are not required, and thus, the structure of the particle beam irradiation system 1C can be simplified.

Since the movement apparatus 17A is provided to move the energy absorber 62 in the radial direction of the annular coils, it is possible to perform adjustment of the positioning of the energy absorber 62 on the beam turning trajectory 78 along which an ion beam of energy (with which a set layer of the target volume is to be irradiated) turns. For this reason, it is possible to accurately position the energy absorber 62 on the beam turning trajectory 78.

Embodiment 5

Hereinafter, a particle beam irradiation system in Embodiment 5, which is another preferred embodiment of the present invention, will be described with reference to FIGS. 33 and 34.

A particle beam irradiation system 1D in the embodiment has a configuration obtained by replacing the accelerator 4 in the particle beam irradiation system 1 with an accelerator 4C. The accelerator 4C has a configuration obtained by adding the energy absorber 62, the operation member 63, and the movement apparatus 60 to the configuration of the accelerator 4. The rest of the configuration of the particle beam irradiation system 1C is the same as that of the particle beam irradiation system 1. The accelerator and transport control apparatus 69 in the embodiment includes the energy absorber control apparatus 93 in addition to the massless septum control apparatus 86. Since the massless septum 12 is used, the thickness of the energy absorber 62 in the embodiment can be reduced to a thickness smaller than that of the energy absorber 62 in Embodiment 4.

The particle beam irradiation system 1D executes each of Steps S1 to S6, S23, S24, and S7 to S10 illustrated in Embodiment 1. In a case where a target volume of the patient 56 on the treatment bed 55 is treated by irradiating the target volume with ion beams via the particle beam irradiation system 1D, each of Steps S11, S12, S22, S13, S14, S7, and S15 to S21 illustrated in FIG. 35 is executed. Step S22 is the same step as that executed in Embodiment 4.

In the embodiment, extraction of ion beams in Step S16 is different from that in Embodiments 1 and 4 due to use of the massless septum 12 and the energy absorber 62, and thus, Step S16 will be described in detail.

The energy absorber 62 is disposed upstream of the massless septum 12 in a turning direction of ion beams. For this reason, after the energy of an ion beam is dampened by the energy absorber 62, the ion beam of a dampened energy is ejected by the massless septum 12. The ion beam of an energy dampened by the energy absorber 62 moves inward from a beam turning trajectory along which the ion beam turns before the energy of the ion beam is dampened. Since the amount of movement of the ion beam has been already known, when electrodes of the massless septum 12 are positioned in Step S13, as described above, with the amount of movement taken into consideration, the movement apparatus 17 positions a pair of the facing magnetic poles 32A and 32B (positioned inside of the beam turning trajectory along which the ion beam turns before the energy thereof is dampened) at the position of an ion beam which has penetrated the energy absorber 62.

For this reason, in Step S16, the energy absorber 62 is disposed on the beam turning trajectory along which the ion beam (formed by ions injected into the beam turning region 76) turns, and thus, the energy of the ion beam, which has passed through the energy absorber 62, is dampened and becomes equal to the energy of an ion beam with which a layer of the target volume is irradiated. The ion beam which has passed through the energy absorber 62 is ejected by the pair of excited magnetic poles 32A and 32B of the massless septum 12 which is positioned in advance. The ejected ion beam is injected into the beam extraction path 20, and is extracted to the beam path 48 of the beam transport 13.

In the embodiment, it is possible to obtain the same effects as in Embodiments 1 and 4. In the embodiment, the massless septum 12 is used with the energy absorber 62, the thickness of the energy absorber 62 can be reduced to a thickness smaller than that of the energy absorber 62 in Embodiment 4. For this reason, scattering of ion beams by the energy absorber 62 is decreased, and to that extent, ion beams extracted from the accelerator 4C into the beam transport 13 are increased. Ion beam utilization efficiency in treatment of the patient 56 is increased.

Embodiment 6

Hereinafter, a particle beam irradiation system in Embodiment 6, which is another preferred embodiment of the present invention, will be described with reference to FIGS. 36, 37, and 38.

A particle beam irradiation system 1E in the embodiment has a configuration obtained by replacing the beam current measuring apparatus 98 in the particle beam irradiation system 1 of Embodiment 1 with a beam current measuring apparatus 98A. The rest of the configuration of the particle beam irradiation system 1E is the same as that of the particle beam irradiation system 1.

As illustrated in FIGS. 40 and 41, the beam current measuring apparatus 98A includes a monitor housing 101; multiple monitor electrodes 103A; and multiple monitor electrodes 103B. The monitor housing 101 includes housing body portions 102A and 102B which face each other and are disposed parallel with each other, and a connection portion 102C. The monitor electrodes 103A are disposed in a row with a predetermined gap therebetween. Each of the monitor electrodes 103A is attached to one surface of the housing body portion 102A, which faces the housing body portion 102B, via multiple (for example, four) insulators 104. The monitor electrodes 103B are disposed in a row with a predetermined gap therebetween. Each of the monitor electrodes 103B is attached to one surface of the housing body portion 102B, which faces the housing body portion 102A, via multiple (for example, four) insulators 104. Respective end portions of the housing body portions 102A and 102B are joined together via the connection portion 102C. The monitor electrodes 103A are disposed to respectively face the monitor electrodes 103B.

An electrode lead wire 106 is connected to each of the monitor electrodes 103A, and another electrode lead wire 106 is also connected to each of the monitor electrodes 103B. The electrode lead wires 106 respectively connected to the monitor electrodes 103A are bundled together and are covered with an electrode lead cover 105A so as to prevent damage to the electrode lead wires 106 caused by degassing and electrical discharge in a vacuum state of the vacuum chamber 27. The electrode lead cover 105A is attached to a top surface of the housing body portion 102A along the top surface. The electrode lead wires 106 respectively connected to the monitor electrodes 103B are also bundled together and are covered with an electrode lead cover 105B so as to prevent damage to the electrode lead wires 106 caused by degassing and electrical discharge in a vacuum state of the vacuum chamber 27. The electrode lead cover 105B is attached to a top surface of the housing body portion 102B along the top surface. The electrode lead wires 106 respectively connected to the monitor electrodes 103A and the electrode lead wires 106 respectively connected to the monitor electrodes 103B are bundled together at the position of the connection portion 102C, and pass through the cylindrical portion 75B of the return yoke 5B and are extracted to the outside of the vacuum chamber 27 while being covered with an electrode lead cover (not illustrated). The electrode lead wires 106 are connected to the beam current measuring unit control apparatus 84.

As illustrated in FIGS. 38 and 39, the beam current measuring apparatus 98A is disposed between the magnetic poles 32A and the magnetic poles 32B facing the magnetic poles 32A of the massless septum 12, and is attached to the massless septum 12. In the embodiment, the massless septum 12 is also disposed in the recesses 29A which are respectively formed in the facing return yokes 5A and 5B. For this reason, the beam current measuring apparatus 98A is also disposed in the recesses 29A. The beam passage 35 is formed between the monitor electrodes 103A and the monitor electrodes 103B, and is a gap through which turning ion beams pass. The beam passage 35 contains a portion of the median plane 77. The monitor electrodes 103A and 103B face each other with the median plane 77 interposed therebetween. The monitor housing 101 has a length larger than that of the massless septum 12. The multiple monitor electrodes 103A and the multiple monitor electrodes 103B are provided in the monitor housing 101 so as to be capable of measuring beam currents in a range from the beam turning trajectory 78 of an ion beam of 35 MeV to the beam turning trajectory 78 of an ion beam of 250 MeV.

The particle beam irradiation system 1E in the embodiment irradiates a target volume of the patient 56 on the treatment bed 55 with ion beams by executing each of Steps S1 to S6, S23, S24, S7 to S14, S7, and S15 to S21 executed by the particle beam irradiation system 1. Among these steps, Step S6 (measurement of ion beams) executed in the embodiment will be described in detail. In the embodiment, Step S6 is executed by the beam current measuring apparatus 98A. After each of Steps S1 to S5 is executed, the movement apparatus 17 adjusts the position of the massless septum 12 such that the monitor electrodes 103A and the monitor electrodes 103B of the beam current measuring apparatus 98A are respectively disposed at predetermined positions along the alternate long and short dash line X. An ion beam turning along each of the beam turning trajectories 78 passes through the beam passage 35. When an ion beam passes through gaps between the facing monitor electrodes 103A and the monitor electrodes 103B, a voltage occurring between the electrodes is measured. Measured voltage information equivalent to a beam current is converted into a beam current, and energy information corresponding to the beam current is stored in the memory 107 while being associated with position information regarding the positions of the monitor electrodes on the alternate long and short dash line X in the radial direction of the annular coils, that is, position information regarding the position of the beam turning trajectory 78 in the radial direction.

In Step S13, the massless septum control apparatus 86 positions the massless septum 12 on the beam turning trajectory 78, and specifies a pair of the magnetic poles 32A and 32B based on energy information regarding an ion beam with which a set layer is irradiated, and the position information regarding the beam turning trajectory 78 which stored in the memory 107 while being associated with the energy (voltage information). Similar to Step S13 in Embodiment 1, the amount of movement of the massless septum 12 is obtained. The massless septum control apparatus 86 moves the massless septum 12 toward the injection electrode 18, and positions the specified magnetic poles 32A and 32B on the beam turning trajectory 78 by controlling the movement apparatus 17 based on the amount of movement. In Step S14, the specified pair of magnetic poles 32A and 32B is excited.

In the embodiment, it is possible to obtain the same effects as in Embodiment 1.

The beam current measuring apparatus 98 in Embodiment 1 detects a beam current by causing a turning ion beam to collide with the beam current measuring unit 15. For this reason, the movement apparatus 17A to move the beam current measuring unit 15 is required to perform measurement via destruction of a turning ion beam. In order to measure a beam current of an ion beam turning along the beam turning trajectory 78 positioned at the outermost circumference, the beam current measuring unit 15 is required to be pulled out to the vicinity of the inner surfaces of the annular coils 11A and 11B, and the length of the operation member 16A may have to be increased. Accordingly, an increase in the size of the beam current measuring apparatus 98 becomes a problem.

When the beam current measuring apparatus 98A measures a voltage equivalent to a beam current of a turning ion beam via the facing monitor electrodes 103A and 103B, the beam current measuring apparatus 98A in the embodiment is capable of measuring the voltage and obtaining the beam current corresponding to the voltage without destroying the turning ion beam. Since the movement apparatus 17 of the massless septum 12 can be used to finely adjust the position of the monitor electrodes 103A and 103B, the size of the beam current measuring apparatus 98A can be further reduced than that of the beam current measuring apparatus 98.

As illustrated later in Embodiment 7, the beam current measuring apparatus 98A disposed inside the massless septum 12 may be fixed to the cylindrical body 75B of the return yoke 5B via a bar-shaped support member 108. In this case, the support member 108 attached to the beam current measuring apparatus 98A reaches the outside of the massless septum 12 through the through hole 31D formed in the connection portion 31 of the massless septum 12.

Embodiment 7

Hereinafter, a particle beam irradiation system in Embodiment 7, which is another preferred embodiment of the present invention, will be described with reference to FIGS. 42 and 43.

A particle beam irradiation system 1F in the embodiment has a configuration obtained by replacing the beam current measuring apparatus 98 in the particle beam irradiation system 1C of Embodiment 4 with beam current measuring apparatus 98A. The rest of the configuration of the particle beam irradiation system 1F is the same as that of the particle beam irradiation system 1C. In the particle beam irradiation system 1F, the beam current measuring apparatus 98A is disposed in the recesses 29A, which are respectively formed in the return yokes 5A and 5B, along the alternate long and short dash line X that passes through the central axis C and is perpendicular to the central axis C. The beam current measuring apparatus 98A is attached to the cylindrical portion 75B of the return yoke 5B via the bar-shaped support member 108. A portion of the median plane 77, on which the beam turning trajectories 78 are formed, is present inside the beam passage 35 formed in the beam current measuring apparatus 98A. The monitor electrodes 103A and the monitor electrodes 103B face each other with the median plane 77 interposed therebetween.

In the embodiment, similar to Embodiment 4, among Steps S1 to S6, S23, S24, and S7 to S10 illustrated in Embodiment 1, steps except for Steps S8 and S9 are executed. Each of Steps S11, S12, S22, S7, and S15 to S21 illustrated in FIG. 35 is executed.

In the embodiment, similar to Embodiment 6, in Step S6, during turning of ion beams, the beam current measuring apparatus 98A measures a voltage between the monitor electrodes 103A and the monitor electrodes 103B facing each other. In Step S22, the position of the beam turning trajectory 78 of an ion beam of an energy slightly higher than the energy of an ion beam, with which a set layer is to be irradiated, is specified based on energy information regarding the ion beam with which the layer is irradiated, the degree of energy dampening performed by the energy absorber 62, and position information which is stored in the memory 107 while being associated with voltage information that is beam current information. The energy absorber control apparatus 93 controls the movement apparatus 60 such that the energy absorber 62 is moved to the position of the specified beam turning trajectory 78.

In the embodiment, it is possible to obtain the same effects as in Embodiment 4. In the embodiment, it is also possible to obtain the same effects as those of the beam current measuring apparatus 98A in Embodiment 6.

Embodiment 8

Hereinafter, a particle beam irradiation system in Embodiment 8, which is another preferred embodiment of the present invention, will be described with reference to FIGS. 44, 45, and 46.

In the particle beam irradiation systems such as the particle beam irradiation systems 1 described in Embodiments 1 to 7, each accelerator includes the vacuum chamber 27 formed of the iron cores 14A and 14B. In contrast, in a particle beam irradiation system 1G of the embodiment, an accelerator 4D includes the iron cores 14A and 14B, and further includes a vacuum chamber 27A disposed between the iron cores 14A and 14B. The vacuum chamber 27A is made of non-magnetic material (for example, stainless steel). The iron core 14A is disposed above the vacuum chamber 27A, and the iron core 14B is disposed below the vacuum chamber 27A. The massless septum 12 and the beam current measuring unit 15 of the beam current measuring apparatus 98 are disposed inside the vacuum chamber 27A. The median plane 77, on which the beam turning trajectories 78 are formed, is formed inside the vacuum chamber 27A in such a way as to be perpendicular to the central axis C of the vacuum chamber 27 and the annular coils 11A and 11B. The ion injection tube 3A passes through the base portion 74A of the return yoke 5A included in the iron core 14A, and reaches the inside of the vacuum chamber 27A. The ion inlet port formed at the tip end of the ion injection tube 3A opens inside the vacuum chamber 27A. The suction tube 26, which is disposed on the extension line of the central axis of the ion injection tube 3A, is attached to the base portion 74B in a state where the suction tube 26 has passed through the base portion 74B of the return yoke 5B. The suction tube 26 is connected to the vacuum chamber 27A, and opens inside the vacuum chamber 27A. The injection electrode 18 is attached to the tip end of the ion inlet tube 3A.

The rest of the configuration of the particle beam irradiation system 1G including the iron cores 14A and 14B is the same as that of the particle beam irradiation system 1.

The operation member 16 attached to the massless septum 12 and the operation member 16A attached to the beam current measuring unit 15 pass through the vacuum chamber 27A and the cylindrical portion 75B of the return yoke 5B, and reach the outside of the return yoke 5B. On the outside of the return yoke 5B, the operation members 16 and 16A are respectively connected to the movement apparatuses 17 and 17A. The septum magnet 19 is attached to the vacuum chamber 27A and the cylindrical portion 75B. The beam extraction path 20 formed in the septum magnet 19 communicates with the beam path 48 of the beam transport 13. The inlet of the beam extraction path 20 is positioned inside the vacuum chamber 27A.

The concentric trajectory region and the eccentric trajectory region surrounding the concentric trajectory region are formed on the median plane 77 inside the vacuum chamber 27A. The concentric trajectory region and the concentric trajectory region surround the injection electrode 18. Similar to the embodiments, the beam turning trajectories 78 formed in the concentric trajectory region are concentrated on the inlet side of the beam extraction path 20. In the embodiment, the positions of the injection electrode 18 and the ion inlet port are offset toward the inlet of the beam extraction path 20 from the central axis C of the annular coils, that is, the center of gravity of the annular coils which is positioned on the central axis C. The injection electrode 18 and the ion inlet port are positioned at a position that is different from that of the center of gravity of the annular coils in a radial direction of the accelerator 4D. Similar to Embodiment 1, the magnetic poles 7A to 7F formed in each of the iron cores 14A and 14B are disposed to surround the position of the ion inlet port, and extend radially from the position of the ion inlet port. In addition, similar to Embodiment 1, the recesses 29A to 29F formed in each of the iron cores 14A and 14B are disposed to surround the position of the ion inlet port, and extend radially from the position of the ion inlet port.

In the embodiment, similar to Embodiment 1, a magnetic field distribution illustrated in FIG. 10 is formed on the median plane 77. A target volume of the patient 56 on the treatment bed 55 is irradiated with ion beams by executing each of Steps S1 to S6, S23, S24, S7 to S14, S7, and S15 to S21.

In the embodiment, it is possible to obtain the same effects as in Embodiment 1. In the embodiment, the vacuum chamber 27A is separately provided, and thus, it is not necessary to seal respective facing surfaces of the cylindrical portion 75A of the return yoke 5A and the cylindrical portion 75B of the return yoke 5B which face each other as illustrated in Embodiment 1. In contrast, in the embodiment, the vacuum chamber 27A is disposed between the iron cores 14A and 14B, and thus, the size of the accelerator 4D in the embodiment becomes larger than that of the accelerator 4 in Embodiment 1.

As illustrated in FIG. 47, the massless septum 12 may be disposed outside the vacuum chamber 27A, and the vacuum chamber 27A may be disposed between the magnetic poles 32A and the magnetic poles 32B facing the magnetic poles 32A of the massless septum 12. In this case, the beam current measuring unit 15 is disposed on the median plane 77 inside the vacuum chamber 27A. It is possible to eject ion beams turning along the beam turning trajectories 78 which are formed on the median plane 77 inside the vacuum chamber 27A, and to extract the ion beams to the beam transport 13 through the beam extraction path 20, via the massless septum 12 disposed in this manner.

Embodiment 9

Hereinafter, a particle beam irradiation system in Embodiment 9, which is another preferred embodiment of the present invention, will be described with reference to FIG. 48.

Similar to the particle beam irradiation system 1E, in a particle beam irradiation system 1F of the embodiment, the vacuum chamber 27A is disposed between the iron cores 14A and 14B. The particle beam irradiation system 1F includes an accelerator 4E including the iron cores 14A and 14B, the vacuum chamber 27A, the beam current measuring unit 15 disposed inside the vacuum chamber 27A, and the energy absorber 62. The operation member 16A attached to the beam current measuring unit 15 and the operation member 62 attached to the energy absorber 62 pass through the vacuum chamber 27A and the cylindrical portion 75B of the return yoke 5B, and reach the outside of the return yoke 5B.

In the embodiment, similar to Embodiment 4, a magnetic field distribution illustrated in FIG. 10 is formed on the median plane 77. Among Steps S1 to S6, S23, S24, and S7 to S10 illustrated in Embodiment 1, steps except for Steps S8 and S9 are executed. Each of Steps S11, S12, S22, S7, and S15 to S21 illustrated in FIG. 32 is executed. In the embodiment, a target volume of the patient 56 on the treatment bed 55 is also irradiated with ion beams which are extracted from the vacuum chamber 27A into the beam transport 13.

In the embodiment, it is possible to obtain the same effects as in Embodiment 4. In contrast, in the embodiment, the vacuum chamber 27A is disposed between the iron cores 14A and 14B, and thus, the size of the accelerator 4D in the embodiment becomes larger than that of the accelerator 4B in Embodiment 4.

In the present invention, an ion source which generates carbon ions ($C^{4+}$) may be used instead of the ion source 3 that generates protons, the carbon ions ($C^{4+}$) may be converted into carbon ions ($C^{6+}$) via charge conversion by a charge converter to form a carbon ion beam ($C^{6+}$ ion beam) in the accelerator, and the generated carbon ion beam may be extracted from the accelerator and be guided to the irradiation apparatus 7 via the beam transport. In this case, a target volume of the patient 56 on the treatment bed 55 is irradiated with carbon ion beams instead of proton ion beams. An ion source which generates helium ions may be used as the ion source 3, and helium ion beams may be extracted from the accelerator into the beam transport.

In this application, a positional relationship between elements, which are not present on the plane perpendicular to the central axis C of the annular coils 11A and 11B, represents a positional relationship between the elements on the median plane 77 when the elements are projected onto the median plane 77 in the direction of the central axis C. In Embodiments 8 and 9, examples of a positional relationship between such elements include a positional relationship between the ion inlet port (ion injection port) formed at the tip end of the ion injection tube 3A, the injection electrode 18, or the ion injection portion and each of the magnetic poles 7A to 7F, the radiofrequency acceleration electrodes 9A to 9D, the beam extraction path 20, and the recesses 29A to 29F; and a positional relationship among the magnetic poles 7A to 7F, the radiofrequency acceleration electrodes 9A to 9D, the beam extraction path 20, and the recesses 29A to 29F; and a positional relationship between the ion inlet port and the inlet of the beam extraction path 20.

REFERENCE SIGNS LIST 1, 1A, 1B, 1C, 1D, 1E, 1F: particle beam irradiation system
2, 2A, 2B: ion beam generator
3: ion source
3A: ion injection tube
4, 4A, 4B, 4C, 4D, 4E: accelerator
6: rotating gantry
7: irradiation apparatus
7A to 7F, 32A, 32B: magnetic pole
8A to 8F: trim coil
9A to 9D: radiofrequency acceleration electrodes
11A, 11B: annular coil
12: massless septum
13, 13B: beam transport
14A, 14B: iron core
15: beam current measuring unit
17, 17A, 60: movement apparatus
18: injection electrode
19: septum magnet
20, 48: beam path
24A to 24P: bent point
27, 27A: vacuum chamber
29A to 29F: recess
30, 30A, 30B: iron core member
31A, 31B: iron core portion
31C: connection portion
33A, 33B: coil
35: beam passage
36: radiofrequency power supply
37, 40, 57, 80, 82: power supply
51, 52: scanning magnet
53: beam point monitor
54: dose monitor
62: energy absorber
65: control system
66: central control apparatus
69, 69A, 69B: accelerator and transport control apparatus
70: scanning control apparatus
76: beam turning region
77: median plane
83: injection electrode control apparatus
84: beam current measuring unit control apparatus
85: magnet control apparatus
86: massless septum control apparatus
88: rotation control apparatus
89: irradiation point control apparatus
91: dose determination apparatus
92: layer determination apparatus
93: energy absorber control apparatus
94: coil current control apparatus
98, 98A: beam current measuring apparatus
99: radiofrequency voltage control apparatus
101: monitor housing
103: monitor electrode

The invention claimed is:

1. An accelerator comprising:
an annular main coil;
a radiofrequency acceleration apparatus configured to accelerate ion beams on multiple annular beam turning trajectories;
a beam extraction path configured to extract the accelerated ion beams to an outside; and
a bending magnet apparatus configured to separate the ion beams from the beam turning trajectories at different positions in a radial direction of the main coil, the bending magnet apparatus including:
a first magnetic pole member including a first connecting portion in which multiple first protrusions are formed and first coils are respectively provided in the first protrusions, and
a second magnetic pole member including a second connecting portion in which multiple second protrusions respectively facing the multiple first protrusions are formed and second coils are respectively provided in the second protrusions; and
a first control apparatus configured to control an excitation current supplied to the first coils and the second coils.

2. The accelerator according to claim 1, further comprising:
a first movement apparatus configured to move the bending magnet apparatus in the radial direction of the main coil.

3. The accelerator according to claim 1, further comprising:
an energy absorber configured to damp energies of the turning ion beams;
a first movement apparatus configured to move the bending magnet apparatus in the radial direction of the main coil; and a second movement apparatus configured to move the energy absorber in the radial direction of the main coil.

4. The accelerator according to claim 1, wherein the first magnetic pole member is connected to the second magnetic pole member.

5. The accelerator according to claim 2, further comprising:
a beam measuring instrument configured to measure turning positions of the ion beams; and
a first control apparatus configured to control the first movement apparatus and move the bending magnet apparatus on the basis of position information of the ion beams measured by the beam measuring instrument.

6. The accelerator according to claim 1, further comprising:
a beam measuring instrument configured to measure turning positions of the ion beams;
wherein the first control apparatus is configured to control, on the basis of position information of the ion beams measured by the beam measuring instrument, the excitation current supplied to the bending magnet apparatus.

7. The accelerator according to claim 5, further comprising:
wherein the first control apparatus is configured to control, on the basis of position information of the ion beams measured by the beam measuring instrument, the excitation current supplied to the bending magnet apparatus.

8. The accelerator according to claim 1, wherein
an energy absorber configured to separate the ion beams from the beam turning trajectories at different positions in a radial direction of the main coil and configured to damp energies of the turning ion beams; and
a movement apparatus configured to move the energy absorber in the radial direction of the main coil.

9. An accelerator comprising:
an annular main coil;
a radiofrequency acceleration apparatus configured to accelerate ion beams on multiple annular beam turning trajectories;
a beam extraction path configured to extract the accelerated ion beams to an outside;
a bending magnet apparatus configured to separate the ion beams from the beam turning trajectories at different positions in a radial direction of the main coil;
an energy absorber configured to damp energies of the turning ion beams;
a first movement apparatus configured to move the bending magnet apparatus in the radial direction of the main coil;
a second movement apparatus configured to move the energy absorber in the radial direction of the main coil; and
a beam measuring instrument configured to measure turning positions of the ion beams; and
a first control apparatus configured to control the second movement apparatus and move the energy absorber on the basis of position information of the ion beams measured by the beam measuring instrument.

10. An accelerator comprising:
an ion source;
an annular main coil;
a radiofrequency acceleration apparatus configured to accelerate ion beams on multiple annular beam turning trajectories;
a beam extraction path configured to extract the accelerated ion beams to an outside;
a beam separation apparatus configured to separate the ion beams from the beam turning trajectories at different positions in a radial direction of the main coil;
an ion injection portion disposed closer to an inlet of the beam extraction path than a central axis of the main coil, the ion injection portion injecting ions from the ion source into a vacuum container;
multiple magnetic poles radially extending around a position of the ion injection portion, and tip ends of the multiple magnetic poles face the position of the ion injection portion;
trim coils installed in the magnetic poles; and
multiple recesses formed around the position of the ion injection portion and radially extending around the position of the ion injection portion,
wherein the magnetic poles and the recesses are alternately disposed around the position of the ion injection portion.

11. The accelerator according to claim 10, further comprising:
a beam measuring instrument configured to measure turning positions of the ion beams; and
a control apparatus configured to control, on the basis of position information of the ion beams measured by the beam measuring instrument, an excitation current supplied to the trim coils.

12. The accelerator according to claim 9, further comprising:
a second control apparatus configured to control an excitation current supplied to the first coils and the second coils.

13. The accelerator according to claim 10, wherein the bending magnet apparatus is disposed in the recesses.

14. The accelerator according to claim 10, wherein the magnetic poles are disposed according to energies of the ion beams such that the ion beams turn along the multiple beam turning trajectories formed with centers eccentric with respect to each other.

15. The accelerator according to claim 10, wherein the multiple magnetic poles are disposed to form a concentric trajectory region in which the ion beams turn along multiple concentric annular beam turning trajectories formed around the ion injection portion and an eccentric trajectory region in which the ion beams turn along the multiple beam turning trajectories with the centers eccentric with respect to each other.

16. The accelerator according to claim 10, wherein the magnetic poles are disposed such that a high magnetic field strength region and a low magnetic field strength region are alternately formed along the beam turning trajectories of the ion beams.

17. The accelerator according to claim 10, wherein the magnetic poles are disposed such that gaps between the beam turning trajectories are denser in a region between the ion injection portion and the inlet of the beam extraction path than a region in which the beam separation apparatus is disposed.

18. A particle beam irradiation system comprising:
the accelerator according to claim 1;
an irradiation apparatus configured to output, to an irradiation target, ion beams extracted from the accelerator; and a beam transportation apparatus configured to transport the ion beams extracted from the accelerator to the irradiation apparatus.

* * * * *